United States Patent [19]

Di Malta et al.

[11] Patent Number: 5,661,169

[45] Date of Patent: Aug. 26, 1997

[54] 1-BENZYL-1,3-DIHYDRO-2H-BENZIMIDAZOL-2-ONE DERIVATIVES, THEIR PREPARATION AND THE PHARMACEUTICAL COMPOSITIONS CONTAINING THEM

[75] Inventors: Alain Di Malta, Saint Clement de Riviere; Georges Garcia, St. Gely Du Fesc; Daniel Mettefeu, Grabels; Richard Roux, Vailhauques; Claudine Serradeil-Legal, Escalquens, all of France

[73] Assignee: SANOFI, Paris, France

[21] Appl. No.: 498,542

[22] Filed: Jul. 5, 1995

[30] Foreign Application Priority Data

Jul. 5, 1994 [FR] France .................................. 94 08278

[51] Int. Cl.[6] .................................................. A61K 31/415
[52] U.S. Cl. ........................ 514/387; 544/139; 546/199; 548/304.7; 548/306.1; 548/306.4
[58] Field of Search ........................ 548/306.4, 304.7, 548/306.1; 514/387

[56] References Cited

U.S. PATENT DOCUMENTS

| | | |
|---|---|---|
| 4,377,695 | 3/1983 | Lautenschläger et al. . |
| 5,200,422 | 4/1993 | Olesen et al. . |
| 5,258,510 | 11/1993 | Ogawa et al. . |

FOREIGN PATENT DOCUMENTS

| | | |
|---|---|---|
| 1573739 | 7/1969 | France . |
| WO-A-9315051 | 8/1993 | WIPO . |

*Primary Examiner*—Robert W. Ramsuer
*Attorney, Agent, or Firm*—Bacon & Thomas

[57] ABSTRACT

The present invention relates to 1-benzyl-1,3-dihydro-2H-benzimidazol-2-one derivatives, of formula:

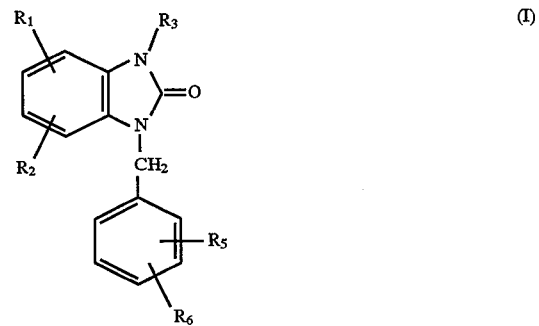

and to the possible salts thereof, to a process for their preparation and to the pharmaceutical compositions containing them.

These compounds have an affinity for the vasopressin and/or oxytocin receptors.

25 Claims, No Drawings

1-BENZYL-1,3-DIHYDRO-2H-BENZIMIDAZOL-2-ONE DERIVATIVES, THEIR PREPARATION AND THE PHARMACEUTICAL COMPOSITIONS CONTAINING THEM

The present invention relates to 1-benzyl-1,3-dihydro-2H-benzimidazol-2-one derivatives, to their preparation and to the pharmaceutical compositions containing them.

The compounds according to the present invention have an affinity for the vasopressin and/or oxytocin receptors.

Vasopressin is a hormone known for its anti-diuretic effect and its effect in the regulation of arterial pressure. It stimulates several types of receptors: $V_1$ ($V_{1a}$, $V_{1b}$), V2. These receptors are located in the liver, vessels (coronary, renal and cerebral vessels), platelets, the kidney, the uterus, the adrenal glands, the central nervous system and the pituitary gland. Oxytocin has a peptide structure similar to that of vasopressin. Oxytocin receptors are also found on the smooth muscle of the uterus, as well as on myoepithelial cells of the mammary gland, in the central nervous system and in the kidney. The location of the various receptors is described in: S. Jars et al., Vasopressin and oxytocin receptors: an overview, in Progress in Endocrinology, H. Imura and K. Shizurne ed., Experts Medica, Amsterdam, 1988, 1183–1188, and in the following articles: Presse Médicale, 1987, 16, (10), 481–485, J. Lab. Clin. Med., 1989, 114 (6), 617–632 and Pharmacol. Rev., 1991, 43 (1), 73–108. Vasopressin thus exerts cardiovascular, hepatic, anti-diuretic, aggregating effects and effects on the central and peripheral nervous system, and on the uterine sphere. Oxytocin is involved in parturition, lactation and sexual behavior.

The compounds according to the present invention make it possible either to mimic the effects of the hormone (for the agonists), or to inhibit them (for the antagonists), in a selective manner. The vasopressin receptor antagonists may be involved in the regulation of central and peripheral circulation, in particular coronary, renal and gastric circulations, as well as in water regulation and the release of adrenocorticotropic hormone (ACTH). The vasopressin agonists may advantageously replace vasopressin or analogs thereof in the treatment of diabetes insipidus; they may also be used in the treatment of enuresis and in the regulation of hemostasis: treatment of hemophilia, von Willebrand's syndrome, antidote to platelet aggregating agents (F. A. Laszlo, Pharmacol. Rev., 1991, 43, 73–108. Drug Investigation, 1990, 2 (Suppl. 5), 1–47). The hormones themselves: vasopressin and oxytocin, as well as some of the peptide or non-peptide analogs thereof, are used in therapy and have demonstrated their effectiveness. Several reviews and numerous articles from the literature may be mentioned: Vasopressin, P. Gross et al., ed. John Libbey Eurotext, 1993, in particular p. 243–257 and p. 549–562; F. A. Laszlo and F. A. Laszlo Jr., Clinical perspectives for vasopressin antagonists, Drug News Perspect., 1993, 6 (8); W. G. North, J. Clin. Endocrinol., 1991, 73, 1316–1320; J. J. Legros et al., Prog. Neuro-Pharmacol. Biol. Psychiat., 1988, 12, 571–586; K. E. Andersson et al., Drugs Today, 1988, 24 (7), 509–528; D. L. Stump et al., Drugs, 1990, 39, 38–53; S. Caltabiano et al., Drugs Future, 1988, 13, 25–30; Y. Mura et al., Clin. Nephrol. 1993, 40, 60–61; Faseb J., 1994, 8, (5), A 587:3398.

Thus, the compounds according to the invention are especially useful in the treatment of complaints of the central and peripheral nervous system, of the cardiovascular system, of the renal sphere, of the gastric sphere and in sexual behavior disorders, in man and in animals.

1-Benzyl-1,3-dihydro-2H-benzimidazol-2-one derivatives have been prepared and have demonstrated a pharmacological activity. There may for example be mentioned the following patents or patent applications:

FR 1,573,739; pharmacology not specified;

DE 2,400,094, relating to compounds with antihypertensive activity;

DE 2,527,261, relating to compounds with neuroleptic activity;

DE 2,714,437, relating to compounds with anti-allergic activity;

EP 260,744, relating to compounds with inhibitory activity on the synthesis of androgens from steroids;

JP 57018674, relating to compounds with a depressant activity on the central nervous system, an antihistamine or platelet anti-aggregating activity or an inhibitory activity on phosphodiesterase;

DE 2,717,439, relating to compounds with activity on the central nervous system, possessing antidepressant properties;

DE 2,338,813, relating to compounds with anti-inflammatory activity;

DE 2,626,128, relating to compounds with anti-hypertensive activity;

JP 53009770, relating to compounds with analgesic and central depressant activity;

EP 254,627, relating to compounds with antihistamine and antispasmodic activity;

U.S. Pat. No. 4,209,527, relating to compounds with inhibitory activity on aldose reductase;

EP 51,827, relating to compounds with anti-allergic, anti-asthmatic and anti-inflammatory activity.

The following publications may also be mentioned:

Eur. J. Pharmacol., Mol. Pharmacol. Sect., 1992, 226 (2), 109–120, relating to dopamine antagonist compounds;

Eur. J. Med. Chem., 1992, 27 (8), 779–789, relating to compounds with inhibitory activity on aldose reductase;

Eur. J. Med. Chem.—Chim Ther., 1981, 16 (4), 321–326, relating to compounds with antiulcer and antisecretory activity.

Patent application EP 454,330 describes in particular, as synthetic intermediate, a 1,3-dihydro-2H-benzimidazol-2-one derivative of formula:

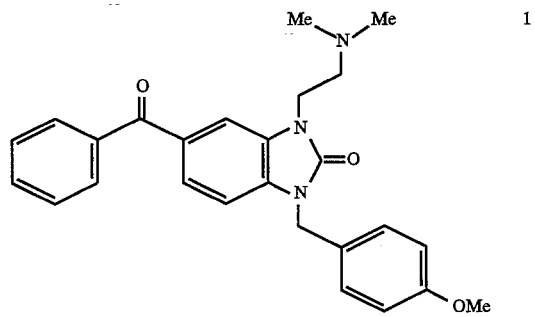

Recently, several patent applications have described families of compounds with non-peptide structure having an activity on the vasopressin and/or oxytocin receptors. Applications EP 382,185, EP 444,945, EP 514,667, EP 469,984 and EP 526,384, applications WO 91/05549 and WO 93/15051 and patent application JP-03/127732 may be mentioned.

According to one of its aspects, the subject of the present invention is compounds of formula:

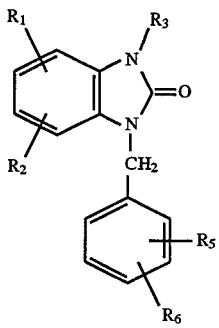

in which:

R$_1$ represents a halogen; a (C$_1$-C$_7$)alkyl; a (C$_1$-C$_7$)alkylthio; a phenylthio; a trifluoromethyl; a cyano; a nitro; a group —NR$_7$R$_8$; a hydroxyl; a (C$_1$-C$_7$)alkoxy; a (C$_3$-C$_7$)cycloalkyloxy; a (C$_3$-C$_7$)cycloalkylmethoxy; a phenoxy; a benzyloxy; an ω-halo(C$_1$-C$_7$)alkyloxy; a polyhalo(C$_1$-C$_7$)alkyloxy, an ω-hydroxy(C$_2$-C$_7$)alkyloxy; an ω-methoxy(C$_2$-C$_7$)alkyloxy;

R$_2$ represents a hydrogen, a halogen, a (C$_1$-C$_7$)alkyl;

R$_3$ represents R$_4$; a group —(CH$_2$)$_p$—R$_4$; an indanyl; a hexahydroindanyl; an adamantyl; a noradamantyl; a norbornyl; a (C$_1$-C$_8$)alkyl unsubstituted or substituted with a (C$_1$-C$_4$)alkoxy; a cyclohexyl substituted with a di(C$_1$-C$_7$)alkylamino, a carboxyl, a (C$_1$-C$_4$)alkoxycarbonyl, a hydroxyl, a 2-tetrahydropyranyloxy, a (C$_1$-C$_4$)alkoxy(C$_1$-C$_4$)alkoxy or a phenyl(C$_1$-C$_2$)alkoxy(C$_1$-C$_4$)alkoxy;

R$_4$ represents a group —NR$_9$R$_{10}$; a (C$_3$-C$_7$)cycloalkyl unsubstituted or substituted once or twice with a (C$_1$-C$_4$)alkyl or a (C$_1$-C$_4$)alkoxy; a furyl; a thienyl; a pyrrolyl; a triazolyl; a tetrazolyl; a pyridyl; a pyridyl N-oxide; a pyrimidinyl; a pyrazolyl; a pyrazinyl; a 4-tetrahydropyranyl; a 3-azetidinyl substituted in position 1 with R$_{11}$; a 4-piperidyl substituted in position 1 with R$_{11}$; a group Ar;

R$_5$ represents a hydrogen; a (C$_1$-C$_7$)alkyl; a (C$_1$-C$_7$)alkoxy; a halogen; a hydroxyl; a trifluoromethyl;

R$_6$ represents a cyano; a group —CH$_2$NR$_7$R$_8$; a nitro; a group —NR$_{12}$R$_{13}$; a group —NHOH; a guanidino which is unsubstituted or substituted in position 1 with a (C$_1$-C$_7$)alkyl and/or in position 3 with one or two (C$_1$-C$_7$)alkyls, a group Ar or a group —CH$_2$—Ar and/or in position 2 with a cyano; a group —OR$_{14}$; a group —SR$_{14}$; a (C$_1$-C$_7$)alkylcarbonyl; a group —CONR$_{15}$R$_{16}$; a thiocarbamoyl which is free or substituted with one or two (C$_1$-C$_7$)alkyls; a carboxyl; a (C$_1$-C$_7$)alkoxycarbonyl; a group —COO—Ar; a group —COO—CH$_2$—Ar; a group —CO—NH—CR$_{17}$R$_{18}$—COR$_{19}$; a group —SO$_2$NR$_{20}$R$_{21}$; a group —NHSO$_2$—(C$_1$-C$_7$)alkyl; a group —NHSO$_2$—Ar; a group —NHSO$_2$—CH$_2$—Ar; a dimethylaminosulfonamido;

R$_7$ and R$_8$ each independently represent a hydrogen or a (C$_1$-C$_7$)alkyl; R$_8$ may moreover represent a protecting group;

R$_9$ and R$_{10}$ each independently represent a hydrogen or a (C$_1$-C$_7$)alkyl;

or alternatively R$_9$ and R$_{10}$, together with the nitrogen atom to which they are attached, constitute a heterocycle chosen from morpholine, thiomorpholine, azetidine, pyrrolidine, piperidine, piperazine substituted in position 4 with R$_{11}$ or perhydroazepine;

R$_{11}$ represents a hydrogen; a (C$_1$-C$_7$)alkyl; a phenyl; a benzyl; a (C$_1$-C$_7$)alkylcarbonyl; a benzoyl; a (C$_1$-C$_7$)alkoxycarbonyl; a phenoxycarbonyl; a carbamoyl which is unsubstituted or substituted with one or two (C$_1$-C$_7$)alkyls;

R$_{12}$ and R$_{13}$ each independently represent a hydrogen; a (C$_1$-C$_7$)alkyl; a group —CH$_2$—Ar; R$_{13}$ may moreover represent a (C$_3$-C$_7$)cycloalkylmethyl; a group Ar; a group —CH$_2$CH$_2$Ar; a (C$_3$-C$_8$)alkenyl; a (C$_1$-C$_7$)alkylcarbonyl; a (C$_1$-C$_7$)alkylthiocarbonyl; a (C$_3$-C$_7$)cycloalkylcarbonyl; a (C$_3$-C$_7$)cycloalkylthiocarbonyl; a group —CO—Ar; a group —CO—CH$_2$—Ar; an ω-R$_7$R$_8$N(C$_2$-C$_7$)alkylcarbonyl; an (ω-hydroxy (C$_1$-C$_7$)alkylcarbonyl; an ω-benzyloxy(C$_1$-C$_7$)alkylcarbonyl; a pyridylcarbonyl; a methylpyridylcarbonyl; a thienylcarbonyl; a furylcarbonyl; a 4-piperidylcarbonyl substituted in position 1 with R$_{11}$; a (C$_1$-C$_7$)alkoxycarbonyl; a phenoxycarbonyl; a phenoxythiocarbonyl; a benzyloxycarbonyl; a group —CONR$_{22}$R$_{23}$; a group —CSNR$_{22}$R$_{23}$; a group —CO—CR$_{17}$R$_{18}$—NR$_7$R$_8$; a group —CR$_{17}$R$_{18}$COR$_{19}$; a group —(CH$_2$)$_r$—COR$_{19}$; a group —CO—(CH$_2$)$_u$—COR$_{19}$;

or alternatively R$_{12}$ and R$_{13}$, together with the nitrogen atom to which they are attached, constitute hydantoin, N-methylhydantoin or a heterocyclic radical chosen from 1-pyrrolyl, Δ3-pyrrolin-1-yl, 1-pyrrolidinyl, 2-isoindolinyl in which the benzene ring is unsubstituted or substituted with a halogen, a (C$_1$-C$_7$)alkyl, a trifluoromethyl or a (C$_1$-C$_7$)alkoxy;

R$_{14}$ represents hydrogen; a (C$_1$-C$_7$)alkyl; a phenyl; a benzyl; a (C$_3$-C$_7$)cycloalkyl; a (C$_3$-C$_7$)alkenyl; an ω-halo(C$_2$-C$_7$)alkyl; a polyhalo(C$_1$-C$_7$)alkyl; an ω-hydroxy(C$_2$-C$_7$)alkyl; a (C$_1$-C$_7$)alkylcarbonyl; a benzoyl; an ω-carboxy(C$_1$-C$_7$)alkyl; an ω-(C$_1$-C$_4$)alkoxycarbonyl(C$_1$-C$_7$)alkyl; an ω-benzyloxycarbonyl (C$_1$-C$_7$)alkyl; an ω-R$_7$R$_8$N(C$_2$-C$_7$)alkyl; an ω-carbamoyl(C$_1$-C$_7$)alkyl in which the carbamoyl is free or substituted with one or two (C$_1$-C$_7$)alkyls;

R$_{15}$ and R$_{16}$ each independently represent a hydrogen or a (C$_1$-C$_7$)alkyl; R$_{16}$ may moreover represent a (C$_3$-C$_7$)cycloalkyl which is unsubstituted or substituted with a (C$_1$-C$_4$)alkyl; a group Ar; a pyridyl; a methylpyridyl; a 4-piperidyl substituted in position 1 with R$_{11}$; a methylpiperid-4-yl; a 1-pyrrolidinyl; a 1-piperidyl; a 4-morpholinyl; a (C$_1$-C$_7$)alkyl substituted with one or more halogens or with R$_{24}$;

or alternatively R$_{15}$ and R$_{16}$, together with the nitrogen atom to which they are attached, represent a heterocyclic radical R$_{25}$;

R$_{17}$ and R$_{18}$ each independently represent hydrogen; a (C$_1$-C$_7$)alkyl; a benzyl;

or alternatively R$_{17}$ and R$_{18}$, together with the carbon atom to which they are attached, constitute a (C$_3$-C$_7$)cycloalkyl;

R$_{19}$ represents a hydroxyl; a (C$_1$-C$_7$)alkoxy; an amino which is free or substituted with one or two (C$_1$-C$_7$)alkyls;

R$_{20}$ and R$_{21}$ each independently represent hydrogen; a (C$_1$-C$_7$)alkyl; R$_{21}$ may moreover represent a (C$_3$-C$_7$)cycloalkyl;

or alternatively R$_{20}$ and R$_{21}$, together with the nitrogen atom to which they are attached, constitute a heterocyclic radical R$_{25}$;

R$_{22}$ and R$_{23}$ each independently represent hydrogen; a (C$_1$-C$_7$)alkyl; R$_{23}$ may moreover represent a (C$_3$-C$_7$)

cycloalkyl; an adamantyl; a group Ar; a hydroxyl; a (C$_1$-C$_4$)alkoxy; a (C$_1$-C$_7$)alkyl substituted with a group Ar, a pyridyl, a hydroxyl, a (C$_1$-C$_7$)alkoxy, a group —NR$_7$R$_8$, a carboxyl or a (C$_1$-C$_7$)alkoxycarbonyl;

or alternatively R$_{22}$ and R$_{23}$, together with the nitrogen atom to which they are attached, constitute a heterocyclic radical R$_{25}$;

R$_{24}$ represents a hydroxyl; a (C$_1$-C$_7$)alkoxy; a cyano; a carboxyl; a (C$_1$-C$_7$)alkoxycarbonyl; a group —NR$_7$R$_8$; a carbamoyl which is free or substituted with one or two (C$_1$-C$_7$)alkyls; a benzyloxycarbonyl; a group Ar; a (C$_3$-C$_7$)cycloalkyl; an adamantyl; a 1-pyrrolidinylcarbonyl; a 1-piperidylcarbonyl; a perhydro-1-azepinylcarbonyl; a heterocyclic radical chosen from a pyridyl, a methylpyridyl, a furanyl, a tetrahydrofuranyl, a thienyl, a methylthienyl, a 1-pyrrolinyl, a 1-piperidyl or a perhydro-1-azepinyl;

R$_{25}$ represents a 4-morpholinyl; a 4-thiomorpholinyl; a 1-azetidinyl which is unsubstituted or substituted in position 2 with a carboxyl, a (C$_1$-C$_4$)alkoxycarbonyl or in position 3 with a group —NR$_7$R$_8$, a (C$_1$-C$_7$)alkyl, a phenyl, a benzyl or a (C$_1$-C$_7$)alkylcarbonyl; a perhydro-1-azepinyl; a 1-piperazinyl which is unsubstituted or substituted in position 4 with a (C$_1$-C$_7$)alkyl, a phenyl, a benzyl, a (C$_1$-C$_7$)alkylcarbonyl, a (C$_1$-C$_7$)alkoxycarbonyl or a benzyloxycarbonyl; a 1-piperidyl which is unsubstituted or substituted in position 4 with a (C$_1$-C$_7$)alkyl, a phenyl, a benzyl, a (C$_1$-C$_7$)alkylcarbonyl or a group —NR$_7$R$_8$; a cis-2,6-dimethyl-1-piperidyl; a 1-pyrrolidinyl which is unsubstituted or substituted with a (C$_1$-C$_7$)alkyl, a phenyl, a benzyl, a (C$_1$-C$_7$)alkylcarbonyl, a hydroxymethyl, a carboxyl, a (C$_1$-C$_7$)alkoxycarbonyl or a carbamoyl which is unsubstituted or substituted with one or two (C$_1$-C$_7$)alkyls;

Ar represents a phenyl which is unsubstituted or substituted one or more times with a substituent chosen from: a halogen atom, a (C$_1$-C$_7$)alkyl, a trifluoromethyl, a hydroxyl, a (C$_1$-C$_7$)alkoxy, a carboxyl, a (C$_1$-C$_7$)alkoxycarbonyl, a (C$_1$-C$_7$)alkylcarbonyloxy, a nitro, a cyano, an amino, a (C$_1$-C$_7$)alkylamino, a di(C$_1$-C$_7$)alkylamino, the said substituents being identical or different;

t represents an integer which may range from 2 to 5;

u represents an integer which may range from 0 to 7;

p represents an integer which may range from 1 to 8 and the possible salts thereof, on condition that when R$_6$ represents a methoxy, R$_5$ is other than hydrogen.

When a compound according to the invention has one or more asymmetric carbons, the invention comprises all the optical isomers of this compound.

The salts of the compounds of formula (I) according to the present invention comprise those with inorganic or organic acids which allow a suitable crystallization or separation of the compounds of formula (I), such as picric acid, oxalic acid or an optically active acid, for example a mandelic acid or a camphorsulfonic acid, and those which form physiologically acceptable salts such as the hydrochloride, hydrobromide, sulfate, hydrogen sulfate, dihydrogen phosphate, maleate, fumarate and 2-naphthalenesulfonate.

The salts of the compounds of formula (I) also comprise the salts with organic or inorganic bases, for example the alkali metal or alkaline-earth metal salts such as the sodium, potassium and calcium salts, the sodium and potassium salts being preferred, or with an amine, such as tromethane, or alternatively the arginine or lysine salts or the salts of any physiologically acceptable amine.

According to the present invention, the term halogen refers to an atom chosen from fluorine, chlorine, bromine or iodine, preferably fluorine or chlorine.

According to the present invention, the term nitrogen-protecting group refers to a group such as: a (C$_1$-C$_4$)alkyl, for example a methyl or a tert-butyl; a benzyl; a substituted benzyl such as p-nitrobenzyl, p-chlorobenzyl or p-methoxybenzyl; a benzhydryl; a trityl; a benzoyl; a (C$_1$-C$_4$)alkylcarbonyl, for example an acetyl; a (C$_1$-C$_4$)alkoxycarbonyl, for example a methoxycarbonyl, an ethoxycarbonyl or a tert-butoxycarbonyl; a benzyloxycarbonyl.

According to the present invention, the term C$_1$-C$_7$alkyl or C$_1$-C$_8$ or C$_1$-C$_4$alkyl respectively refers to a straight or branched C$_1$-C$_7$ or C$_1$-C$_8$ or C$_1$-C$_4$alkyl respectively. The term C$_1$-C$_7$alkoxy or respectively C$_1$-C$_4$alkoxy refers to a straight or branched C$_1$-C$_7$ or C$_1$-C$_4$alkoxy respectively.

By convention, in the description which follows and in the claims, the 1,3-dihydro-2H-benzimidazol-2-one heterocycle is numbered as follows for the compounds according to the invention:

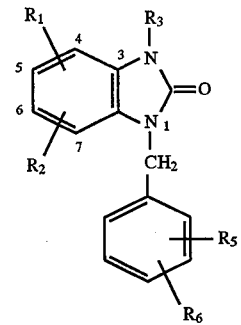

(I)

The subject of the present invention is advantageously the compounds of formula:

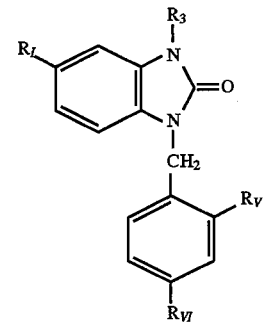

(Ia)

in which

R$_I$ represents a (C$_1$-C$_4$)alkoxy or a chlorine or fluorine atom,

R$_V$ represents hydrogen or a methoxy,

R$_{VI}$ represents a (C$_1$-C$_7$)alkylcarboxamido, a group —NHCO—Ar, a group —CONR$_{15}$R$_{16}$, a group —NR$_{12}$CONR$_{22}$R$_{23}$;

and the substituents R$_3$, Ar, R$_{12}$, R$_{15}$, R$_{16}$, R$_{22}$ and R$_{23}$ are as defined above for the compounds of formula (I); as well as the salts thereof.

The compounds of formula (Ia) in which R$_3$ represents a cyclohexyl or a group Ar are preferred compounds.

In the description and in the examples, the following abbreviations are used.

DCM: dichloromethane

Ether: diethyl ether

Iso ether: diisopropyl ether
CCl$_4$: carbon tetrachloride
MeOH: methanol
EtOH: ethanol
EtOAc: ethyl acetate
DMF: dimethylformamide
THF: tetrahydrofuran
DIPEA: diisopropylethylamine
AcOH: acetic acid
HCl: hydrochloric acid
TFA: trifluoroacetic acid
Na$_2$SO$_4$: sodium sulfate
NaOH: sodium hydroxide
NaHCO$_3$: sodium hydrogen carbonate
K$_2$CO$_3$: potassium carbonate
Boc: tert-butoxycarbonyl
Me, OMe: methyl, methoxy
Et, OEt: ethyl, ethoxy
Pr, iPr: n-propyl, isopropyl
Bu, iBu, tBu: butyl, isobutyl, tert-butyl
THP: 2-tetrahydropyranyl
BOP: 1-benzotriazolyloxytris(dimethylamino) phosphonium hexafluorophosphate
Lawesson's reagent: 2,4-bis(4-methoxyphenyl)-1,3-dithia-2,4-diphosphetane-2,4-disulfide
bp: boiling point
mp: melting point
RT: room temperature
NMR: nuclear magnetic resonance
s: singlet
bs: broad singlet
d: doublet
t: triplet
q: quartet
unres.: unresolved peak
mt: multiplet
dt: doubled triplet
dd: doubled doublet.

Another subject of the present invention is a process for the preparation of the compounds according to the invention and of the possible salts thereof, wherein:

1) a compound of formula:

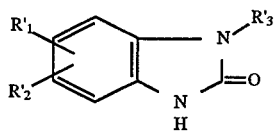 (II)

in which R'$_1$, R'$_2$ and R'$_3$ represent, respectively, either R$_1$, R$_2$ and R$_3$ as defined for (I), or precursor groups of R$_1$, R$_2$ and R$_3$, is reacted with a benzyl halide of formula:

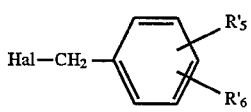 (III)

in which Hal represents a halogen atom, preferably chlorine or bromine, and R'$_5$ and R'$_6$ represent, respetively, either R$_5$ and R$_6$ as defined above for (I), or precursor groups of R$_5$ and R$_6$; and 2) either, when R'$_1$=R$_1$, R'$_2$=R$_2$, R'$_3$=R$_3$, R'$_5$=R$_5$ and R'$_6$=R$_6$, the compound of formula (I) thus obtained is isolated;

3) or, when any one of the groups R'$_1$, R'$_2$, R'$_3$, R'$_5$ and/or R'$_6$ represents, respectively, a precursor group of R$_1$, R$_2$, R$_3$, R$_5$ and/or R$_6$ the compound obtained in Step 1 is subjected to a subsequent treatment in order to prepare the compound of formula (I) by conversion of any one of the groups R'$_1$, R'$_2$, R'$_3$, R'$_5$ and/or R'$_6$ into R$_1$, R$_2$, R$_3$, R$_5$ and/or R$_6$ respectively;

4) optionally, the compound obtained in Step 2) or in Step 3) is converted into one of the salts thereof.

Compound (I') refers to a compound bearing a substituent R'$_1$, R'$_2$, R'$_3$, R'$_5$ and/or R'$_6$ which are precursors of R$_1$, R$_2$, R$_3$, R$_5$ and/or R$_6$.

Conversion of a substituent R'$_1$, R'$_2$, R'$_3$, R'$_5$ and/or R'$_6$ into R$_1$, R$_2$, R$_3$, R$_5$ and/or R$_6$ respectively may be carried out either starting with the compound of formula (I') or starting with one of the useful intermediate compounds in the preparation of (I).

The reaction of Step 1) is carried out in an anhydrous solvent such as DMF or THF, in the presence of a metal hydride such as sodium hydride for example, or in the presence of an alkoxide such as potassium tert-butoxide.

The benzimidazol-2-one derivatives (II) are known or may be prepared according to various procedures by known methods.

N-substituted benzimidazol-2-one derivatives (II), which are useful as starting materials for the preparation of the compounds according to the invention, may be prepared according to the processes described in patents GB 2,127,408, GB 1,575,386; patent applications JP 62-249,982, JP 53-009,770, JP 51-131,875; patents BE 770,911, BE 859,415, BE 830,403; patent applications EP 477,819, EP 454,330, EP 526,434.

Similarly, the following publications describe N-substituted benzimidazol-2-one derivatives:

Monatsh. Chem., 1985, 116 (5), 639–644.

Eur. J. Med. Chem.—Chim. Ther., 1983, 18 (6), 495–500.

N-Substituted benzimidazol-2-one derivatives may also be prepared by methods such as those described in the following publications:

Pharmazie, 1979, 34 (9), 576.

Pol. J. Chem., 1979, 53 (9), 1883–1887.

J. Heterocycl. Chem., 1970, 7 (4), 807–813.

Eur. J. Med. Chem.—Chim. Ther., 1981, 16 (4), 321–326.

According to one particular embodiment, the benzimidazol-2-ones may be prepared according to the process described in Eur. J. Med. Chem.—Chim. Ther., 1981, 16 (4), 321–326, in the following way.

Reaction in alcoholic solution, in the presence or absence of a base such as triethylamine, at room temperature or at reflux, of a primary amine of formula:

 (IV)

with substituted ortho-dinitro- or ortho-chloronitrobenzenes (V) of formulae:

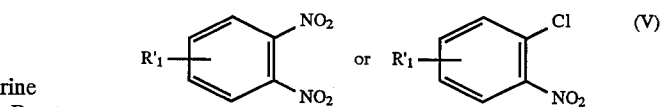 (V)

in which R'$_1$ is other than a nitro group, gives the N-substituted 2-nitroanilines of formula:

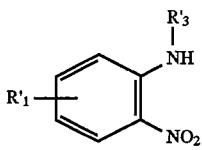

The compounds (VI) may also be obtained by heating the compounds (IV) and (V) in 2-ethoxyethanol (J. Chem. Soc. 1960, 314–318) or in ethylene glycol in the presence of sodium acetate or in 1,2,3,4-tetramethylbenzene or in Decalin®.

The compounds (VI) in which $R'_1$ is a group $(C_1-C_7)$ alkoxy, $(C_3-C_7)$cycloalkyloxy, $(C_3-C_7)$cycloalkylmethoxy, phenoxy, benzyloxy or (ω-methoxy$(C_2-C_7)$alkoxy are obtained by reacting a compound (VI), in which the substituent $R'_1$ is a chlorine atom, with a sodium alkoxide according to the process described in J. Org. Chem. 1963, 28, 3117 or with a sodium alkoxide in the presence of a phase transfer catalyst such as tris[2-(2-methoxyethoxy)ethyl]amine (TDA-1).

The compounds (VI) in which $R'_3$ is a group $(C_1-C_8)$alkyl substituted with a $(C_1-C_4)$alkoxy may be prepared by reacting a compound (VI), in which the substituent $R'_3$ is a $(C_1-C_8)$alkyl substituted with a hydroxyl, with a halo $(C_1-C_4)$alkyl, in the presence of a metal hydride such as sodium hydride for example, in an anhydrous solvent such as DMF or THF.

The compounds of formula (VI) are reduced into N-substituted ortho-phenylenediamines of formula (VII):

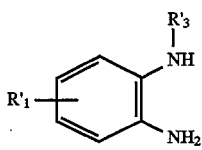

The reduction may be catalytic, for example using palladium-on-charcoal or Raney nickel®, or chemical, using iron, zinc or tin under acidic conditions (J. Chem. Soc. 1960, 314).

On reaction with ethyl chloroformate or methyl chloroformate in a solvent such as chloroform or dichloromethane, in the presence or absence of a base such as triethylamine, or in a DMF/water mixture in the presence of potassium carbonate, the compounds of formula (VII) give the compounds of formula (VIII) and/or (VIII'):

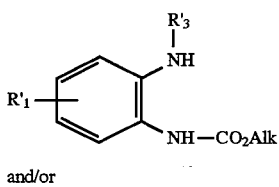

and/or

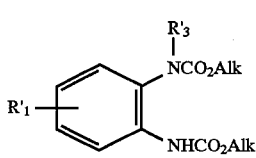

in which Alk represents ethyl or methyl.

The compounds of formula (VIII) and/or (VIII') are cyclized into benzimidazol-2-one (IX) by heating with sodium ethoxide.

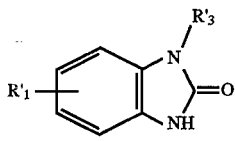

The compounds (IX) may also be obtained by reacting a compound of formula (VII) with urea according to the process described in J. Chem. Soc. 1960, 314 or with 1,1'-carbonyldiimidazole according to a process described in European Patent 92,391.

The compounds of formula (II) bearing certain substituents $R'_1$, $R'_2$ on their benzene part are used as precursors for the preparation of compounds of formula (II) bearing other substituents $R'_1$, $R'_2$. For example, the compounds (II) in which $R'_1$ and/or $R'_2$=H may be nitrated by standard reagents. The compound (II) in which $R'_1$ is an amino group may be prepared by catalytic hydrogenation, starting with a compound (II) in which $R'_1$ is a nitro group and $R'_2$ is hydrogen.

In the particular case where $R'_3$ represents a 3-azetidinyl, a 4-piperidyl, a 1-piperazinyl or a group —$(CH_2)_p$-3-azetidinyl, —$(CH_2)_p$-4-piperidyl or —$(CH_2)_p$-1-piperazinyl in which the nitrogen atom is substituted with $R_{11}$=a $(C_1-C_7)$alkylcarbonyl, a benzoyl, a $(C_1-C_7)$alkoxycarbonyl, a phenoxycarbonyl or a carbamoyl which is unsubstituted or substituted with one or two $(C_1-C_7)$alkyls, substitution on the nitrogen atom may be performed either on the benzimidazol-2-one compound (II) or on the final compound (I), starting with a compound in which the nitrogen atom is not substituted ($R_{11}$=H). Thus, when the nitrogen atom is substituted with $R_{11}$=a $(C_1-C_7)$alkylcarbonyl or a benzoyl, an acid chloride or an anhydride is reacted with a compound (II) or a compound (I) in which the nitrogen atom of the heterocyclic radical as defined above is not substituted ($R_{11}$=H). When the nitrogen atom is substituted with $R_{11}$=a $(C_1-C_7)$alkoxycarbonyl or a phenoxycarbonyl, the appropriate chloroformate is reacted with a compound (II) or a compound (I) in which $R_{11}$=H. On reacting ammonia with a compound of formula (II) or a compound of formula (I) in which $R_{11}$=phenoxycarbonyl, a compound (II) or a compound (I) in which $R_{11}$ is a carbamoyl is prepared; by reacting a $(C_1-C_7)$mono- or dialkylamine with such a compound, a compound of formula (II) or a compound of formula (I) in which $R_{11}$ is an N-$(C_1-C_7)$alkylcarbamoyl or N,N-di$(C_1-C_7)$alkylcarbamoyl is prepared. A compound (II) or a compound (I) in which $R_{11}$ is an N-alkylcarbamoyl may also be prepared by reacting an alkyl isocyanate with a compound (II) or a compound (I) in which $R_{11}$=H.

The compounds of formula (IV) are known or may 25 be prepared by known methods. For example, the variously substituted cyclohexylamines are prepared according to J. Org. Chem., 1962, 27, 3568–3572.

The benzyl halides of formula (III) are known or prepared by known methods.

For example, publications describing the following halomethylbenzene derivatives may be mentioned:

1,2,4- or 4,2,1- or 2,4,1-chloromethyl-methylmethoxybenzene: Bull. Soc. Chim., France, 1937, 4, 1092.

2-Chloromethyl-1,3-dimethoxybenzene: Chem. Listy, 1953, 47, 601–612.

1-Bromomethyl-2-methoxy-4-nitrobenzene: Sci. Sinica (Peking), 1962, 11, 483–498.

1-Bromomethyl-2-methyl-4-nitrobenzene: Pharmazie, 1969, 24 (1), 29–32.

1-Bromomethyl-2-methoxy-4-nitrobenzene: Bull. Soc. Chim., France, 1962, 2255.

1-Bromomethyl-4-methoxy-2-nitrobenzene: Zh. Obshch. Khim., 1963, 33 (8), 2792–2793.

Methyl 4-bromomethyl-3-methoxybenzoate: European patent application EP 179,619.

Ethyl 2-bromomethyl-6-methoxybenzoate: J. Org. Chem., 1983, 48, 3439–3444.

Methyl 4-bromomethyl-2-methoxybenzoate: Bull. Soc. Chim., France, 1962, 2255.

1-Bromomethyl-4-cyano-2-methoxybenzene, 4-bromomethylbenzenesulfonyl chloride: J. Med. Chem., 1990, 33, 2437–2451.

In general, the halomethylbenzene derivatives may be prepared by reacting N-bromosuccinimide with the corresponding methylbenzene derivatives. The reaction is carried out in a solvent such as carbon tetrachloride in the presence of dibenzoyl peroxide. A halomethylbenzene derivative may also be prepared from a corresponding hydroxymethylbenzene derivative, by the action of phosphorus tribromide in ether.

According to another process, the halomethylbenzene derivatives of formula (III) may be prepared from the corresponding alcohol by the action of thionyl chloride in order to prepare a methylbenzene chloride.

Conversion of a compound (I') into a compound (I) is carried out using methods known to those skilled in the art.

The preparation of compounds of formula (I) bearing substituents $R_1$, $R_3$, $R_5$ and/or $R_6$ is outlined in the description which follows; the same methods are applied, where appropriate, to the preparation of compounds in which the substituent $R_5$ has the value indicated for $R_6$.

The compounds (I) in which $R_1$ and/or $R_6$ is a hydroxyl may be obtained by catalytic hydrogenation, for example in the presence of palladium-on-charcoal, of a compound of formula (I') in which $R'_1$ and/or $R'_6$ is a benzyloxy. These compounds may also be prepared from similar compounds of formula (I') in which $R'_1$ and/or $R'_6$ represents an amino group, using the method described in J. Org. Chem., 1977 42, 2053.

The compounds of formula (I) in which $R_1$ and/or $R_6$ represents a $C_1$–$C_7$alkoxy may be prepared directly by the process according to the invention, starting with appropriately substituted compounds of formulae (II) and (III).

The compounds (I') in which $R'_1$ and/or $R'_6$ represents a hydroxyl also make it possible to prepare compounds (I) in which $R_1$ and/or $R_6$ is a $C_1$–$C_7$alkoxy, by the action of a $C_1$–$C_7$alkyl halide in the presence of a base such as a metal hydride or an alkali metal or alkaline-earth metal carbonate such as $K_2CO_3$ or $Cs_2CO_3$ in a solvent such as THF or DMF. Similarly, the compounds of formula (I) in which $R_6$ represents an ω-aminoalkyloxy may be prepared by reacting an ω-chloro($C_2$–$C_7$)alkylamine with the compounds in which $R'_6$=OH; similarly, the compounds in which $R_1$ and/or $R_6$ represents an ω-hydroxy($C_2$–$C_7$)alkyloxy may be prepared by the action of a chloro($C_2$–$C_7$)alkanol; in the particular case of the preparation of a compound (I) in which $R_1$ and/or $R_6$=O($CH_2$)$_2$OH, it is also possible to react ethylene carbonate with a compound (I') in which $R'_1$ and/or $R'_6$=OH.

The halo($C_2$–$C_7$)alkyloxybenzyl halides (III, $R'_6$=ω-halo ($C_2$–$C_7$)alkyloxy) may be used for the preparation of compounds according to the invention in which the substituent $R_6$ is an ω-amino($C_2$–$C_7$)alkyloxy which is unsubstituted or substituted with one or two alkyls, according to the following scheme:

in which Alk' represents a $C_2$–$C_7$alkyl.

Compounds of formula (I) in which $R_6$ represents a ($C_1$–$C_7$)alkylcarbonyloxy or a benzoyloxy are obtained by reacting an acid halide or an anhydride with a compound (I') in which $R'_6$ is a hydroxyl.

The compounds of formula (I) in which $R_6$ is a group —$OR_{14}$, $R_{14}$ representing an ω-carbamoyl($C_1$–$C_7$)alkyl which is free or substituted with one or two $C_1$–$C_7$alkyls, may be prepared from a compound (I') in which $R'_6$ represents a group —$OR_{14}$, $R_{14}$ representing an ω-carboxy($C_1$–$C_7$)alkyl esterified with a $C_1$–$C_4$alkyl. This preparation is carried out in a manner which is conventional for those skilled in the art, by the action of an appropriately selected amine.

A compound of formula (I') in which $R'_6$ is a nitro group makes it possible to obtain by catalytic hydrogenation, for example in the presence of platinum oxide or Raney nickel®, or by chemical reduction, for example in the presence of tin or iron in acidic medium, a compound (I) in which $R_6$ is an amino group; other compounds in which the amino group is substituted may then be prepared using reactions that are well known to those skilled in the art.

In order to prepare the compounds of formula (I) in which $R_1$ and/or $R_6$ represents a ($C_1$–$C_7$)monoalkylamino, a compound of formula (I') in which $R'_1$ and/or $R'_6$ represents an amino group is reacted with an aldehyde or a ketone, in acidic medium, in the presence of a reducing agent such as sodium cyanoborohydride; the compounds (I) in which $R_1$ and/or $R_6$ represents a dialkylamino are prepared via an identical reaction.

The compounds of formula (I) in which $R_6$ represents a group —$NR_{12}R_{13}$, in which $R_{13}$ represents a benzyl which may itself be substituted, may be prepared by reacting an optionally substituted benzyl chloride with a compound of formula (I') in which $R'_6$ is a group —$NHR_{12}$.

In order to prepare the compounds of formula (I) in which $R_6$ represents an amino group substituted with a ($C_3$–$C_7$) cycloalkylmethyl or an optionally substituted phenethyl respectively, a compound of formula (I'), in which $R'_6$ represents an amino group, is reacted with a ($C_3$–$C_7$) cycloalkylcarboxaldehyde or an optionally substituted phenylacetaldehyde respectively, in acidic medium, in the presence of a reducing agent such as sodium cyanoborohydride.

In order to prepare the compounds of formula (I) in which $R_6$ represents an amino group substituted with a ($C_3$–$C_8$) alkenyl, a compound of formula (I'), in which $R'_6$ represents an amino or ($C_1$–$C_7$)alkylamino group, is reacted with a $C_3$–$C_8$alkenyl chloride.

The compounds of formula (I) in which $R_6$ represents a group Δ3-pyrrolin-1-yl are prepared by reacting, in an inert atmosphere, cis-1,4-dichloro-2-butene with the compounds of formula (I') in which $R'_6$ is an amino group in the presence of a base such as triethylamine. The compounds of formula (I) in which $R_6$ is a 1-pyrrolidinyl group are prepared by hydrogenation. The reaction of cis-1,4-dichloro-2-butene with the compounds (I'), in which $R'_6$ is an amino group, may also be carried out in air in the presence of a base such as sodium carbonate and leads, under these conditions, to the formation of a mixture of a compound of formula (I) in which $R_6$ represents a group Δ3-pyrrolin-1-yl and a compound of formula (I) in which $R_6$ represents a 1-pyrrolyl group, which may be separated by chromatography.

A compound of formula (I) in which $R_6$ represents a 1-pyrrolyl group may also be prepared by reacting a compound of formula (I), in which $R_6$ represents a group Δ3-pyrrolin-1-yl, with perbenzoic acid, which is itself prepared by reacting hydrogen peroxide with benzoyl chloride.

The compounds of formula (I) in which $R_6$ represents a 2-isoindolinyl group are prepared by reacting α,α'-dibromoo-xylene with the compounds of formula (I') in which $R'_6$ is an amino group, in the presence of a base such as triethylamine, and in a solvent such as refluxing dimethylformamide.

The compounds of formula (I) in which $R_6$ represents a 1-methyl-2,4-dioxo-3-imidazolinyl group are prepared in two steps: sarcosine is reacted with a compound of formula (I') in which $R'_6$ represents a phenoxycarboxamido, in the presence of a base such as triethylamine, to give a compound of formula (I') in which $R'_6$ represents an N'-carboxymethyl-N'-methylureido, and on heating to 100° C., under vacuum, the product obtained above then cyclizes.

When $R'_6$ represents an amino group, a nitrosation may also be carried out, for example in the presence of nitrous acid or sodium nitrite, in order to prepare a compound (I') in which $R'_6$ represents a diazonium salt; by reactions known to those skilled in the art, access is then gained to the compounds (I) according to the invention in which $R_6$ is a cyano, a halo or a $C_1$–$C_7$alkylthio.

The compounds of formula (I) in which $R_6$ represents a group —$CH_2NH_2$ are prepared from similar compounds of formula (I') in which $R'_6$ represents a cyano group, according to the method described in J. Med. Chem., 1990 33, 2437–2451. Starting with these compounds, the compounds of formula (I) in which $R_6$ represents a group —$CH_2NR_7R_8$, $R_8$ and/or $R_7$ being other than hydrogen, are prepared according to methods known to those skilled in the art.

The compounds (I) in which $R_6$ represents a group —$NR_{12}R_{13}$, $R_{13}$ being a ($C_1$–$C_7$)alkylcarbonyl, a ($C_3$–$C_7$) cycloalkylcarbonyl, an optionally substituted benzoyl, a phenacetyl in which the benzene ring is optionally substituted, a pyridylcarbonyl, a methylpyridylcarbonyl, a thienylcarbonyl, a furylcarbonyl or a 4-piperidylcarbonyl are obtained by reacting the appropriate anhydride or the appropriate acid chloride with a compound (I') in which $R'_6$ is a group $R_{12}NH$—, in the presence of an amine such as triethylamine.

The compounds (I) in which $R_6$ represents a group —$NR_{12}R_{13}$, $R_{13}$ being a ($C_1$–$C_7$)alkoxycarbonyl or a phenoxycarbonyl or benzyloxycarbonyl respectively, are obtained by reacting a $C_1$–$C_7$alkylchloroformate, or phenyl or benzyl chloroformate respectively, with a compound (I') in which $R'_6$ is a group $R_{12}NH$—. Similarly, by reacting a phenoxythiocarbonyl chloride with a compound of formula (I') in which $R'_6$ represents a group $R_{12}NH$—, a compound of formula (I) in which $R_6$ is a group —$NR_{12}R_{13}$, in which $R_{13}$ represents a phenoxythiocarbonyl, is obtained.

By reacting ammonia with a compound of formula (I') in which $R'_6$ is a group —$NR_{12}R_{13}$, in which $R_{13}$ represents a phenoxycarbonyl or a phenoxythiocarbonyl, a compound of formula (I), in which $R_6$ is a group —$N(R_{12})CONH_2$ or —$N(R_{12})CSNH_2$, is prepared.

It is also possible to prepare compounds of formula (I) in which $R_6$ is a ureido (—$NR_{12}CONR_{22}R_{23}$) or a thioureido (—$NR_{12}CSNR_{22}R_{23}$) respectively by reacting a compound $NHR_{22}R_{23}$ with a compound of (I') in which $R'_6$ is a group —$NR_{12}R_{13}$, in which $R_{13}$ represents a phenoxycarbonyl or phenoxythiocarbonyl respectively.

It is also possible to prepare compounds of formula (I) in which $R_6$ is a ureido (—$NR_{12}CONR_{22}R_{23}$) or a thioureido (—$NR_{12}CSNR_{22}R_{23}$) respectively by reacting a carbamoyl chloride (ClCONR$_{22}$R$_{23}$) or a thiocarbamoyl chloride (ClCSNR$_{22}$R$_{23}$) respectively with a compound of formula (I') in which $R'_6$ is a group $R_{12}NH$—.

It is also possible to prepare a compound (I) in which $R_6$ is a group —$NR_{12}R_{13}$ in which $R_{13}$ represents a ($C_1$–$C_7$) alkylcarbamoyl by reacting a $C_1$–$C_7$alkyl isocyanate with a compound (I') in which $R'_6$ is a group $R_{12}NH$—.

It is also possible to prepare a compound (I) in which $R_6$ is a thioureido by reacting Lawesson's reagent with a compound (I') in which $R'_6$ is the corresponding ureido.

In order to prepare a compound of formula (I) in which $R_6$ represents a group —$NR_{12}CO$—($C_2$–$C_7$)alkyl-$NR_7R_8$, a halo($C_3$–$C_8$)acyl halide, such as 3-chloropropionyl chloride or 4-chlorobutyryl chloride for example, is reacted with a compound of formula (I') in which $R'_6$ is a group —$NHR_{12}$, in the presence of a base such as triethylamine; on reaction of the compound obtained with an amine $HNR_7R_8$, the compound of formula (I) denoted above is then obtained.

Similarly, by reacting an ω-benzyloxy ($C_1$–$C_7$) alkylcarbonyl halide with a compound of formula (I') in which $R'_6$ represents a group —$NHR_{12}$, a compound of formula (I) is prepared in which $R_6$ represents a group —$NR_{12}CO(C_1$–$C_7$)alkyl-O—$CH_2$—$C_6H_5$. On hydrogenation of the above compound, in the presence of a catalyst such as, for example, palladium-on-charcoal, a compound of formula (I) in which $R_6$ is a group —$NR_{12}CO$—($C_1$–$C_7$) alkyl-OH is obtained.

Likewise, the acid chloride $R_7R_8NCR_{17}R_{18}COCl$ is reacted with a compound of formula (I') in which $R'_6$ is a group —$NHR_{12}$, in order to prepare a compound of formula (I) in which $R_6$ is a group —$NR_{12}COCR_{17}R_{18}NR_7R_8$.

The action of an anhydride, such as succinic anhydride or glutaric anhydride, may be used on a compound (I') in which $R'_6$ is a group —$NHR_{12}$, in order to prepare a compound (I) in which $R_6$ is a group —$NR_{12}CO(CH_2)_2CO_2H$ or —$NR_{12}CO(CH_2)_3CO_2H$. Where appropriate, the acid thus obtained is converted into an ester or an amide.

It is also possible to use the action of ethyloxalyl chloride on a compound (I') in which $R'_6$ is a group —$NHR_{12}$, in order to prepare a compound (I) in which $R_6$ is a group —$NR_{12}COCO_2Et$.

The compounds (I) in which $R_6$ represents a group —$NR_{12}$ substituted with a group —($CH_2$)$_r$—$COR_{19}$ are obtained by reacting a compound of formula $Hal(CH_2)_r$COOR, in which Hal represents a halogen, for example bromine, and R represents a $C_1$–$C_7$alkyl, with a compound (I') in which $R'_6$ is a group —$NHR_{12}$, in the presence of cuprous chloride; where appropriate, the ester thus obtained is converted into an acid or an amide.

Similarly, the compounds of formula (I) in which $R_6$ is a group —$NR_{12}$ substituted with a group —$CR_{17}R_{18}COR_{19}$ are prepared by reacting a compound of formula Hal—$CR_{17}R_{18}COR_{19}$ with the corresponding compounds (I') in which the substituent $R'_6$ is a group —$NHR_{12}$.

The compounds (I) in which $R_6$ represents a ($C_1$–$C_7$) alkylsulfonamido or, respectively, a group —$NHSO_2$—Ar, a group —$NH$—$SO_2$—$CH_2$—Ar or a dimethylaminosulfonamido are obtained by reacting an alkylsulfonyl halide, in which the alkyl is $C_1$–$C_7$, or respectively by reacting a compound Ar—$SO_2Cl$, a compound Ar—$CH_2$—$SO_2Cl$ or a dimethylsulfamoyl halide, with a compound (I') in which $R'_6$ is an amino group.

The compounds (I) in which $R_6$ is a guanidino group which is unsubstituted or substituted once or twice with a $C_1$–$C_7$alkyl, a phenyl or a benzyl, may be prepared from compounds (I') in which $R'_6$ is a phenoxycarboxamido group by the action of cyanamide or one of the derivatives thereof which is appropriately substituted on the nitrogen.

The compounds (I) in which $R_6$ is a guanidino group substituted in position 2 with a cyano are prepared in two steps: dimethyl N-cyanodithioiminocarbonate is reacted with a compound (I') in which $R'_6$ is an amino, in a solvent such as refluxing n-butanol, to give a compound (I') in which $R'_6$ is a group —$NHC(SCH_3)$=N—CN; on reaction of the above compound with a suitable amine, the expected compound (I) is then obtained.

The compounds of formula (I) in which $R_6$ represents a $(C_1-C_7)$alkoxycarbonyl may be prepared directly from the halide of formula (III) bearing the same substituent by the process according to the invention. By methods known to those skilled in the art, they allow the compounds of formula (I), in which $R_6$ is a carboxyl group, to be obtained.

According to another procedure, the compounds of formula (I) in which $R_6$ is a benzyloxycarbonyl make it possible, by catalytic hydrogenation, to obtain the compounds (I) in which $R_6$ is a carboxyl. Reaction with a thionyl halide gives the compounds of formula (I') in which $R'_6$ is a halocarbonyl. Starting with such compounds, compounds of formula (I) in which $R_6$ is a carbamoyl substituted with $R_{15}$ and $R_{16}$ are prepared by reaction with a compound $HNR_{15}R_{16}$.

It is also possible to use the compounds of formula (I') in which $R'_6$ represents a phenoxycarbonyl in order to obtain the compounds of formula (I) in which $R_6$ is a phenylcarbamoyl or a $(C_1-C_7)$alkylcarbamoyl by reacting with an aniline or a $(C_1-C_7)$alkylamine. An aniline substituted on the phenyl or, respectively, an alkylamine substituted on the alkyl with $R_{24}$ make it possible to obtain compounds of formula (I) in which $R_6$ is a phenylcarbamoyl substituted on the phenyl or, respectively, an alkylcarbamoyl substituted on the alkyl with $R_{24}$.

The compounds of formula (I') in which $R'_6$ is a carboxyl may be used in order to prepare the compounds of formula (I) in which $R_6$ is a group —$CONR_{15}R_{16}$, by reacting with a compound of formula $HNR_{15}R_{16}$, in the presence of BOP and a base such as diisopropylethylamine.

The compounds of formula (I) in which $R_6$ is a group —$COR_{25}$ may also be obtained from compounds (I') in which $R'_6$ is a phenoxycarbonyl, by reacting with a compound $R_{25}H$.

The compounds of formula (I) in which $R_6$ is a sulfamoyl substituted with $R_{20}$ and $R_{21}$, are obtained by reacting a compound $HNR_{20}R_{21}$ with a compound of formula (I') in which $R'_6$ represents a halosulfonyl group.

A compound (I) in which $R_6$ is a thiocarbamoyl may be prepared by reacting Lawesson's reagent with a compound (I) in which $R_6$ is the corresponding carbamoyl.

The compounds of formula (I) in which $R_6$ is a group —$CONHCR_{17}R_{18}COR_{19}$ are prepared from compounds of formula (I') in which $R'_6$ represents either a group —COCl or a group phenoxycarbonyl, by reacting with $H_2NCR_{17}R_{18}COR_{19}$. They may also be prepared from compounds of formula (I') in which $R'_6$ is a carboxyl, by reacting with a compound $H_2NCR_{17}R_{18}COR_{19}$ in the presence of BOP and an amine such as diisopropylethylamine.

The affinity of the compounds according to the invention for the vasopressin receptors has been determined in vitro using the method described in C. J. Lynch et al., J. Biol. Chem., 1985, 260 (5), 2844–2851. This method consists in studying the displacement of tritiated vasopressin bound to the $V_1$ sites of rat liver membranes. The 50% inhibitory concentrations ($IC_{50}$) for the binding of tritiated vasopressin of the compounds according to the invention are low, ranging up to $10^{-6}$M.

The affinity of the compounds (I) according to the invention for the $V_2$ receptors was measured on a bovine kidney membrane preparation according to a method adapted from P. Crause et al., Molecular and Cellular Endocrinology, 1982, 28, 529–541 and from F. L. Stassen et al., J. Pharmacol. Exp. Ther., 1982, 225, 50–54. The compounds according to the invention inhibit the binding of tritiated arginine-vasopressin to the receptors in the membrane preparation. The $IC_{50}$ values for the compounds according to the invention are low, ranging up to $10^{-9}$M.

The antagonist activity of the $V_2$ receptors of the compounds according to the invention was studied by the test for assaying adenylate cyclase activity carried out according to a method adapted from M. Laburthe et al., Molecular Pharmacol., 1986, 29, 23–27. A bovine kidney membrane preparation is used and each product is incubated for 10 minutes at 37° C., alone or in the presence of AVP (arginine-vasopressin) at a concentration of $3.10^{-8}$M. The cyclic AMP (cyclic adenosine monophosphate) produced is measured by radioimmunological assay. The concentration inhibiting the stimulation of adenylate cyclase induced by $3.10^{-8}$M AVP by 50% ($IC_{50}$) is determined. The $IC_{50}$ values determined are low, ranging up to $10^{-8}$M.

The agonist or antagonist activity of the vasopressin receptors of the compounds according to the invention, administered orally, is evaluated in rats (OFA strain or Sprague-Dawley strain) subjected to water overload, treated with vasopressin. The antagonist activity of the compounds according to the invention was also evaluated in rats given water normally (OFA strain or Sprague-Dawley strain) according to the technique described in Br. J. Pharmacol., 1992, 105, 787–791. The diuretic effect was observed for some compounds at a dose of 10 mg/kg.

Similarly, the affinity of the compounds (I) according to the invention for the oxytocin receptors has been determined in vitro by displacement of a radioiodo oxytocin analog bound to the receptors of a membrane preparation from the mammary glands of gestating rats, according to a technique similar to that described by J. Eland et al. in Eur. J. Pharmacol., 1987, 147, 197–207. The $IC_{50}$ values of the compounds according to the invention reach $10^{-6}$M.

The compounds according to the invention are active after administration via various routes, especially via the oral route.

No sign of toxicity is observed with these compounds at pharmaceutically active doses.

Thus, the compounds according to the invention may be used in the treatment or prevention of various vasopressin-dependent or oxytocin-dependent complaints, cardiovascular complaints, such as hypertension, pulmonary hypertension, cardiac insufficiency, myocardial infarction, or coronary vasospasm, in particular in smokers, unstable angina and PTCA (percutaneous transluminal coronary angioplasty), cardiac ischemia, deregulation of hemostasis and especially hemophilia, von Willebrand's syndrome; central nervous system complaints, migraine, cerebral vasospasm, cerebral hemorrhaging, cerebral edemas, depression, anxiety, psychotic states and memory disorders for example; renal system complaints such as edemas, renal vasospasm, necrosis of the renal cortex, hyponatremia, hypokalemia, Schwartz-Bartter syndrome; complaints of the gastric system, such as gastric vasospasm, cirrhosis of the liver, ulcers, vomiting pathology, for example nausea including nausea due to chemotherapy, travel sickness or alternatively antidiuretic hormone inappropriate secretion syndrome (ADHIS), diabetes insipidus and enuresis. The compounds according to the invention may also be used in the treatment of sexual behavior disorders. In women, the compounds according to the invention may be used for treating dysmenorrhea or premature labor. The compounds according to the invention may also be used in the treatment of small-cell pulmonary cancers, hyponatremic encephalopathies, Raynaud's disease, pulmonary syndrome, glaucoma, cataract and in post-operative treatments, especially after abdominal surgery.

The subject of the present invention is also pharmaceutical compositions containing an effective dose of a compound according to the invention or of a pharmaceutically acceptable salt thereof, and suitable excipients.

Said excipients are chosen depending on the desired mode of administration and pharmaceutical form.

In the pharmaceutical compositions of the present invention for oral, sublingual, inhaled, subcutaneous, intramuscular, intravenous, topical, intratracheal, intranasal, transdermal or rectal administration, the active principles of formula (I) above, or the possible salts thereof, may be administered in unit forms of administration, as a mixture with standard pharmaceutical supports, to animals and to humans for the prophylaxis or treatment of the above disorders or diseases. Suitable unit forms of administration comprise oral route forms such as oral suspensions or solutions, granules, powders, gelatin capsules and tablets, sublingual, buccal, intratracheal and intranasal forms of administration, aerosols, implants, subcutaneous, intramuscular or intravenous forms of administration and rectal forms of administration. For topical application, the compounds according to the invention may be used in creams, ointments or lotions.

In order to obtain the desired prophylactic or therapeutic effect, the dose of active principle may range between 0.01 and 50 mg per kg of body weight and per day.

Each unit dose may contain from 0.5 to 1000 mg, preferably from 1 to 500 mg, of active ingredients in combination with a pharmaceutical support. This unit dose may be administered 1 to 5 times per day so as to administer a daily dose of from 0.5 to 5000 mg, preferably from 1 to 2500 mg.

When a solid composition is prepared in the form of tablets, the main active ingredient is mixed with a pharmaceutical vehicle such as silica, gelatin, starch, lactose, magnesium stearate, talc, gum arabic or the like. The tablets may be coated with sucrose, a cellulose derivative or other suitable materials or alternatively they may be treated such that they have a prolonged or delayed activity and such that they continuously release a predetermined amount of active principle.

A preparation as gelatin capsules is obtained by mixing the active ingredient with a diluent such as a glycol or a glycerol ester and by incorporating the mixture obtained in soft or hard gelatin capsules.

A preparation in the form of a syrup or an elixir or for administration in the form of drops may contain the active ingredient together with a sweetener, preferably a calorie-free sweetener, methylparaben and propylparaben as antiseptic agent, as well as a flavoring agent and a suitable dye.

The water-dispersible powders or granules may contain the active ingredient as a mixture with dispersing agents or wetting agents or suspending agents, such as polyvinylpyrrolidone, as well as with sweeteners or flavor modifiers.

For rectal administration, use is made of suppositories which are prepared with binders that melt at rectal temperature, for example cocoa butter or polyethylene glycols.

For parenteral administration, use is made of aqueous suspensions, isotonic saline solutions or sterile and injectable solutions which contain pharmacologically compatible wetting agents and/or dispersing agents, for example propylene glycol, polyethylene glycol or butylene glycol.

For administration by inhalation an aerosol additionally containing, for example, sorbitan trioleate or oleic acid and trichlorofluoromethane, dichlorofluoromethane, dichlorotetrafluoroethane, or any other biologically compatible propellent gas is used; a system containing the active principle, alone or combined with an excipient, in powder form, may also be used.

The active principle may also be formulated in the form of microcapsules, optionally with one or more supports or additives.

The compositions of the present invention may contain, besides the products of formula (I) above or the pharmaceutically acceptable salts thereof, other active principles which may be useful in the treatment of the disorders or diseases mentioned above.

Thus, the subject of the present invention is also pharmaceutical compositions containing several active principles in combination, one of which is a compound according to the invention.

Thus, according to the present invention, pharmaceutical compositions containing a compound according to the invention combined with a compound acting on the renin-angiotensin system, such as an inhibitor of the conversion enzyme, an angiotensin II antagonist or a renin inhibitor may be prepared. It is also possible to combine a compound according to the invention, for example, with a peripheral vasodilator, a calcium inhibitor, a beta-blocker, an alpha-1-blocker or a diuretic agent. Such compositions will be useful in particular in the treatment of hypertension or heart failure.

It is also possible to combine two compounds according to the invention: an antagonist specific for the $V_1$ receptor to an antagonist specific for the $V_2$ receptor or alternatively an antagonist specific for the $V_1$ receptor to an antagonist specific for oxytocin.

The term antagonist specific for the $V_1$ receptor or for the $V_2$ receptor or respectively for oxytocin means a compound which has an affinity for the $V_1$ receptor, the $V_2$ receptor or oxytocin respectively which is appreciably greater (at least 10 times) than its affinity for the other two receptors.

These combinations make it possible to reinforce the therapeutic activities of the compounds according to the invention.

PREPARATIONS

Preparations of 1,3-dihydro-2H-benzimidazol-2-ones.

Preparation 1

5-Chloro-3-cyclohexyl-1,3-dihydro-2H-benzimidazol-2-one

A) 4-Chloro-2-cyclohexylamino-1-nitrobenzene

A mixture consisting of 19.4 g of 2,4-dichloro-1-nitrobenzene, 40 g of cyclohexylamine and 100 ml of 2-ethoxyethanol is maintained at reflux for 12 hours.

The solvent is evaporated off under vacuum and the residue is taken up in ethyl ether and washed with $H_2O$, dried over $Na_2SO_4$ and the solvent is evaporated off under vacuum. 11.7 g of the expected product are obtained after crystallization from iso ether, mp=125° C.

B) 4-Chloro-2-cyclohexylamino-1-aminobenzene 12 g of the compound obtained in Step A), 8 g of iron powder, 15 ml of water and 15 ml of ethanol are brought to reflux. 30 ml of concentrated hydrochloric acid in 20 ml of water and 20 ml of ethanol are then introduced dropwise over 30 minutes. The reaction medium is then maintained at reflux for 1 hour 30 minutes.

After cooling, the reaction medium is poured onto ice and saturated $NaHCO_3$ solution is added thereto. The mixture is extracted with EtOAc, washed with water and then with saturated $NaHCO_3$ solution, then with water, dried over $Na_2SO_4$ and the solvent is evaporated off under vacuum. The residue is chromatographed on silica using isopropyl ether as eluent. 9.4 g of the expected product are obtained, which product is used without further purification in the next step.

C) 5-Chloro-3-cyclohexyl-1,3-dihydro-2H-benzimidazol-2-one.

A mixture of 4.5 g of the compound obtained in Step B), 2.5 g of urea and 10 ml of 1,2,3,4-tetramethylbenzene is heated to 170°–180° C. for 90 minutes.

After cooling, the reaction medium is taken up in ethyl acetate. It is washed with water, dried over sodium sulfate and the solvent is evaporated off under vacuum. After crystallization from heptane and recrystallization from EtOAc, 3.5 g of the expected product are obtained, mp=213° C.

This compound may also be prepared according to Eur. J. Med. Chem.—Chimica Therapeutica, 1981, 16 (4), 321–326, mp=206°–208° C.

Preparation 2

3-Cyclohexyl-1,3-dihydro-5-methoxy-2H-benzimidazol-2-one

A) 2-Cyclohexylamino-4-methoxy-1-nitrobenzene.

Sodium methoxide solution is prepared by adding 0.5 g of sodium to 60 ml of MeOH. 5.1 g of the compound obtained in Preparation 1 Step A and 7.5 ml of tris[2-(2-methoxyethoxy)ethyl]amine are then successively added and the mixture is heated at reflux for 24 hours. The solvent is evaporated off under vacuum and the residue is taken up in water, extracted with DCM, washed with water, dried over $Na_2SO_4$ and evaporated under vacuum. 3.86 g of the expected product are obtained in the form of an oil which crystallizes, mp=78°–80° C.

B) 1-Amino-2-cyclohexylamino-4-methoxybenzene.

A mixture of 11.86 g of the compound obtained in the above step, 7.9 g of iron powder, 15 ml of water and 15 ml of EtOH is heated to reflux, followed by dropwise addition of a solution of 29.4 ml of concentrated hydrochloric acid in 20 ml of water and 20 ml of EtOH. The reaction mixture is left at reflux for 2 hours. After cooling, the reaction mixture is poured onto ice, saturated $NaHCO_3$ solution is added, the mixture is extracted with DCM and an insoluble gray material is filtered off on Celite. After allowing the filtrate to settle, the organic phase is washed with saturated $NaHCO_3$ solution, with water, dried over Na2SO4 and evaporated under vacuum. The residue is chromatographed on silica, eluting with a DCM/MeOH mixture (98/2; v/v). 7.5 g of the expected product are obtained in the form of a black oil which is used without further purification in the following step.

C) 3-Cyclohexyl-1,3-dihydro-5-methoxy-2H-benzimidazol-2-one.

A mixture of 7.5 g of the compound obtained in the above step, 4.1 g of urea and 20 ml of 1,2,3,4-tetramethylbenzene is heated at 170°–180° C. for 1 hour 30 minutes. After cooling, the mixture is extracted with EtOAc, washed with water, dried over $Na_2SO_4$ and evaporated under vacuum. The residue is taken up in hexane and the brown precipitate formed is drained off. The precipitate is chromatographed on silica, eluting with a DCM/EtOAc mixture (50/50; v/v). 2.76 g of the expected product are obtained after crystallization from EtOAc, mp=163°–165° C.

Preparation 3

3-Cyclohexyl-5-ethoxy-1,3-dihydro-2H-benzimidazol-2-one

A) 4-Ethoxy-1-nitro-2-cyclohexylaminobenzene.

Sodium ethoxide solution is prepared by adding 0.5 g of sodium to 60 ml of ethanol. 5.1 g of 4-chloro-2-cyclohexylamino-1-nitrobenzene described in Preparation 1 Step A are then added. Next, 7.5 ml of tris[2-(2-methoxyethoxy)ethyl]amine are added and the mixture is maintained at reflux for 3 hours. The solvent is evaporated off under vacuum and the residue is taken up in water, extracted with DCM, washed with water and dried over $Na_2SO_4$, and the solvent is evaporated off under vacuum. After chromatography on silica eluting with DCM, 4.26 g of the expected product are obtained in the form of a yellow oil which crystallized from iso ether, mp=80°–82° C.

B) 4-Ethoxy-1-amino-2-cyclohexylaminobenzene.

A mixture of 4.26 g of the compound obtained in Step A) and 2.7 g of iron powder in 5.1 ml of water and 5.1 ml of ethanol is maintained at reflux. A solution of 10 ml of concentrated HCl in 7 ml of water and 7 ml of ethanol is then added dropwise and the mixture is maintained at reflux for a further 2 hours. After cooling, the reaction mixture is poured onto ice and treated with saturated $NaHCO_3$ solution, extracted with DCM, and an insoluble gray material is filtered off on Celite. After settling of the organic phase, it is washed with water and dried over $Na_2SO_4$, and the solvent is evaporated off under vacuum. 3.05 g of a black oil are obtained, which product was used without further purification in the following step.

C) 3-Cyclohexyl-5-ethoxy-1,3-dihydro-2H-benzimidazol-2-one.

A mixture of 3.05 g of the oil obtained in Step B and 1.6 g of urea in 8 ml of 1,2,3,4-tetramethylbenzene is heated at 170°–180° C. for 1 hour 30 minutes. After cooling, the mixture is taken up in EtOAc, washed with water, dried over sodium sulfate and evaporated under vacuum. The residue is taken up in hexane and the brown precipitate formed is drained off. The precipitate is chromatographed on silica, eluting with a DCM/EtOAc mixture (50/50; v/v). 1.33 g of the expected product are obtained, which product was precipitated with isopropyl ether. mp=203° C.

Preparation 4

5-Chloro-3-cyclohexylmethyl-1,3-dihydro-2H-benzimidazol-2-one

A) 4-Chloro-1-nitro-2-[(cyclohexylmethyl)amino]benzene

To a solution of 8.1 g of 1,2-dinitro-4-chlorobenzene in 20 ml of 95% ethanol is added dropwise a solution of 13.6 g of cyclohexylmethylamine in 10 ml of 95% ethanol. The temperature rises to 50° C. The reaction medium is kept stirring for 2 hours and the solvent is then evaporated off under vacuum. The residue is taken up in DCM, washed with water, then with 2N hydrochloric acid and next with water, dried over $Na_2SO_4$ and the solvent is then evaporated off under vacuum. The residue is chromatographed on silica, eluting with isopropyl ether. After recrystallization from heptane, 4.21 g of the expected product are obtained, mp=73° C.

B) 4-Chloro-1-amino-2-[(cyclohexylmethyl)amino]benzene.

A solution of 21.5 g of the product obtained in Step A) and 13.4 g of iron powder in a mixture of 25 ml of water and 25 ml of ethanol is brought to reflux. A solution of 50 ml of concentrated hydrochloric acid in a mixture of 34 ml of water and 34 ml of ethanol is then added slowly. The mixture is maintained at reflux for 2 hours. The reaction medium is then run onto ice and is treated with saturated $NaHCO_3$ solution, then extracted with DCM, washed with water and dried over $Na_2SO_4$ and the solvent is evaporated off under vacuum. The residue is chromatographed on silica, eluting with DCM. After crystallization from heptane, 7.2 g of the expected product are obtained, mp=62° C.

C) 5-Chloro-3-cyclohexylmethyl-1,3-dihydro-2H-benzimidazol-2-one

A mixture of 7.2 g of the compound obtained in Step B) and 6.7 g of 1,1'-carbonyldiimidazole in 100 ml of acetonitrile is heated at reflux for 5 minutes. The solvent is evaporated off under vacuum and the residue is taken up in water, extracted with DCM, washed with saturated NaHCO$_3$ solution, dried over Na$_2$SO$_4$ and evaporated under vacuum. The residue is chromatographed on silica, eluting with a DCM/MeOH mixture (95/5; v/v). 5.6 g of the expected product are obtained, mp=173° C.

Preparation 5

5-Ethoxy-1,3-dihydro-3-(4(a,e)-methylcyclohexyl)-2H-benzimidazol-2-one

A) 4-Chloro-2-(4(a,e)-methylcyclohexyl)amino-1-nitrobenzene.

To a solution of 20 g of 4-chloro-1,2-dinitrobenzene in 80 ml of 95% EtOH are added dropwise 30 g of 4-methylcyclohexylamine (mixture of isomers) and the mixture is left stirring for 24 hours at RT. The reaction mixture is evaporated under vacuum, the residue is extracted with heptane and the solvent is evaporated off under vacuum. 25 g of the expected product are obtained in the form of a red oil, which product is used without further purification in the following step.

B) 4-Ethoxy-2-(4(a,e)-methylcyclohexyl)amino-1-nitrobenzene.

This compound is prepared according to the procedure described in Preparation 3 Step A, starting with 25 g of the compound obtained in the above step. 14 g of the expected product are obtained, mp=85° C.

C) 1-Amino-4-ethoxy-2-(4(a,e)-methylcyclohexyl)aminobenzene and 1-amino-4-ethoxy-2-(4(a)-methylcyclohexyl)aminobenzene.

A mixture of 14 g of the compound obtained in the above step and 0.8 g of 5% palladium-on-charcoal in 150 ml of 95% EtOH is hydrogenated at RT and at a pressure of 2 bar. The catalyst is filtered off on Celite and the filtrate is evaporated under vacuum. The residue is taken up in hot heptane and, after cooling, the solid formed is drained off. 6 g of the expected product are obtained in the form of the axial-equatorial isomer mixture, mp=92° C. The above draining liquors are concentrated under vacuum and 3 g of the axial isomer of the expected product are obtained.

D) 4-Ethoxy-1-ethoxycarboxamido-2-(4(a,e)-methylcyclohexyl)aminobenzene.

A mixture of 5.8 g of the compound obtained in the above step and 10 g of ethyl chloroformate in 100 ml of chloroform is maintained at reflux for 1 hour. The solvent is evaporated off under vacuum and the residue is chromatographed on silica, eluting with DCM. 5 g of the expected product are obtained, which product is used without further purification in the following step.

E) 5-Ethoxy-1,3-dihydro-3-(4(a,e)-methylcyclohexyl)-2H-benzimidazol-2-one.

To sodium ethoxide solution, prepared by adding 0.75 g of sodium to 30 ml of absolute EtOH, are added 5 g of the compound obtained in the above step and the mixture is heated at reflux for 6 hours. The reaction mixture is evaporated under vacuum and the residue is extracted with DCM, washed with water, dried over Na$_2$SO$_4$ and evaporated under vacuum. 3 g of the expected product are obtained after crystallization from iso ether, mp=190° C.

Preparation 6

5-Ethoxy-1,3-dihydro-3-(4(a)-methylcyclohexyl)-2H-benzimidazol-2-one, axial isomer A) 4-Ethoxy-1-ethoxycarboxamido-2-(4(a)-methylcyclohexyl)aminobenzene.

This compound is prepared according to the procedure described in Preparation 5 Step D, starting with 3 g of the axial isomer of the compound obtained in Preparation 5 Step C. The product is chromatographed on silica, eluting with a DCM/EtOAc mixture (90/10; v/v). 2.8 g of the expected product are obtained after crystallization from iso ether, mp=183° C.

B) 5-Ethoxy-1,3-dihydro-3-(4(a)-methylcyclohexyl)-2H-benzimidazol-2-one, axial isomer.

This compound is prepared according to the procedure described in Preparation 5 Step E, starting with 2.8 g of the compound obtained in the above step. 1.3 g of the expected product are obtained after crystallization from iso ether, mp=170° C.

Preparation 7

5-Ethoxy-1,3-dihydro-3-(4(a,e)-methoxycyclohexyl)-2H-benzimidazol-2-one

A) 4(a,e)-Methoxycyclohexylamine.

A mixture of 100 g of 4-methoxyaniline and 48 g of 5% palladium-on-charcoal in 400 ml of AcOH is hydrogenated for 3 hours, at a temperature of 75°–80° C. and at a pressure of 45 bar. The catalyst is filtered off, 20 ml of water are added to the filtrate, which is then evaporated under vacuum. The residue is taken up in 100 ml of water, cooled to 0° C., basified by addition of concentrated NaOH, extracted with ether and dried over Na$_2$SO$_4$, and the solvent is evaporated off at atmospheric pressure. The oil obtained is distilled at atmospheric pressure. 31 g of the expected product are obtained in the form of an oil, bp=183°–188° C.

B) 4-Chloro-2-(4(a,e)-methoxycyclohexyl)amino-1-nitrobenzene.

A mixture of 12 g of 4-chloro-1,2-dinitrobenzene and 7 g of the compound obtained in the above step in 30 ml of EtOH is left stirring for 15 hours. The solvent is evaporated off under vacuum and the residue is extracted with ether, washed with water, with 1N NaOH solution, with 1N HCl solution, with water and dried over Na$_2$SO$_4$, and the solvent is evaporated off under vacuum. The residue is chromatographed on silica, eluting with DCM. 6.6 g of the expected product are obtained in the form of an oil, which product is used without further purification in the following step.

C) 4-Ethoxy-2-(4(a,e)-methoxycyclohexyl)amino-1-nitrobenzene.

This compound is prepared according to the procedure described in Preparation 3 Step A, starting with 15.4 g of the compound obtained in the above step. 12 g of the expected product are obtained after crystallization from iso ether, mp=93° C.

D) 1-Amino-4-ethoxy-2-(4(a,e)-methoxycyclohexyl)aminobenzene.

A mixture of 10 g of the compound obtained in the above step and 3 g of 5% palladium-on-charcoal in 100 ml of EtOH is hydrogenated at RT, at atmospheric pressure, for 4 hours. The catalyst is filtered off and the filtrate is evaporated under vacuum. 8.5 g of the expected product are obtained in the form of a red oil, which product is used without further purification in the following step.

E) 4-Ethoxy-1-ethoxycarboxamido-2-(4(a,e)methoxycyclohexyl)aminobenzene.

A solution of 8.4 g of the compound obtained in the above step and 13 g of triethylamine in 100 ml of DCM is cooled to 10° C., and a solution of 5 ml of ethyl chloroformate in 15 ml of THF is added dropwise. The mixture is left stirring for 3 hours, allowing the temperature to return to RT, and the solvents are evaporated off under vacuum. The residue is extracted with iso ether, washed with water, with 10% Na$_2$CO$_3$ solution and dried over Na$_2$SO$_4$, and the solvent is evaporated off under vacuum. 12 g of the expected product are obtained, which product is used without further purification in the following step.

F) 5-Ethoxy-1,3-dihydro-3-(4(a,e)-methoxycyclohexyl)-2H-benzimidazol-2-one.

A mixture of 12 g of the compound obtained in the above step and 4.1 g of sodium ethoxide in 150 ml of THF is heated at reflux for 4 hours. The reaction mixture is evaporated under vacuum and the residue is dissolved in 50 ml of water, acidified to pH=1 by addition of 2N HCl, and the precipitate formed is drained off and washed with water. The precipitate is chromatographed on silica, using DCM and then a DCM/EtOAc mixture (70/30; v/v) as eluent. 7.8 g of the expected product are obtained, mp=201° C.

Preparation 8

5-Ethoxy-1,3-dihydro-3-[4(a,e)-(2-methoxyethoxy)cyclohexyl]-2H-benzimidazol-2-one A) 4-(2-methoxyethoxy)-1-nitrobenzene.

A mixture of 40 g of 4-nitrophenol, 41 g of 1-bromo-2-methoxyethane, 45 g of K$_2$CO$_3$ and 80 ml of tris[2-(2-methoxyethoxy)ethyl]amine in 80 ml of acetone is heated at reflux for 20 hours. An insoluble material is filtered off and the filtrate is concentrated under vacuum. The residue is taken up in water and the precipitate formed is drained off and washed with water. The precipitate is dissolved in EtOAc, washed with 1N NaOH solution, with water, with 1N HCl solution, with water and dried over Na$_2$SO$_4$, and the solvent is evaporated off under vacuum. 59 g of the expected product are obtained, which product is used without further purification in the following step.

B) 4-(2-Methoxyethoxy)aniline.

A mixture of 59 g of the compound obtained in the above step and 6 g of 5% palladium-on-charcoal in 400 ml of EtOH is hydrogenated at 40° C., at atmospheric pressure, for 5 hours. The catalyst is filtered off and the filtrate is evaporated under vacuum. 43 g of the expected product are obtained, which product is used without further purification in the following step.

C) 4(a,e)-(2-Methoxyethoxy)cyclohexylamine.

This compound is prepared according to the procedure described in Preparation 7 Step A, starting with 43 g of the compound obtained in the above step. The oil obtained is distilled under reduced pressure. 19 g of the expected product are obtained in the form of an oil, bp=123°–127° C. at 15 mmHg.

D) 4-Chloro-2-[[4(a,e)-(2-methoxyethoxy)cyclohexyl]amino]-1-nitrobenzene.

A mixture of 19 g of the compound obtained in the above step, 22.2 g of 4-chloro-1,2-dinitrobenzene and 20 ml of triethylamine in 30 ml of EtOH is left stirring for 15 hours at RT. The reaction mixture is evaporated under vacuum and the residue is taken up in water, extracted with ether, washed with 1N HCl solution, with water, with 1N NaOH solution, with water, died over Na$_2$SO$_4$ and evaporated under vacuum. The residue is chromatographed on silica, eluting with iso ether and then with DCM. 20 g of the expected product are obtained in the form of an orange oil, which product is used without further purification in the following step.

E) 4-Ethoxy-2-[[4(a,e)-(2-methoxyethoxy)cyclohexyl]amino]-1-nitrobenzene.

Sodium ethoxide solution is prepared by adding 1.8 g of sodium to 50 ml of EtOH, followed by addition of 19.9 g of the compound obtained in the above step, 30 ml of tris[2-(2-methoxyethoxy)ethyl]amine and 80 ml of EtOH, and the mixture is heated at reflux for 5 hours. The reaction mixture is evaporated under vacuum and the residue is taken up in 2N HCl solution, extracted with ether, washed with water, dried over Na$_2$SO$_4$ and evaporated under vacuum. 17.5 g of the expected product are obtained, which product is used without further purification in the following step.

F) 5-Ethoxy-1,3-dihydro-3-[4(a,e)-(2-methoxyethoxy)cyclohexyl]-2H-benzimidazol-2-one.

This compound is prepared according to the procedures described in Preparation 7 Steps D, E and then F, starting with 17.4 g of the compound obtained in the above step. 11.5 g of the expected product are obtained, mp=118°–120° C.

Preparation 9

5-Ethoxy-1,3-dihydro-3-(2-methoxy-1,1-dimethylethyl)-2H-benzimidazol-2-one

A) 4-Chloro-2-[(2-hydroxy-1,1-dimethylethyl)amino]-1-nitrobenzene.

A mixture of 20 g of 4-chloro-1,2-dinitrobenzene and 36 g of 2-amino-2-methylpropan-1-ol in 100 ml of EtOH is heated at reflux for 36 hours. The reaction mixture is evaporated under vacuum and the residue is taken up in EtOAc, washed with 1N HCl solution, with water, dried over Na$_2$SO$_4$ and evaporated under vacuum. The residue is chromatographed on silica, eluting with DCM. 16 g of the expected product are obtained, which product is used without further purification in the following step.

B) 4-Chloro-2-[(2-methoxy-1,1-dimethylethyl)amino]-1-nitrobenzene.

To a solution of 15 g of the compound obtained in the above step in 200 ml of THF are added 1.6 g of sodium hydride portionwise and the mixture is left stirring for 30 minutes at RT. 6 ml of methyl iodide are then added and the mixture is left stirring for 2 hours at RT. The solvent is evaporated off under vacuum and the residue is taken up in 300 ml of water, extracted with EtOAc, dried over Na$_2$SO$_4$ and evaporated under vacuum. The residue is chromatographed on silica, eluting with DCM. 12.5 g of the expected product are obtained, which product is used without further purification in the following step.

C) 4-Ethoxy-2-[(2-methoxy-1,1-dimethylethyl)amino]-1-nitrobenzene.

Sodium ethoxide solution is prepared by adding 2 g of sodium to 100 ml of EtOH, followed by addition of 12.5 g of the compound obtained in the above step, and the mixture is heated at reflux for 5 hours. The reaction mixture is concentrated under vacuum and the residue is taken up in 300 ml of water, extracted with EtOAc and dried over Na$_2$SO$_4$, and the solvent is evaporated off under vacuum. 12 g of the expected product are obtained, which product is used without further purification in the following step.

D) 1-Amino-4-ethoxy-2-[(2-methoxy-1,1-dimethylethyl)amino]benzene.

A mixture of 12 g of the compound obtained in the above step and 1.2 g of 5% palladium-on-charcoal in 250 ml of EtOAc is hydrogenated for 24 hours, at 40° C. and at atmospheric pressure. The catalyst is filtered off on Celite and the filtrate is evaporated under vacuum. 12 g of the expected product are obtained, which product is used without further purification in the following step.

E) 4-Ethoxy-1-ethoxycarboxamido-2-[(2-methoxy-1,1-dimethylethyl)amino]benzene.

A mixture of 12 g of the compound obtained in the above step and 14 g of ethyl chloroformate in 200 ml of chloroform is heated at reflux for 2 hours. After cooling, the mixture is washed with 1N NaOH solution, dried over $Na_2SO_4$ and evaporated under vacuum. The residue is chromatographed on silica, eluting with a DCM/MeOH mixture (99/1; v/v). 8.4 g of the expected product are obtained, mp=138° C.

F) 5-Ethoxy-1,3-dihydro-3-(2-methoxy-1,1-dimethylethyl)-2H-benzimidazol-2-one.

This compound is prepared according to the procedure described in Preparation 5 Step E, starting with 8.4 g of the compound obtained in the above step. 4.9 g of the expected product are obtained after crystallization from EtOH, mp=149° C.

Preparation 10

5-Ethoxy-1,3-dihydro-3-(1,1,3,3-tetramethylbutyl)-2H-benzimidazol-2-one

A) 4-Chloro-2-[(1,1,3,3-tetramethylbutyl)amino]-1-nitrobenzene.

A mixture of 20 g of 4-chloro-1,2-dinitrobenzene and 30 g of tert-octylamine in 300 ml of 95% EtOH is heated at reflux for 16 hours. The solvent is evaporated off under vacuum. 13 g of the expected product are obtained after crystallization from an iso ether/heptane mixture (40/60; v/v), mp=108° C.

B) 4-Ethoxy-2-[(1,1,3,3-tetramethylbutyl)amino]-1-nitrobenzene

This compound is prepared according to the procedure described in Preparation 9 Step C, starting with 18 g of the compound obtained in the above step. The product is chromatographed on silica, eluting with heptane. 4 g of the expected product are obtained, which product is used without further purification in the following step.

C) 1-Amino-4-ethoxy-2-[(1,1,3,3-tetramethylbutyl)amino]benzene

A mixture of 4 g of the compound obtained in the above step and 0.2 g of 5% palladium-on-charcoal in 150 ml of EtOAc is hydrogenated at RT and at atmospheric pressure. The catalyst is filtered off on Celite and the filtrate is evaporated under vacuum. 3.6 g of the expected product are obtained, which product is used without further purification in the following step.

D) 4-Ethoxy-1-ethoxycarboxamido-2-[(1,1,3,3-tetramethylbutyl)amino]benzene

A mixture of 3.6 g of the compound obtained in the above step, 2 ml of ethyl chloroformate and 2 ml of triethylamine in 100 ml of chloroform is left stirring for 1 hour. The mixture is washed with 1N NaOH solution, with water, with 1N HCl solution, with water and dried over $Na_2SO_4$, and the solvent is evaporated off under vacuum. 4 g of the expected product are obtained, which product is used without further purification in the following step.

E) 5-Ethoxy-1,3-dihydro-3-(1,1,3,3-tetramethylbutyl)-2H-benzimidazol-2-one.

Sodium ethoxide solution is prepared from 0.6 g of sodium and 100 ml of EtOH, 4 g of the compound obtained in the above step are added and the mixture is heated at reflux for 3 hours. The solvent is evaporated off under vacuum and the residue is taken up in 100 ml of water, the precipitate formed is filtered off and washed with water and then with iso ether. 2.6 g of the expected product are obtained after drying, mp=157° C.

Preparation 11

5-Chloro-1,3-dihydro-3-phenyl-2H-benzimidazol-2-one

This compound is prepared according to the procedure described in Eur. J. Med. Chem.—Chimica Therapeutica, 1981, 16 (4), 321–326.

Preparation 12

3-(2-Chlorophenyl)-5-ethoxy-1,3-dihydro-2H-benzimidazol-2-one

A) 4-Chloro-2-[(2-chlorophenyl)amino]-1-nitrobenzene.

A mixture of 101 g of 4-chloro-1,2-dinitrobenzene and 191 g of 2-chloroaniline in 750 ml of 95% EtOH is heated at reflux for 96 hours. The solvent is evaporated off under vacuum and the residue is extracted with DCM, washed with 3N HCl solution, with water and dried over $Na_2SO_4$ and the solvent is evaporated off under vacuum. The residue is chromatographed on silica, eluting with a DCM/hexane mixture (50/50; v/v). 7 g of the expected product are obtained after crystallization from EtOH, mp=97° C.

B) 2-[(2-Chlorophenyl)amino]-4-ethoxy-1-nitrobenzene.

This compound is prepared according to the procedure described in Preparation 3 Step A, starting with 7 g of the compound obtained in the above step. 3.3 g of the expected product are obtained after crystallization from iso ether.

C) 1-Amino-2-[(2-chlorophenyl)amino]-4-ethoxybenzene.

A mixture of 3.3 g of the compound obtained in the above step and 2 g of iron powder in 3 ml of water and 3 ml of EtOH is heated at reflux, followed by dropwise addition of a solution of 0.17 ml of concentrated HCl in 0.7 ml of water and 0.7 ml of EtOH. The mixture is left refluxing for two hours and, after cooling, is then basified by addition of concentrated NaOH, and the reaction mixture is filtered on Celite and washed thoroughly with EtOAc. After settling of the filtrate, the organic phase is dried over $Na_2SO_4$ and the solvent is evaporated off under vacuum. The residue is chromatographed on silica, eluting with a DCM/EtOAc mixture (90/10; v/v). 1.75 g of the expected product are obtained, which product is used without further purification in the following step.

D) 2-[2-Chlorophenyl)amino]-4-ethoxy-1-methoxycarboxamidobenzene

A mixture of 1.75 g of the compound obtained in the above step and 3 g of methyl chloroformate in 30 ml of chloroform is heated at reflux for 3 hours. The solvent is evaporated off under vacuum and the residue is extracted with DCM, washed with water and dried over $Na_2SO_4$, and the solvent is evaporated off under vacuum. 1.2 g of the expected product are obtained, which product is used without further purification in the following step.

E) 3-(2-Chlorophenyl)-5-ethoxy-1,3-dihydro-2H-benzimidazol-2-one.

This compound is prepared according to the procedure described in Preparation 5 Step E, starting with 1.2 g of the compound obtained in the above step. After evaporation of the reaction mixture under vacuum, the residue is taken up in EtOAc and washed with water, and the product precipitates out. The precipitate is filtered off and 1 g of the expected product is obtained after drying, mp=213° C.

Preparation 13

5-Ethoxy-3-(tetrahydropyran-4-yl)-1,3-dihydro-2H-benzimidazol-2-one

A) Tetrahydro-4H-pyran-4-one oxime.

To a solution of 35 g of tetrahydro-4H-pyran-4-one in 225 ml of pyridine is added a solution of 29 g of hydroxylamine hydrochloride in 90 ml of EtOH and the mixture is left stirring for 48 hours at RT. The reaction mixture is concentrated to 50 ml, 500 ml of ice-water are added, the mixture is extracted 6 times with EtOAc and dried over $Na_2SO_4$, and the solvent is evaporated off under vacuum. 26 g of the expected product are obtained, mp=94° C.

B) 4-Aminotetrahydropyran.

A mixture of 32 g of the compound obtained in the above step in 300 ml of EtOH in the presence of Raney nickel is hydrogenated for 3 hours at 60° C. and at a pressure of 20 bar. The catalyst is filtered off, the solvent is evaporated off under vacuum and the oil obtained is distilled at atmospheric pressure. 18 g of the expected product are obtained, bp=150°–175° C.

C) 4-Chloro-1-nitro-2-[(tetrahydropyran-4-yl)amino] benzene.

A mixture of 33 g of 4-chloro-1,2-dinitrobenzene, 18 g of the compound obtained in the above step and 22 g of triethylamine in 250 ml of 96% EtOH is heated at 60° C. for 48 hours. After cooling, the precipitate formed is filtered off and washed with EtOH and then with iso ether. 24.4 g of the expected product are obtained, mp=155° C.

D) 4-Ethoxy-1-nitro-2-[(tetrahydropyran-4-yl)amino] benzene.

This compound is prepared according to the procedure described in Preparation 9 Step C, starting with 24.4 g of the compound obtained in the above step. 21.4 g of the expected product are obtained after crystallization from iso ether, mp=117° C.

E) 1-Amino-4-ethoxy-2-[(tetrahydropyran-4-yl)amino] benzene

A mixture of 21.4 g of the compound obtained in the above step and 2 g of 5% palladium-on-charcoal in 500 ml of EtOAc is hydrogenated at 40° C. and at atmospheric pressure. The catalyst is filtered off on Celite and the filtrate is evaporated under vacuum. 18 g of the expected product are obtained, mp=101° C.

F) 4-Ethoxy-2-[(tetrahydropyran-4-yl)amino]-1-methoxycarboxamidobenzene.

To a solution of 19 g of the compound obtained in the above step and 15 ml of triethylamine in 500 ml of chloroform are added dropwise 30 ml of methyl chloroformate, and the mixture is left stirring for 3 hours at RT. The mixture is washed with 1N HCl solution, with 1N NaOH solution, dried over $Na_2SO_4$ and the solvent is evaporated off under vacuum. 13.8 g of the expected product are obtained after crystallization from an iso ether/EtOH mixture (80/20; v/v), mp=185° C.

G) 5-Ethoxy-3-(tetrahydropyran-4-yl)-1,3-dihydro-2H-benzimidazol-2-one.

A mixture of 13.8 g of the compound obtained in the above step with sodium ethoxide solution prepared from 3.5 g of sodium in 300 ml of EtOH is heated at reflux for 3 hours. The solvent is evaporated off under vacuum, the residue is taken up in water and the precipitate formed is filtered off and washed with EtOAc. 8.4 g of the expected product are obtained, mp=222° C.

Preparation 14

3-Cyclohexyl-5-cyclopentyloxy-1,3-dihydro-2H-benzimidazol-2-one

A) 2-Cyclohexylamino-4-cyclopentyloxy-1-nitrobenzene.

Sodium cyclopentoxide solution, prepared from 0.9 g of sodium in 150 ml of cyclopentanol, is heated to 50° C., 10 g of the compound obtained in Preparation 1 Step A and 12 ml of tris[2-(2-methoxyethoxy)ethyl]amine are added and the mixture is then heated at 100° C. for 30 hours. The cyclopentanol is distilled off under vacuum, the residue is taken up in water, extracted with EtOAc, washed with water and dried over $Na_2SO_4$, and the solvent is evaporated off under vacuum. The residue is chromatographed on silica, eluting with heptane. 4.7 g of the expected product are obtained, mp=98° C.

B) 1-Amino-2-cyclohexylamino-4-cyclopentyloxybenzene.

A mixture of 4.7 g of the compound obtained in the above step and 0.3 g of 5% palladium-on-charcoal in 120 ml of 95% EtOH is hydrogenated for 3 hours, at RT and at a pressure of 2 bar. The catalyst is filtered off on Celite and the filtrate is evaporated under vacuum. 4 g of the expected product are obtained, mp=80° C.

C) 2-Cyclohexylamino-4-cyclopentyloxy-1-ethoxycarboxamidobenzene

A mixture of 4 g of the compound obtained in the above step and 6 g of ethyl chloroformate in 50 ml of chloroform is heated at reflux for 2 hours. The reaction mixture is washed with water and dried over $Na_2SO_4$, and the solvent is evaporated off under vacuum. The residue is chromatographed on silica, eluting with a DCM/EtOAc mixture (75/25; v/v). 2.6 g of the expected product are obtained after crystallization from iso ether, mp=202° C.

D) 3-Cyclohexyl-5-cyclopentyloxy-1,3-dihydro-2H-benzimidazol-2-one.

To sodium ethoxide solution, prepared from 0.2 g of sodium in 50 ml of EtOH, are added 2.5 g of the compound obtained in the above step and the mixture is heated at reflux for 18 hours. The solvent is evaporated off under vacuum, the residue is extracted with EtOAc, washed with water and dried over $Na_2SO_4$, and the solvent is evaporated off under vacuum. 1.7 g of the expected product are obtained after crystallization from iso ether, mp=242° C.

Preparation 15

3-Cyclohexyl-1,3-dihydro-5-(2-methoxyethoxy)-2H-benzimidazol-2-one

A) 2-Cyclohexylamino-4-(2-methoxyethoxy)-1-nitrobenzene.

To sodium (2-methoxy)ethoxide solution, prepared from 0.9 g of sodium in 100 ml of 2-methoxyethanol, are added 10 g of the compound obtained in Preparation 1 Step A and 12 ml of tris[2-(2-methoxyethoxy)ethyl]amine and the mixture is then heated at reflux for 5 hours. The reaction mixture is evaporated under vacuum, the residue is extracted with EtOAc, washed with water and dried over $Na_2SO_4$, and the solvent is evaporated off under vacuum. The residue is chromatographed on silica, eluting with a DCM/heptane mixture (50/50; v/v). 7 g of the expected product are obtained, which product is used without further purification in the following step.

B) 1-Amino-2-cyclohexylamino-4-(2-methoxyethoxy) benzene.

A mixture of 7 g of the compound obtained in the above step and 0.5 g of 5% palladium-on-charcoal in 200 ml of 95% EtOH is hydrogenated at RT and at a pressure of 2 bar. The catalyst is filtered off on Celite and the filtrate is evaporated under vacuum. 5 g of the expected product are obtained, which product is used without further purification in the following step.

C) 2-Cyclohexylamino-1-ethoxycarboxamido-4-(2-methoxyethoxy)benzene.

A mixture of 5 g of the compound obtained in the above step and 6 g of ethyl chloroformate in 50 ml of chloroform is heated at reflux for 3 hours. The solvent is evaporated off under vacuum and the residue is chromatographed on silica, eluting with DCM. 6 g of the expected product are obtained, mp=145° C.

D) 3-Cyclohexyl-1,3-dihydro-5-(2-methoxyethoxy)-2H-benzimidazol-2-one.

To sodium ethoxide solution, prepared from 0.45 g of sodium in 100 ml of EtOH, are added 6 g of the compound obtained in the above step and the mixture is heated at reflux for 25 hours. The solvent is evaporated off under vacuum, the residue is extracted with EtOAc, washed with water and dried over $Na_2SO_4$, and the solvent is evaporated off under vacuum. 2.2 g of the expected product are obtained after crystallization from iso ether, mp=182° C.

Preparation 16

5-Chloro-3-(3-chlorophenyl)-1,3-dihydro-2H-benzimidazol-2-one

A) 4-Chloro-2-[(3-chlorophenyl)amino]-1-nitrobenzene.

A mixture of 50 g of 2,4-dichloro-1-nitrobenzene, 40 ml of 3-chloroaniline and 43 g of anhydrous sodium acetate in 220 ml of ethylene glycol is heated at reflux for 72 hours. After cooling, the precipitate formed is filtered off and washed with water. 39 g of the expected product are obtained after crystallization from iso ether, mp=112° C.

B) 1-Amino-4-chloro-2-[(3-chlorophenyl)amino] benzene.

To a mixture of 38 g of the compound obtained in the above step, 140 ml of concentrated HCl and 390 ml of EtOH are added portionwise 64 g of tin powder, while maintaining the temperature below 50° C. The reaction mixture is left stirring for 1 hour and filtered on Celite, and the filtrate is evaporated under vacuum. The residue is extracted with DCM, washed with water and dried over $Na_2SO_4$, and the solvent is evaporated off under vacuum. 38 g of the expected product are obtained, mp=82° C.

C) 4-Chloro-2-[(3-chlorophenyl)amino]-1-ethoxycarboxamidobenzene

To a mixture of 18 g of the compound obtained in the above step and 10 g of potassium carbonate in 160 ml of DMF and 55 ml of water are added slowly 6.8 ml of ethyl chloroformate, while maintaining the temperature at 20° C. The mixture is left stirring for 1 hour, 300 ml of water are added and the mixture is extracted with DCM, washed with water and dried over $Na_2SO_4$, and the solvent is evaporated off under vacuum. The residue is chromatographed on silica, eluting with a cyclohexane/DCM mixture (80/20; v/v). 19 g of the expected product are obtained, mp=96° C.

D) 5-Chloro-3-(3-chlorophenyl)-1,3-dihydro-2H-benzimidazol-2-one.

To sodium ethoxide solution, prepared from 2.6 g of sodium in 100 ml of EtOH, are added 18 g of the compound obtained in the above step and the mixture is heated at 60° C. for 1 hour. The solvent is evaporated off under vacuum and the residue is taken up in 200 ml of water and acidified to pH=1 by addition of concentrated HCl, and the precipitate formed is filtered off. 12.6 g of the expected product are obtained, mp=245° C.

Preparation 17

3-(1-Benzylpiperid-4-yl)-5-chloro-1,3-dihydro-2H-benzimidazol-2-one

A) 2-[(1-Benzylpiperid-4-yl)amino]-4-chloro-1-nitrobenzene.

A solution of 38.4 g of 2,4-dichloro-1-nitrobenzene in 160 ml of 2-ethoxyethanol is heated to 100° C. A solution of 152.23 g of N-benzyl-4-aminopiperidine in 40 ml of 2-ethoxyethanol is then added slowly. The mixture is maintained at reflux for 5 hours. The solvent is evaporated off under vacuum and the residue is taken up in $H_2O$, extracted with EtOAc, washed with water and dried over $Na_2SO_4$, and the solvent is evaporated off under vacuum. The residue is chromatographed on silica, eluting with isopropyl ether. 24.4 g of the expected product are obtained after crystallization from isopropyl ether, mp=84° C.

B) 1-Amino-2-[(1-benzylpiperid-4-yl)amino]-4-chlorobenzene.

A mixture of 20.75 g of the compound obtained in Step A and 10 g of iron powder in 19 ml of water and 19 ml of ethanol is brought to reflux. A solution of 37.5 ml of concentrated hydrochloric acid in 25 ml of water and 25 ml of ethanol is added dropwise to this mixture and the reflux is maintained for 1 hour 30 minutes. After cooling, the reaction mixture is run onto ice and then treated with saturated $NaHCO_3$ solution and extracted with EtOAc. The mixture is washed with water and dried over $Na_2SO_4$, and the solvent is evaporated off under vacuum. The residue is chromatographed on silica, eluting with a DCM/MeOH mixture (92/8; v/v). After crystallization from isopropyl ether, 12.71 g of the expected product are obtained, mp=108° C.

C) 3-(1-Benzylpiperid-4-yl)-5-chloro-1,3-dihydro-2H-benzimidazol-2-one.

A mixture of 12.71 g of the compound obtained in Step B and 8.9 g of 1,1'-carbonyldiimidazole in 130 ml of acetonitrile is maintained at reflux for 3 hours. The solvent is evaporated off under vacuum and the residue is taken up in water, extracted with DCM, washed with saturated $NaHCO_3$ solution, washed with water and dried over $Na_2SO_4$, and the solvent is evaporated off under vacuum. The residue is chromatographed on silica, eluting with a DCM/MeOH mixture (92/8; v/v). After recrystallization from absolute ethanol, 8.9 g of the expected product are obtained, mp=204°–206° C.

Preparation 18

5-Chloro-3-cycloheptyl-1,3-dihydro-2H-benzimidazol-2-one

A) 4-Chloro-2-cycloheptylamino-1-nitrobenzene.

A mixture of 18.2 g of 4-chloro-1,2-dinitrobenzene and 31 g of cycloheptylamine in 55 ml of 95% EtOH is left stirring for 15 hours at RT. The reaction mixture is concentrated under vacuum, the residue is extracted with EtOAc, washed with 1N HCl solution, with water and dried over $Na_2SO_4$, and the solvent is evaporated off under vacuum. The residue is chromatographed on silica, eluting with petroleum ether. 13 g of the expected product are obtained after crystallization from isopropanol.

B) 1-Amino-4-chloro-2-cycloheptylaminobenzene.

A mixture of 12.9 g of the compound obtained in the above step and 8 g of iron powder in 15 ml of water and 15 ml of EtOH is heated at reflux. A solution of 30 ml of concentrated HCl in 20 ml of EtOH and 20 ml of water is then added dropwise and the mixture is maintained at reflux for 1 hour 30 minutes. After cooling, the reaction mixture is filtered on Celite and washed with MeOH, and the filtrate is concentrated under vacuum. The residue is taken up in ice, basified by addition of saturated $NaHCO_3$ solution, extracted with DCM, washed with water and dried over $Na_2SO_4$, and the solvent is evaporated off under vacuum. The residue is chromatographed on silica, eluting with petroleum ether and then with iso ether. 10 g of the expected product are obtained in the form of an oil, which product is used without further purification in the following step.

C) 5-Chloro-3-cycloheptyl-1,3-dihydro-2H-benzimidazol-2-one.

A mixture of 9.9 g of the compound obtained in the above step and 9.3 g of 1,1'-carbonyldiimidazole in 150 ml of acetonitrile is heated at reflux for 10 minutes. The solvent is evaporated off under vacuum, the residue is taken up in saturated $NaHCO_3$ solution, extracted with DCM, washed with water and dried over $Na_2SO_4$, and the solvent is evaporated off under vacuum. The residue is taken up in 100 ml of iso ether and the precipitate formed is drained off. The precipitate is chromatographed on silica, eluting with DCM and then with a DCM/EtOAc mixture (80/20; v/v). 8.1 g of the expected product are obtained, mp=201° C.

Preparation 19

5-Ethoxy-1,3-dihydro-3-[4(a,e)-(2(R,S)-tetrahydropyranyloxy)cyclohexyl]-2H-benzimdazol-2-one A) 4-Chloro-2-[(4(a,e)-hydroxycyclohexyl)amino]-1-nitrobenzene.

A mixture of 19.8 g of 4-chloro-1,2-dinitrobenzene and 45 g of 4-aminocyclohexanol (mixture of isomers) in 75 ml of EtOH is left stirring for 15 hours at RT. The reaction mixture is evaporated under vacuum, the residue is extracted with ether, washed with 1N HCl solution, with water and dried over $Na_2SO_4$, and the solvent is evaporated off under vacuum. The residue is chromatographed on silica, eluting with iso ether. 14.8 g of the expected product are obtained in the form of an oil, which product is used without further purification in the following step.

B) 4-Chloro-2-[[4(a,e)-(2(R,S)-tetrahydropyranyloxy) cyclohexyl]amino]-1-nitrobenzene.

A mixture of 15.5 g of the compound obtained in the above step, 10.5 g of 3,4-dihydro-2H-pyran and 0.1 g of para-toluenesulfonic acid in 250 ml of ether is left stirring for 20 hours at RT. The solvent is evaporated off under vacuum and 23 g of the expected product are obtained in the form of an oil, which product is used without further purification in the following step.

C) 4-Ethoxy-2-[[4(a,e)-(2(R,S)-tetrahydropyranyloxy) cyclohexyl]amino]-1-nitrobenzene.

To sodium ethoxide solution, prepared from 1.8 g of sodium in 30 ml of EtOH, are added 21 g of the compound obtained in the above step and 10 ml of tris[2-(2-methoxyethoxy)ethyl]amine and the mixture is heated at reflux for 5 hours. The reaction mixture is evaporated under vacuum, the residue is taken up in water, cooled to 0° C., acidified to pH=1 by addition of 1N HCl, extracted rapidly with ether, washed with water and dried over $Na_2SO_4$, and the solvent is evaporated off under vacuum. 23 g of the expected product are obtained in the form of an oil, which product is used without further purification in the following step.

D) 1-Amino-4-ethoxy-2[[4(a,e)-(2(R,S)-tetrahydropyranyloxy)cyclohexyl]amino]benzene.

A mixture of 23 g of the product obtained in the above step and 3 g of 5% palladium-on-charcoal in 90 ml of EtOH is hydrogenated at 35°–40° C. and at atmospheric pressure for 6 hours. The catalyst is filtered off and the filtrate is evaporated under vacuum. 20 g of the expected product are obtained in the form of an oil, which product is used without further purification in the following step.

E) 4-Ethoxy-1-ethoxycarboxamido-2-[[4(a,e)-(2(R,S)-tetrahydropyranyloxy)cyclohexyl]amino]benzene.

A mixture of 19.9 g of the compound obtained in the above step and 27 g of triethylamine in 150 ml of DCM is cooled to 5° C., a solution of 6.5 ml of ethyl chloroformate in 25 ml of THF is added dropwise and the mixture is left stirring for 3 hours while allowing the temperature to return to RT. The reaction mixture is evaporated under vacuum, the residue is extracted with ether, washed with water and dried over $Na_2SO_4$, and the solvent is evaporated off under vacuum. The residue is chromatographed on alumina, eluting with iso ether, and the product obtained is then rechromatographed on silica, eluting with iso ether and then with DCM. 4 g of the expected product are obtained in the form of an oil, which product is used without further purification in the following step.

F) 5-Ethoxy-1,3-dihydro-3-[4(a,e)-(2(R,S)-tetrahydropyranyloxy)cyclohexyl]-2H-benzimidazol-2-one.

To sodium ethoxide solution, prepared from 0.3 g of sodium in 50 ml of EtOH, are added 4 g of the compound obtained in the above step and the mixture is heated at reflux for 3 hours. The reaction mixture is evaporated under vacuum, the residue is extracted with EtOAc, washed with water and dried over $Na_2SO_4$, and the solvent is evaporated off under vacuum. 1.5 g of the expected product are obtained after crystallization from iso ether, mp=135°–145° C.

Preparation 20

5-Ethoxy-1,3-dihydro-3-[2-(N,N-diisopropylamino) ethyl]-2H-benzimidazol-2-one

A) 4-Chloro-2-[N-[2-(N',N'-diisopropylamino)ethyl] amino]-1-nitrobenzene.

To a solution of 19.5 g of 4-chloro-1,2-dinitrobenzene in 150 ml of EtOH are added 39 g of N,N-diisopropylethylenediamine. The temperature rises to 50° C. The reaction medium is kept stirring for 3 hours and the solvent is then evaporated off under vacuum. The residue is taken up in 200 ml of isopropanol, cooled to 0° C. and left to stand at this temperature, and the precipitate formed is then filtered off. 12 g of the expected product are obtained after recrystallization from isopropanol.

B) 4-Ethoxy-2-[N-[2-(N',N'-diisopropylamino)ethyl] amino]-1-nitrobenzene.

This compound is prepared according to the procedure described in Preparation 3 Step A, starting with 11.3 g of the compound obtained in the above step. The product is chromatographed on silica, eluting with a DCM/MeOH mixture (97/3; v/v). 6.7 g of the expected product are obtained after crystallization from heptane, mp=89° C.

C) 1-Amino-4-ethoxy-2-[N-[2-(N'N'-diisopropylamino) ethyl]amino]benzene.

A mixture of 6.7 g of the compound obtained in the above step and 0.55 g of 5% palladium-on-charcoal in 550 ml of EtOH is hydrogenated for 8 hours at RT and at atmospheric pressure. The catalyst is filtered off on Celite and the filtrate is evaporated under vacuum. 5.8 g of the expected product are obtained, which product is used without further purification in the following step.

D) 4-Ethoxy-1-ethoxycarboxamido-2-[N-ethoxycarbonyl-N-[2-(N',N'-diisopropylamino)ethyl]amino]benzene.

To a solution of 5.8 g of the compound obtained in the above step in 25 ml of chloroform are added dropwise 5.5 ml of ethyl chloroformate, and the mixture is heated at reflux for 20 hours. The solvent is evaporated off under vacuum, the residue is taken up in saturated NaHCO$_3$ solution, extracted with DCM and dried over Na$_2$SO$_4$, and the solvent is evaporated off under vacuum. The residue is chromatographed on silica, eluting with a DCM/MeOH mixture (95/5; v/v). 5.9 g of the expected product are obtained, which product is used without further purification in the following step.

E) 5-Ethoxy-1,3-dihydro-3-[2-(N,N-diisopropylamino) ethyl]-2H-benzimidazol-2-one.

To sodium ethoxide solution, prepared from 0.8 g of sodium in 35 ml of EtOH, are added 5.9 g of the compound obtained in the above step, and the mixture is heated at reflux for 3 hours. The solvent is evaporated off under vacuum, the residue is taken up in water, extracted with DCM and dried over Na$_2$SO$_4$, and the solvent is evaporated off under vacuum. The residue is taken up in iso ether and the precipitate formed is drained off. 2.4 g of the expected product are obtained, mp=120° C.

Preparation 21

5-Ethoxy-1,3-dihydro-3-[2-(morpholin-4-yl)ethyl]-2H-benzimidazol-2-one

A) 4-Chloro-2-[N-[2-morpholin-4-yl)ethyl]amino]-1-nitrobenzene.

A mixture of 19.5 g of 4-chloro-1,2-dinitrobenzene and 35 g of 4-(2-aminoethyl)morpholine in 180 ml of EtOH is left stirring for 20 hours at RT. The precipitate formed is drained off and is washed with iso ether. 17.1 g of the expected product are obtained after two successive crystallizations from isopropanol.

B) 4-Ethoxy-2-[N-[2-(morpholin-4-yl)ethyl]amino]-1-nitrobenzene.

This compound is prepared according to the procedure described in Preparation 3 Step A, starting with 8.6 g of the compound obtained in the above step. The product is chromatographed on silica, eluting with a DCM/MeOH mixture (99/1; v/v). 4.3 g of the expected product are obtained, mp=107° C.

C) 1-Amino-4-ethoxy-2-[N-[2-(morpholin-4-yl)ethyl] amino]-1-nitrobenzene.

A mixture of 4.3 g of the compound obtained in the above step and 0.4 g of 5% palladium-on-charcoal in 400 ml of EtOH is hydrogenated for 1 hour at RT and at atmospheric pressure. The catalyst is filtered off on Celite and the filtrate is evaporated under vacuum. The residue is chromatographed on silica, eluting with a DCM/MeOH mixture (95/5; v/v). 3.7 g of the expected product are obtained in the form of an oil, which product is used without further purification in the following step.

D) 4-Ethoxy-1-ethoxycarboxamido-2-[N-[2-(morpholin-4-yl)ethyl]amino]benzene.

To a solution of 3.7 g of the compound obtained in the above step in 20 ml of chloroform are added 3 ml of ethyl chloroformate dropwise at RT, and the mixture is heated at reflux for 4 hours. The solvent is evaporated off under vacuum, the residue is taken up in saturated NaHCO$_3$ solution, extracted with DCM and dried over Na$_2$SO$_4$, and the solvent is evaporated off under vacuum. 4.5 g of the expected product are obtained, which product is used without further purification in the following step.

E) 5-Ethoxy-1,3-dihydro-3-[2-(morpholin-4-yl)ethyl]-2H-benzimidazol-2-one.

To sodium ethoxide solution, prepared from 0.6 g of sodium in 25 ml of EtOH, are added 4.5 g of the compound obtained in the above step, and the mixture is heated at reflux for 3 hours. The solvent is evaporated off under vacuum, the residue is taken up in water, extracted with DCM and dried over Na$_2$SO$_4$, and the solvent is evaporated off under vacuum. The residue is chromatographed on silica, eluting with a DCM/MeOH mixture (95/5; v/v). The product obtained is taken up in iso ether and the precipitate formed is drained off. 0.85 g of the expected product is obtained, mp=160° C.

Preparation 22

5-Ethoxy-1,3-dihydro-3-(4(a,e)-dimethylaminocyclohexyl)-2H-benzimidazol-2-one

A) 4-Dimethylaminocyclohexylamine.

A mixture of 68 g of 4-dimethylaminoaniline and 34 g of 5% palladium-on-charcoal in 250 ml of AcOH is hydrogenated at a temperature of 75°–90° C. and at a pressure of 50 bar. The catalyst is filtered off and washed with water, and the filtrate is evaporated under vacuum. The residue is taken up in water, basified by addition of concentrated NaOH, extracted with EtOAc and dried over Na$_2$SO$_4$, and the solvent is evaporated off under vacuum. The oil obtained is distilled under reduced pressure. 16.2 g of the expected product are obtained in the form of an oil, bp=102°–110° C. at 20 mmHg.

B) 4-Chloro-2-[(4(a,e)-dimethylaminocyclohexyl)amino]-1-nitrobenzene.

A mixture of 22 g of 4-chloro-1,2-dinitrobenzene, 16 g of the compound obtained in the above step and 20 ml of triethylamine in 30 ml of EtOH is left stirring for 20 hours at RT. The reaction mixture is evaporated under vacuum, the residue is taken up in water, extracted with EtOAc, washed with water and dried over Na$_2$SO$_4$, and the solvent is evaporated off under vacuum. The residue is chromatographed on alumina, eluting with DCM. 14.9 g of the expected product are obtained in the form of an oil which crystallizes, mp=85° C.

C) 4-Ethoxy-2-[(4(a,e)-dimethylaminocyclohexyl)amino]-1-nitrobenzene

To sodium ethoxide solution, prepared from 1.5 g of sodium in 80 ml of EtOH, are added 14.9 g of the compound obtained in the above step and 15 ml of tris[2-(2- methoxyethoxy)ethyl]amine and the mixture is heated at reflux for 5 hours. The reaction mixture is evaporated under vacuum, the residue is taken up in water, extracted with iso ether, washed with water and dried over $Na_2SO_4$, and the solvent is evaporated off under vacuum. 9 g of the expected product are obtained after crystallization from iso ether, mp=75° C.

D) 1-Amino-4-ethoxy-2-[(4(a,e)-dimethylaminocyclohexyl)amino]benzene.

A mixture of 9 g of the compound obtained in the above step and 2 g of 5% palladium-on-charcoal in 40 ml of EtOH is hydrogenated for 3 hours at RT and at atmospheric pressure. The catalyst is filtered off and washed with MeOH, and the filtrate is evaporated under vacuum. 7.3 g of the expected product are obtained in the form of an oil, which product is used without further purification in the following step.

E) 4-Ethoxy-1-ethoxycarboxamido-2-[(4(a,e)-dimethylaminocyclohexyl)amino]benzene.

A mixture of 7.2 g of the compound obtained in the above step and 12 g of triethylamine in 70 ml of DCM is cooled to 10° C. and a solution of 2.9 ml of ethyl chloroformate in 10 ml of DCM is added dropwise. The mixture is left stirring for 3 hours while allowing the temperature to return to RT, and is evaporated under vacuum. The residue is taken up in water, extracted with DCM and dried over $Na_2SO_4$, and the solvent is evaporated off under vacuum. 3.7 g of the expected product are obtained after crystallization from iso ether, mp=193°–195° C.

F) 5-Ethoxy-1,3-dihydro-3-(4(a,e)-dimethylaminocyclohexyl)-2H-benzimidazol-2-one.

To a sodium ethoxide solution, prepared from 0.3 g of sodium in 30 ml of EtOH, are added 3.6 g of the compound obtained in the above step, and the mixture is heated at reflux for 5 hours. The residue is taken up in water and the precipitate formed is drained off and washed with water, with isopropanol and with pentane. 2.15 g of the expected product are obtained, mp=215°–217° C.

Preparation 23

5-Ethoxy-1,3-dihydro-3-(4-methylpiperazin-1-yl)-2H-benzimidazol-2-one

A) 4-Chloro-2-[(4-methylpiperazin-1-yl)amino]-1-nitrobenzene.

A mixture of 35 g of 4-chloro-1,2-dinitrobenzene and 20 g of 1-amino-4-methylpiperazine in 200 ml of 96% EtOH is left stirring for 24 hours at RT. The reaction mixture is evaporated under vacuum and the residue is chromatographed on silica, eluting with a DCM/EtOAc mixture (80/20; v/v). 17.5 g of the expected product are obtained after crystallization from an iso ether/heptane mixture (50/50; v/v), mp=108° C.

B) 4-Ethoxy-2-[(4-methylpiperazin-1-yl)amino]-1-nitrobenzene.

To sodium ethoxide solution, prepared from 1.5 g of sodium in 85 ml of EtOH, are added 17.5 g of the compound obtained in the above step and 13 ml of tris[2-(2-methoxyethoxy)ethyl]amine, and the mixture is heated at reflux for 4 hours. The reaction mixture is evaporated under vacuum, the residue is taken up in water, extracted with DCM and dried over $Na_2SO_4$, and the solvent is evaporated off under vacuum. 13.5 g of the expected product are obtained after crystallization from iso ether, mp=145° C.

C) 1-Amino-4-ethoxy-2-[(4-methylpiperazin-1-yl)amino]benzene.

A mixture of 13.8 g of the compound obtained in the above step and 0.75 g of 5% palladium-on-charcoal in 350 ml of 96% EtOH is hydrogenated for 3 hours at RT and at atmospheric pressure. The catalyst is filtered off and the filtrate is evaporated under vacuum. 10.5 g of the expected product are obtained, which product is used without further purification in the following step.

D) 4-Ethoxy-1-ethoxycarboxamido-2-[(4-methylpiperazin-1-yl)amino]benzene.

A mixture of 5 g of the compound obtained in the above step and 2.2 ml of triethylamine in 60 ml of DCM is cooled on an ice bath and a solution of 2.2 ml of ethyl chloroformate in 20 ml of DCM is added dropwise. The mixture is left stirring for 16 hours while allowing the temperature to return to RT, and the solvent is evaporated off under vacuum. The residue is chromatographed on silica, eluting with a DCM/MeOH mixture (90/10; v/v). 2.5 g of the expected product are obtained, which product is used without further purification in the following step.

E) 5-Ethoxy-1,3-dihydro-3-(4-methylpiperazin-1-yl)-2H-benzimidazol-2-one.

To sodium ethoxide solution, prepared from 0.36 g of sodium in 15 ml of EtOH, is added a solution of 2.5 g of the compound obtained above in 20 ml of EtOH and the mixture is heated at reflux for 8 hours. The mixture is evaporated under vacuum, the residue is taken up in water, extracted with EtOAc, washed with water and dried over $Na_2SO_4$, and the solvent is evaporated off under vacuum. The residue is chromatographed on silica, eluting with a DCM/EtOAc mixture (90/10; v/v). 0.75 g of the expected product is obtained after crystallization from iso ether, mp=203° C.

Preparation 24

5-Ethoxy-1,3-dihydro-3-(morpholin-4-yl)-2H-benzimidazol-2-one

A) 4-Chloro-2-[(morpholin-4-yl)amino]-1-nitrobenzene.

A mixture of 45 g of 4-chloro-1,2-dinitrobenzene, 25 g of 4-aminomorpholine and 30 g of triethylamine in 250 ml of 96% EtOH is left stirring for 48 hours at RT. The precipitate formed is filtered off and is washed with iso ether. 30.2 g of the expected product are obtained, mp=155° C.

B) 4-Ethoxy-2-[(morpholin-4-yl)amino]-1-nitrobenzene.

To sodium ethoxide solution, prepared from 3.5 g of sodium in 250 ml of EtOH, are added 30.2 g of the compound obtained in the above step and the mixture is heated at reflux for 5 hours. The solvent is evaporated off under vacuum, the residue is extracted with EtOAc, washed with water and dried over $Na_2SO_4$, and the solvent is evaporated off under vacuum. 19 g of the expected product are obtained after crystallization from EtOH, mp=152° C.

C) 1-Amino-4-ethoxy-2-[(morpholin-4-yl)amino]benzene.

A mixture of 19 g of the compound obtained in the above step and 2 g of 5% palladium-on-charcoal in 1000 ml of EtOAc is hydrogenated at RT and at atmospheric pressure. The catalyst is filtered off and the filtrate is evaporated under vacuum. 14 g of the expected product are obtained in the form of an oil, which product is used without further purification in the following step.

D) 4-Ethoxy-1-ethoxycarboxamido-2-[(morpholin-4-yl)amino]benzene.

A mixture of 14 g of the compound obtained in the above step and 5 ml of triethylamine in 300 ml of chloroform is cooled on an ice bath and 10 ml of ethyl chloroformate are added. The reaction mixture is left stirring for 30 minutes at RT, washed with 1N NaOH solution, the organic phase is dried over $Na_2SO_4$ and the solvent is evaporated off under vacuum. The residue is taken up in iso ether, an insoluble material is filtered off and the filtrate is chromatographed on silica, eluting with a DCM/MeOH mixture (99/1; v/v). 5 g of the expected product are obtained, which product is used without further purification in the following step.

E) 5-Ethoxy-1,3-dihydro-3-(morpholin-4-yl)-2H-benzimidazol-2-one.

To sodium ethoxide solution, prepared from 1 g of sodium in 50 ml of EtOH, are added 5 g of the compound obtained in the above step and the mixture is heated at reflux for 5 hours. The mixture is evaporated under vacuum, the residue is extracted with EtOAc, washed with water and dried over $Na_2SO_4$, and the solvent is evaporated off under vacuum. 1.87 g of the expected product are obtained after crystallization from DCM and recrystallization from EtOH, mp=228° C.

Preparation 25

5-Ethoxy-1,3-dihydro-3-(4-methoxyphenyl)-2H-benzimidazol-2-one

A) 4-Chloro-2-[(4-methoxyphenyl)amino]-1-nitrobenzene.

A mixture of 10 g of 4-chloro-1,2-dinitrobenzene, 6.5 g of 4-methoxyaniline and 16 g of 1,2,3,4-tetramethylbenzene is heated at reflux for 15 hours. After cooling, water is added and the mixture is extracted with EtOAc, washed with 1N HCl solution, with 1N NaOH solution, with water and dried over $Na_2SO_4$, and the solvent is evaporated off under vacuum. The residue is taken up in iso ether, a gummy insoluble material is separated out and the filtrate is chromatographed on alumina, eluting with iso ether. 4.6 g of the expected product are obtained after crystallization from isopropanol, mp=98° C.

B) 4-Ethoxy-2-[(4-methoxyphenyl)amino]-1-nitrobenzene.

To sodium ethoxide solution, prepared from 0.45 g of sodium in 20 ml of EtOH, are added 4.5 g of the compound obtained in the above step and 5 ml of tris[2-(2-methoxyethoxy)ethyl]amine, and the mixture is heated at reflux for 3 hours. The mixture is evaporated under vacuum, the residue is taken up in water, extracted with ether, washed with 1N HCl solution, with water, dried over $Na_2SO_4$ and evaporated under vacuum. 2.2 g of the expected product are obtained after crystallization from iso ether, mp=109° C.

C) 1-Amino-4-ethoxy-2-[(4-methoxyphenyl)amino]benzene.

A mixture of 2.2 g of the compound obtained in the above step and 0.5 g of 5% palladium-on-charcoal in 20 ml of EtOH is hydrogenated for 8 hours at RT and at atmospheric pressure. The catalyst is filtered off and washed with EtOH, and the filtrate is evaporated under vacuum. 1.9 g of the expected product are obtained, which product is used without further purification in the following step.

D) 4-Ethoxy-1-ethoxycarboxamido-2-[(4-methoxyphenyl)amino]benzene.

A mixture of 1.9 g of the compound obtained in the above step and 3 g of triethylamine in 20 ml of DCM is cooled to 5° C. and 1.1 g of ethyl chloroformate are added. The mixture is left stirring for 3 hours while allowing the temperature to return to RT, and is evaporated under vacuum. The residue is taken up in water and dried over $Na_2SO_4$, and the solvent is evaporated off under vacuum. 2.4 g of the expected product are obtained, which product is used without further purification in the following step.

E) 5-Ethoxy-1,3-dihydro-3-(4-methoxyphenyl)-2H-benzimidazol-2-one.

To sodium ethoxide solution, prepared from 0.17 g of sodium in 10 ml of EtOH, is added a solution of 2.4 g of the compound obtained in the above step in 15 ml of EtOH, and the mixture is heated at reflux for 4 hours. The mixture is evaporated under vacuum, the residue is taken up in 1N HCl solution and the precipitate formed is drained off and washed with water and then with DCM. 1.7 g of the expected product are obtained, mp=204° C.

Preparation 26

5-Ethoxy-1,3-dihydro-3-(4-isopropylphenyl)-2H-benzimidazol-2-one

A) 4-Chloro-2-[(4-isopropylphenyl)amino]-1-nitrobenzene.

A mixture of 15 g of 4-chloro-1,2-nitrobenzene, 10 g of 4-isopropylaniline and 25 ml of Decalin® is heated at reflux for 15 hours. The reaction mixture is concentrated at 0.01 mmHg, the residue is taken up in water, extracted with ether, washed with 1N HCl solution, with water and dried over $Na_2SO_4$, and the solvent is evaporated off under vacuum. The residue is chromatographed on silica, eluting with iso ether. 13 g of the expected product are obtained, which product is used without further purification in the following step.

B) 4-Ethoxy-2-[(4-isopropylphenyl)amino]-1-nitrobenzene.

This compound is prepared according to the procedure described in Preparation 25 Step B, starting with 13 g of the compound obtained in the above step. The product is chromatographed on silica, eluting with pentane. 4.4 g of the expected product are obtained, mp=100.5° C.

C) 1-Amino-4-ethoxy-2-[(4-isopropylphenyl)amino]benzene.

This compound is prepared according to the procedure described in Preparation 25 Step C, starting with 4.3 g of the compound obtained in the above step. 4 g of the expected product are obtained, which product is used without further purification in the following step.

D) 4-Ethoxy-1-ethoxycarboxamido-2-[(4-isopropylphenyl)amino]benzene.

This compound is prepared according to the procedure described in Preparation 25 Step D, starting with 3.9 g of the compound obtained in the above step. The product is chromatographed on silica, eluting with iso ether. 5 g of the expected product are obtained, which product is used without further purification in the following step.

E) 5-Ethoxy-1,3-dihydro-3-(4-isopropylphenyl)-2H-benzimidazol-2-one.

This compound is prepared according to the procedure described in Preparation 25 Step E, starting with 4.9 g of the compound obtained in the above step. 2.8 g of the expected product are obtained after crystallization from EtOH, mp=202° C.

Preparation 27

5-Ethoxy-1,3-dihydro-3-(indan-2-yl)-2H-benzimidazol-2-one

A) 4-Chloro-2-[(indan-2-yl)amino]-1-nitrobenzene.

To sodium ethoxide solution, prepared from 0.61 g of sodium in 200 ml of EtOH, are added 26 g of 2-aminoindane hydrochloride and then 20 g of 4-chloro-1,2-dinitrobenzene and the mixture is left stirring for 48 hours at RT. The solvent is evaporated off under vacuum, the residue is extracted with EtOAc, washed with water and dried over $Na_2SO_4$, and the solvent is evaporated off under vacuum. 10.3 g of the expected product are obtained after crystallization from EtOH, mp=108° C.

B) 4-Ethoxy-2-[(indan-2-yl)amino]-1-nitrobenzene.

To sodium ethoxide solution, prepared from 2 g of sodium in 100 ml of EtOH, are added 10.3 g of the compound obtained in the above step and the mixture is heated at reflux for 4 hours. The solvent is evaporated off under vacuum, the residue is extracted with EtOAc, washed with water and dried over $Na_2SO_4$, and the solvent is evaporated off under vacuum. The residue is chromatographed on silica, eluting with DCM. 8.5 g of the expected product are obtained, mp=151° C.

C) 1-Amino-4-ethoxy-2-[(indan-2-yl)amino]benzene.

A mixture of 8.5 g of the compound obtained in the above step and 1 g of 5% palladium-on-charcoal in 500 ml of EtOAc is hydrogenated at RT and at atmospheric pressure. The catalyst is filtered off and the filtrate is evaporated under vacuum. 7.2 g of the expected product are obtained, which product is used without further purification in the following step.

D) 4-Ethoxy-1-ethoxycarboxamido-2-[(indan-2-yl)amino]benzene.

A mixture of 7.2 g of the compound obtained in the above step and 8.4 g of ethyl chloroformate in 100 ml of chloroform is heated at reflux for 2 hours. The mixture is extracted with chloroform, washed with 1N NaOH solution and dried over $Na_2SO_4$, and the solvent is evaporated off under vacuum. The residue is chromatographed on silica, eluting with DCM. 3.5 g of the expected product are obtained, mp=122° C.

E) 5-Ethoxy-1,3-dihydro-3-(indan-2-yl)-2H-benzimidazol-2-one.

To sodium ethoxide solution, prepared from 0.7 g of sodium in 50 ml of EtOH, are added 3.5 g of the compound obtained in the above step and the mixture is heated at reflux for 3 hours. The solvent is evaporated off under vacuum, the residue is taken up in water, extracted with DCM and dried over $Na_2SO_4$, and the solvent is evaporated off under vacuum. 2.6 g of the expected product are obtained after crystallization from EtOH, mp=225° C.

Preparation 28

3-(Adamant-1-yl)-5-ethoxy-1,3-dihydro-2H-benzimidazol-2-one

A) 2-[(Adamant-1-yl)amino]-4-chloro-1-nitrobenzene.

To a solution of 20 g of 4-chloro-1,2-dinitrobenzene in 80 ml of 96% EtOH are added 15.5 ml of triethylamine followed by a suspension of 15 g of 1-aminoadamantane in 50 ml of 96% EtOH. The mixture is heated at reflux for 7 hours and, after cooling, the precipitate formed is drained off. 7 g of the expected product are obtained, mp=146° C.

B) 2-[(Adamant-1-yl)amino]-4-ethoxy-1-nitrobenzene.

To sodium ethoxide solution, prepared from 0.6 g of sodium in 70 ml of EtOH, are added 7 g of the compound obtained in the above step and 8 ml of tris[2-(2-methoxyethoxy)ethyl]amine, and the mixture is heated at reflux for 3 hours. The solvent is evaporated off under vacuum, the residue is taken up in water, extracted with DCM and dried over $Na_2SO_4$, and the solvent is evaporated off under vacuum. 6 g of the expected product are obtained, mp=147° C.

C) 2-[(Adamant-1-yl)amino]-1-amino-4-ethoxybenzene.

A mixture of 6 g of the compound obtained in the above step and 0.85 g of 5% palladium-on-charcoal in 70 ml of 96% EtOH is hydrogenated at RT and at a pressure of 2 bar. The catalyst is filtered off and washed with EtOAc, and the filtrate is evaporated under vacuum. 4.7 g of the expected product are obtained, which product is used without further purification in the following step.

D) 2-[(Adamant-1-yl)amino]-4-ethoxy-1-ethoxycarboxamidobenzene.

A mixture of 4.7 g of the compound obtained in the above step and 6 ml of ethyl chloroformate in 70 ml of chloroform is heated at reflux for 1 hour 30 minutes. The solvent is evaporated off under vacuum, the residue is taken up in an iso ether/EtOAc mixture (50/50; v/v) and the precipitate formed is drained off. The precipitate is chromatographed on silica, eluting with DCM and then with a DCM/EtOAc mixture (80/20; v/v). 5 g of the expected product are obtained, which product is used without further purification in the following step.

E) 3-(Adamant-1-yl)-5-ethoxy-1,3-dihydro-2H-benzimidazol-2-one.

This compound is prepared according to the procedure described in Preparation 27 Step E, starting with 5 g of the compound obtained above. After evaporation of the solvent under vacuum, the residue is taken up in EtOAc and the precipitate formed is drained off. 2.5 g of the expected product are obtained, mp=264° C.

Preparation 29

3-Cycloheptyl-5-ethoxy-1,3-dihydro-2H-benzimidazol-2-one

A) 2-Cycloheptylamino-4-ethoxy-1-nitrobenzene.

To sodium ethoxide solution, prepared from 2.2 g of sodium in 250 ml of EtOH, are added 25 g of the compound obtained in Preparation 18 Step A and 30 ml of tris[2-(2-methoxyethoxy)ethyl]amine, and the mixture is heated at reflux for 24 hours. The mixture is concentrated under vacuum and the residue is chromatographed on silica, eluting with a DCM/heptane mixture (50/50; v/v). 14 g of the expected product are obtained, mp=83° C.

B) 1-Amino-2-cycloheptylamino-4-ethoxybenzene.

A mixture of 13 g of the compound obtained in the above step and 0.3 g of 5% palladium-on-charcoal in 250 ml of 95% EtOH is hydrogenated for 24 hours at RT and at a pressure of 2 bar. The catalyst is filtered off and the filtrate is evaporated under vacuum. The residue is chromatographed on silica, eluting with a DCM/heptane mixture (50/50; v/v), then with DCM and finally with a DCM/EtOAc mixture (90/10; v/v). 6 g of the expected product are obtained, which product is used without further purification in the following step.

C) 4-Ethoxy-1-ethoxycarboxamido-2-cycloheptylaminobenzene.

A mixture of 6 g of the compound obtained in the above step and 7.5 g of ethyl chloroformate in 50 ml of chloroform is heated at reflux for 5 hours. The mixture is concentrated under vacuum and the residue is chromatographed on silica, eluting with DCM. 4.7 g of the expected product are obtained after crystallization from iso ether, mp=172° C.

D) 3-Cycloheptyl-5-ethoxy-1,3-dihydro-2H-benzimidazol-2-one.

To sodium ethoxide solution, prepared from 0.35 g of sodium in 100 ml of EtOH, are added 4.5 g of the compound obtained in the above step and the mixture is heated at reflux for 24 hours. The mixture is concentrated under vacuum, the residue is extracted with EtOAc, washed with water and dried over $Na_2SO_4$, and the solvent is evaporated off under vacuum. 2.9 g of the expected product are obtained after crystallization from iso ether, mp=204° C.

Preparation 30

5-Chloro-3-(2-chlorophenyl)-1,3-dihydro-2H-benzimidazol-2-one

A) 1-Amino-4-chloro-2-[(2-chlorophenyl)amino]benzene.

A mixture of 3 g of the compound obtained in Preparation 12 Step A and 0.5 g of Raney nickel in 100 ml of 95% EtOH is hydrogenated for 4 hours at RT and at a pressure of 2 bar. The catalyst is filtered off and the filtrate is evaporated under vacuum. 2 g of the expected product are obtained, which product is used without further purification in the following step.

B) 5-Chloro-3-(2-chlorophenyl)-1,3-dihydro-2H-benzimidazol-2-one.

A mixture of 2 g of the compound obtained in the above step and 2 g of 1,1'-carbonyldiimidazole in 50 ml of acetonitrile is heated at reflux for 30 minutes. The reaction mixture is concentrated under vacuum, the residue is extracted with EtOAc, washed with 1N HCl solution, with water, with saturated NaHCO3 solution, with water and dried over $Na_2SO_4$, and the solvent is evaporated off under vacuum. 1 g of the expected product is obtained after crystallization from iso ether, mp=239° C.

Preparation 31

5-Ethoxy-1,3-dihydro-3-(pyrid-2-yl)-2H-benzimidazol-2-one

A) 4-Chloro-1-nitro-2-[(pyrid-2-yl)amino]benzene.

This compound is prepared according to the procedure described in Eur. J. Med. Chem.—Chim. Ther., 1983, 18 (6), 495–500.

B) 4-Ethoxy-1-nitro-2-[(pyrid-2-yl)amino]benzene.

To sodium ethoxide solution, prepared from 0.8 g of sodium in 50 ml of EtOH, are added 6.2 g of the compound obtained in the above step, and the mixture is heated at reflux for 3 hours. The reaction mixture is concentrated under vacuum, the residue is extracted with EtOAc, washed with water and dried over $Na_2SO_4$, and the solvent is evaporated off under vacuum. The residue is chromatographed on silica, eluting with a DCM/pentane mixture (50/50; v/v). 3.5 g of the expected product are obtained, which product is used without further purification in the following step.

C) 1-Amino-4-ethoxy-2-[(pyrid-2-yl)amino]benzene.

A mixture of 3.5 g of the compound obtained in the above step and 0.2 g of 5% palladium-on-charcoal in 250 ml of EtOAc is hydrogenated at RT and at atmospheric pressure. The catalyst is filtered off and the filtrate is evaporated under vacuum. 2.6 g of the expected product are obtained, mp=95° C.

D) 4-Ethoxy-1-ethoxycarboxamido-2-[(pyrid-2-yl)amino]benzene and 4-ethoxy-1-ethoxycarboxamido-2-[N-ethoxycarbonyl-N-(pyrid-2-yl)amino]benzene.

To a solution of 3.6 g of the compound obtained in the above step and 2 ml of triethylamine in 100 ml of DCM are added 2 ml of ethyl chloroformate, and the mixture is left stirring for 2 hours at RT. The reaction mixture is concentrated under vacuum, the residue is extracted with EtOAc, washed with water and dried over $Na_2SO_4$, and the solvent is evaporated off under vacuum. 3.2 g of a mixture of the two compounds mentioned in the title of Step D) are obtained, which mixture is used without further purification in the following step.

E) 5-Ethoxy-1,3-dihydro-3-(pyrid-2-yl)-2H-benzimidazol-2-one.

To sodium ethoxide solution, prepared from 0.6 g of sodium in 100 ml of EtOH, are added 3.2 g of the compound mixture obtained in the above step, and the resulting mixture is heated at reflux for 3 hours. The reaction mixture is concentrated under vacuum, the residue is extracted with EtOAc, washed with water and dried over $Na_2SO_4$, and the solvent is evaporated off under vacuum. 2.7 g of the expected product are obtained after crystallization from iso ether, mp=205° C.

Preparation 32

3-Cyclopentyl-5-ethoxy-1,3-dihydro-2H-benzimidazol-2-one

A) 4-Chloro-2-cyclopentylamino-1-nitrobenzene.

A mixture of 20 g of 4-chloro-1,2-dinitrobenzene and 20 g of cyclopentylamine in 50 ml of 95% EtOH is left stirring overnight at RT. The precipitate formed is drained off and washed with 95% EtOH. 14 g of the expected product are obtained, mp=75° C.

B) 2-Cyclopentylamino-4-ethoxy-1-nitrobenzene.

To sodium ethoxide solution, prepared from 2 g of sodium in 150 ml of EtOH, are added 20 ml of tris[2-(2-methoxyethoxy)ethyl]amine and 14 g of the compound obtained in the above step, and the mixture is then heated at reflux for 24 hours. The reaction mixture is concentrated under vacuum, the residue is extracted with EtOAc, washed with water and dried over $Na_2SO_4$, and the solvent is evaporated off under vacuum. The residue is chromatographed on silica, eluting with a DCM/heptane mixture (50/50; v/v). 10 g of the expected product are obtained, which product is used without further purification in the following step.

C) 1-Amino-2-cyclopentylamino-4-ethoxybenzene.

A mixture of 10 g of the compound obtained in the above step and 0.6 g of 5% palladium-on-charcoal in 200 ml of 95% EtOH is hydrogenated for 3 hours at RT and at a pressure of 2 bar. The catalyst is filtered off and the filtrate is evaporated under vacuum. 8.2 g of the expected product are obtained, which product is used without further purification in the following step.

D) 2-Cyclopentylamino-4-ethoxy-1-ethoxycarboxamidobenzene.

A mixture of 8 g of the compound obtained in the above step and 8 ml of ethyl chloroformate in 50 ml of chloroform is heated at reflux for 5 hours. The reaction mixture is concentrated under vacuum, the residue is taken up in a hot iso ether/EtOAc mixture (75/25; v/v) and the precipitate is drained off and washed with iso ether. 9.5 g of the expected product are obtained, mp=173° C.

E) 3-Cyclopentyl-5-ethoxy-1,3-dihydro-2H-benzimidazol-2-one.

To sodium ethoxide solution, prepared from 0.9 g of sodium in 225 ml of EtOH, are added 9.5 g of the compound obtained in the above step, and the mixture is heated at reflux for 18 hours. The reaction mixture is concentrated under vacuum, the residue is extracted with EtOAc, washed with water and dried over $Na_2SO_4$, and the solvent is evaporated off under vacuum. 4 g of the expected product are obtained after crystallization from an EtOAc/iso ether mixture (50/50; v/v), mp=178° C.

Preparations of the benzyl halides (III).

Preparation 33

1-Bromomethyl-3,4-dimethoxybenzene

A mixture of 15.2 g of 3,4-dimethoxytoluene, 17.8 g of N-bromosuccinimide and 0.3 g of dibenzoyl peroxide in 100 ml of $CCl_4$ is heated at reflux for hours, under illumination from a UV lamp. The precipitate is drained off and the filtrate is evaporated under vacuum. The residue is taken up in ether, washed with water, dried over $Na_2SO_4$ and evaporated under vacuum. An oil is obtained which contains a mixture of 50% of the expected product and 50% of the starting material, which mixture is used without further purification in the subsequent synthesis.

Preparation 34

1-Bromomethyl-3-methoxy-4-nitrobenzene

A mixture of 20 g of 3-methoxy-4-nitrotoluene, 21.6 g of N-bromosuccinimide and 0.3 g of dibenzoyl peroxide in 120 ml of $CCl_4$ is heated at reflux for 5 hours. The solvent is evaporated off under vacuum, the residue is taken up in water, extracted with DCM, washed with water, dried over $Na_2SO_4$ and evaporated under vacuum. 11.35 g of the expected product are obtained after crystallization from EtOH, mp=98° C.

Preparation 35

1-Bromomethyl-2-methoxy-4-nitrobenzene

A) 2-Hydroxy-4-nitrotoluene.

A mixture of 45.6 g of 2-methyl-5-nitroaniline in 680 ml of 10% sulfuric acid solution is left stirring for 1 hour, followed by cooling to 0° C. and dropwise addition of a solution of 21.7 g of sodium nitrite in 70 ml of water. The mixture is left stirring for 5 minutes at 0° C. and this solution is then stored at 0° C.

A solution of 460 ml of concentrated sulfuric acid in 910 ml of water is heated to reflux, the diazonium solution prepared above is added portionwise and heating (105° C.) is continued until the evolution of nitrogen ceases. After cooling, the reaction mixture is extracted three times with ether and washed with 10% $NaHCO_3$ solution, the phenol is extracted with 10% NaOH solution, the basic aqueous phase is acidified by addition of concentrated HCl and extracted with ether, the organic phase is dried over $Na_2SO_4$, and the solvent is evaporated off under vacuum. The residue is chromatographed on silica, eluting with a DCM/MeOH mixture (99/1; v/v). 28.6 g of the expected product are obtained after crystallization from EtOH, mp=118° C.

B) 2-Methoxy-4-nitrotoluene.

A mixture of 15.3 g of the compound obtained above, 20.7 g of potassium carbonate and 14.2 ml of dimethyl sulfate in 200 ml of acetone is heated at reflux for 3 hours. The solvent is evaporated off under vacuum, the residue is taken up in water, extracted with ether, washed with water, dried over $Na_2SO_4$ and evaporated under vacuum. 10.1 g of the expected product are obtained after crystallization from EtOH, mp=78° C.

C) 1-Bromomethyl-2-methoxy-4-nitrobenzene.

A mixture of 10 g of the compound obtained above in 90 ml of $CCl_4$ is brought to reflux, and 0.3 g of dibenzoyl peroxide and 10.7 g of N-bromosuccinimide are added in several portions. The mixture is left refluxing for 2 hours under illumination from a UV lamp, and the solvent is evaporated off under vacuum. The residue is taken up in water, extracted with ether, washed with water, dried over $Na_2SO_4$ and evaporated under vacuum. 9.3 g of the expected product are obtained after crystallization from EtOH, mp=94°–96° C.

Preparation 36

Methyl 4-bromomethyl-3-methoxybenzoate

This compound is prepared according to EP 0,179,619.

A) Methyl 3-methoxy-4-methylbenzoate.

To a mixture of 6 g of 3-methoxy-4-methylbenzoic acid in 120 ml of MeOH are added 6 ml of acetyl chloride, and the mixture is left stirring for 36 hours at RT. The solvent is evaporated off under vacuum, the residue is dissolved in 100 ml of MeOH and the solvent is again evaporated off under vacuum. 6.21 g of the expected product are obtained in the form of a yellow oil which crystallizes, mp=50°–52° C.

B) Methyl 4-bromomethyl-3-methoxybenzoate.

A solution of 6.2 g of the compound obtained in the above step in 50 ml of $CCl_4$ is heated to reflux and 0.17 g of dibenzoyl peroxide and 6.1 g of N-bromosuccinimide are added in several portions. The mixture is left stirring for 2 hours at reflux under illumination from a UV lamp, the solvent is evaporated off under vacuum, the residue is taken up in water, extracted with EtOAc, washed with water and dried over $Na_2SO_4$, and the solvent is evaporated off under vacuum. 4.34 g of the expected product are obtained after crystallization from EtOH, mp=92° C.

Preparation 37

N-(1,1-Dimethylpropyl)-4-bromomethylbenzenesulfonamide

To a solution of 10 g of 4-bromomethylbenzenesulfonyl chloride and 10 ml of triethylamine in 50 ml of toluene is added, dropwise at RT, a solution of 3.2 g of tert-amylamine in 10 ml of toluene, and the mixture is left stirring for 3 hours at RT. Water is then added to the reaction mixture and, after separation by settling, the organic phase is washed with water and dried over $Na_2SO_4$, and the solvent is evaporated off under vacuum. The residue is chromatographed on silica, eluting with a DCM/heptane mixture (50/50; v/v). 1 g of the expected product is obtained after crystallization from iso ether, mp=100° C.

Preparation 38

4-(6-Bromohexyloxy)benzyl bromide

A) 4-(6-Bromohexyloxy)toluene.

A mixture of 13.5 g of p-cresol, 26.4 g of 1,6-dibromohexane and 27.6 g of $K_2CO_3$ in 100 ml of acetone is heated at reflux for 15 hours. The reaction mixture is filtered and the filtrate is concentrated under vacuum. The residue is extracted with ether, the organic phase is washed with 1N NaOH solution, with water and dried over $Na_2SO_4$, and the solvent is evaporated off under vacuum. The oil obtained is distilled under vacuum. 15.3 g of a colorless oil are obtained, bp=125°–140° C. at 13.33 Pa.

B) 4-(6-Bromohexyloxy)benzyl bromide.

A mixture of 14.2 g of the compound obtained in the above step, 9.5 g of N-bromosuccinimide and 0.1 g of dibenzoyl peroxide in 30 ml of $CCl_4$ is heated at reflux for 5 hours. The reaction mixture is filtered and the filtrate is concentrated under vacuum. The oily residue is chromatographed on silica, eluting with petroleum ether. 5.5 g of the expected product are obtained, which product is used without further purification.

EXAMPLE 1

5-Chloro-3-cyclohexyl-1,3-dihydro-1-(3,4-dimethoxybenzyl)-2H-benzimidazol-2-one

To a solution of 0.5 g of the compound obtained in Preparation 1 in 3 ml of THF is added portionwise 0.066 g of 80% sodium hydride in oil, and the mixture is left stirring for 30 minutes. The mixture is cooled on an ice bath, 0.9 g of 1-bromomethyl-3,4-dimethoxybenzene (evaluated to be at a content of 50%, as a mixture with 3,4-dimethoxytoluene) and the mixture is left stirring for 72 hours, allowing the temperature to return to RT. The solvent is evaporated off under vacuum, the residue is extracted with ether, washed with water, dried over $Na_2SO_4$ and evaporated under vacuum. The residue is chromatographed on silica, eluting with a DCM/EtOAc mixture (90/10; v/v). 0.27 g of the expected product is obtained after concreting in hexane, mp=59° C.

EXAMPLE 2

5-Chloro-3-cyclohexyl-1,3-dihydro-1-(2,4-dimethoxybenzyl)-2H-benzimidazol-2-one

A solution of 0.537 g of 1-hydroxymethyl-2,4-dimethoxybenzene in 5 ml of ether is cooled to −10° C., under a nitrogen atmosphere, and a solution of 0.1 ml of phosphorus tribromide in 2 ml of ether is added dropwise. The 1-bromomethyl-2,4-dimethoxybenzene thus obtained is stored in solution at −30° C.

A solution of 0.531 g of the compound obtained in Preparation 1 in 25 ml of THF is cooled to −50° C., under a nitrogen atmosphere, and 0.250 g of potassium tert-butoxide is added, and the temperature is then allowed to rise to 0° C. with stirring. The mixture is cooled again to −50° C., 0.357 g of potassium tert-butoxide is added and the mixture is then cooled to −70° C. and the solution of the bromo derivative prepared above is added. The mixture is left stirring for 24 hours, allowing the temperature to return to RT. 5 ml of water are added, the solvents are evaporated off under vacuum and the residue is extracted with EtOAc, washed with water, dried over $Na_2SO_4$ and evaporated under vacuum. The residue is chromatographed on silica, eluting with a DCM/EtOAc mixture (95/5; v/v). 0.44 g of the expected product is obtained, which product crystallizes from hexane, mp=112° C.

EXAMPLE 3

5-Chloro-3-cyclohexyl-1,3-dihydro-1-(4-nitrobenzyl)-2H-benzimidazol-2-one

To a solution of 1.0 g of the compound obtained in Preparation 1 in 10 ml of DMF is added portionwise 0.130 g of 80% sodium hydride in oil and the mixture is left stirring for 30 minutes at RT. It is cooled in an ice bath, 0.950 g of 1-bromomethyl-4-nitrobenzene is added and the mixture is left stirring for 24 hours, allowing the temperature to return to RT. The solvent is evaporated off under vacuum, the residue is taken up in water, extracted with DCM, washed with water, dried over $Na_2SO_4$ and evaporated under vacuum. The residue is chromatographed on silica, eluting with a DCM/EtOAc mixture (95/5; v/v). 0.90 g of the expected product is obtained after crystallization from EtOH, mp=139° C.

EXAMPLE 4

5-Chloro-3-cyclohexyl-1,3-dihydro-1-(3-methoxy-4-nitrobenzyl)-2H-benzimidazol-2-one To a solution of 0.25 g of the compound obtained in Preparation 1 in 5 ml of DMF is added portionwise 0.033 g of 80% sodium hydride in oil and the mixture is left stirring for 30 minutes at RT. It is cooled in an ice bath, 0.25 g of 1-bromomethyl-3-methoxy-4-nitrobenzene is added and the mixture is left stirring for 72 hours, allowing the temperature to return to RT. The solvent is evaporated off under vacuum, the residue is taken up in water, extracted with DCM, washed with water, dried over $Na_2SO_4$ and evaporated under vacuum. The residue is chromatographed on silica, eluting with a DCM/EtOAc mixture (95/5; v/v). 0.125 g of the expected product is obtained after crystallization from EtOH, mp=176° C.

EXAMPLE 5

3-Cyclohexyl-5-ethoxy-1,3-dihydro-1-(2-methoxy-4-nitrobenzyl)-2H-benzimidazol-2-one To a solution, cooled to 10° C., of 4 g of the compound obtained in Preparation 3 in 40 ml of DMF is added portionwise 0.7 g of 60% sodium hydride in oil and the mixture is left stirring for 1 hour 30 minutes. It is cooled on an ice bath and 4 g of 1-bromomethyl-2-methoxy-4-nitrobenzene are added portionwise over 20 minutes, and the mixture is left stirring for 48 hours, allowing the temperature to return to RT. The reaction mixture is poured onto a mixture of water and ice, extracted with EtOAc, washed with water, dried over $Na_2SO_4$ and evaporated under vacuum. 4 g of the expected product are obtained after crystallization from iso ether, mp=120° C.

EXAMPLE 6

1-(4-Amino-2-methoxybenzyl)-3-cyclohexyl-5-ethoxy-1,3-dihydro-2H-benzimidazol-2-one A mixture of 3.5 g of the compound obtained in Example 5 in 350 ml of absolute EtOH, in the presence of Raney nickel, is hydrogenated for 20 hours at RT and at a pressure of 60 bar. The reaction mixture is filtered on Celite and the filtrate is evaporated under vacuum. The residue is chromatographed on silica, eluting with a DCM/EtOAc mixture (90/10; v/v). 2.7 g of the expected product are obtained after crystallization from an iso ether/EtOAc mixture, mp=191° C.

EXAMPLE 7

3-Cyclohexyl-5-ethoxy-1,3-dihydro-1-[2-methoxy-4-(phenoxycarboxamido)benzyl]-2H-benzimidazol-2-one A mixture of 1 g of the compound obtained in Example 6 in 40 ml of THF is cooled on an ice bath, followed by addition of a solution of 0.15 g of NaOH in 2 ml of water and dropwise addition of 1.5 ml of phenyl chloroformate. After stirring for 30 minutes, the solvent is evaporated off under vacuum, the residue is taken up in water, extracted with DCM, washed with water, dried over $Na_2SO_4$ and evaporated under vacuum. 1.1 g of the expected product are obtained after crystallization from iso ether, mp=189° C.

EXAMPLE 8

3-Cyclohexyl-5-ethoxy-1-[4-(N',N'-diethylureido)-2-methoxybenzyl]-1,3-dihydro-2H-benzimidazol-2-one To a solution of 0.6 g of the compound obtained in Example 7 in 25 ml of DCM is added 1 ml of diethylamine, and the mixture is left stirring for 20 hours at RT. The reaction mixture is evaporated under vacuum and the residue is chromatographed on silica, eluting with a DCM/EtOAc mixture (85/15; v/v) and then (80/20; v/v). 0.415 g of the expected product is obtained after crystallization from EtOAc, mp=158° C.

EXAMPLE 9

3-Cyclohexyl-5-ethoxy-1-[4-(N',N'-dimethylureido)-2-methoxybenzyl]-1,3-dihydro-2H-benzimidazol-2-one This compound is prepared according to the procedure described in Example 8, starting with 0.6 g of the compound obtained in Example 7 and 30 ml of a 33% solution of dimethylamine in EtOH. The product is chromatographed on silica, eluting with a DCM/EtOAc mixture (90/10; v/v). 0.43 g of the expected product is obtained after crystallization from an EtOAc/iso ether mixture, mp=250° C.

EXAMPLE 10

3-Cyclohexyl-5-ethoxy-1,3-dihydro-1-[4-[N'-methyl-N'-(2-hydroxyethyl)ureido]-2-methoxybenzyl]-2H-benzimidazol-2-one This compound is prepared according to the procedure described in Example 8, starting with 0.6 g of the compound obtained in Example 7 and 2 ml of 2-(methylamino)ethanol. The product is chromatographed on silica, eluting with a DCM/EtOAc mixture (90/10; v/v) and then with a DCM/MeOH mixture (90/10; v/v). 0.47 g of the expected product is obtained after crystallization from iso ether, mp=157° C.

EXAMPLE 11

1-[4-(2-Cyano-3-methylguanidino)-2-methoxybenzyl]-3-cyclohexyl-5-ethoxy-1,3-dihydro-2H-benzimidazol-2-one A) 1-[4-(3-Cyano-2-methyl-1-isothioureido)-2-methoxybenzyl]-3-cyclohexyl-5-ethoxy-1,3-dihydro-2H-benzimidazol-2-one, (R'$_6$=—NH—C(SMe)=N—CN).

A mixture of 1.0 g of the compound obtained in Example 6, 0.4 g of dimethyl N-cyanodithioiminocarbonate and 25 ml of n-butanol is heated at reflux for 24 hours and the reaction mixture is then concentrated under vacuum. The residue is chromatographed on silica, eluting with a DCM/EtOAc mixture (95/5; v/v) and then (85/15; v/v). 0.15 g of the expected product is obtained, mp=195° C.

B) 1-[4-(2-Cyano-3-methylguanidino)-2-methoxybenzyl]-3-cyclohexyl-5-ethoxy-1,3-dihydro-2H-benzimidazol-2-one.

A solution of 0.15 g of the compound obtained in the above step in 10 ml of a 33% solution of methylamine in EtOH is left stirring for 16 hours at RT. The reaction mixture is evaporated under vacuum and the residue is chromatographed on silica, eluting with a DCM/EtOAc mixture (80/20; v/v). 0.1 g of the expected product is obtained, mp=210° C.

EXAMPLE 12

5-Chloro-3-cyclohexyl-1-[4-(N',N'-diethylureido)-2-methoxybenzyl]-1,3-dihydro-2H-benzimidazol-2-one A) 5-Chloro-3-cyclohexyl-1,3-dihydro-1-(2-methoxy-4-nitrobenzyl)-2H-benzimidazol-2-one.

This compound is prepared according to the procedure described in Example 5, starting with 3 g of the compound obtained in Preparation 1 and 3 g of 1-bromomethyl-2-methoxy-4-nitrobenzene. 2 g of the expected product are obtained, which product is used without further purification in the following step.

B) 1-(4-Amino-2-methoxybenzyl)-5-chloro-3-cyclohexyl-1,3-dihydro-2H-benzimidazol-2-one.

This compound is prepared according to the procedure described in Example 6, starting with 2 g of the compound obtained in the above step. 1.5 g of the expected product are obtained, which product is used without further purification in the following step.

C) 5-Chloro-3-cyclohexyl-1,3-dihydro-1-[2-methoxy-4-(phenoxycarboxamido)benzyl]-2H-benzimidazol-2-one.

This compound is prepared according to the procedure described in Example 7, starting with 1.5 g of the compound obtained in the above step and 2 ml of phenyl chloroformate. 1.3 g of the expected product are obtained after crystallization from iso ether, mp=190° C.

D) 5-Chloro-3-cyclohexyl-1-[4-(N',N'-diethylureido)-2-methoxybenzyl]-1,3-dihydro-2H-benzimidazol-2-one.

This compound is prepared according to the procedure described in Example 8, starting with 0.7 g of the compound obtained in the above step and 2 ml of diethylamine. The product is chromatographed on silica, eluting with a DCM/EtOAc mixture (90/10; v/v). 0.47 g of the expected product is obtained after crystallization from iso ether, mp=205° C.

EXAMPLE 13

3-(2-Chlorophenyl)-5-ethoxy-1-[4-(N',N'-diethylureido)-2-methoxybenzyl]-1,3-dihydro-2H-benzimidazol-2-one A) 3-(2-Chlorophenyl)-5-ethoxy-1,3-dihydro-1-(2-methoxy-4-nitrobenzyl)-2H-benzimidazol-2-one.

This compound is prepared according to the procedure described in Example 5, starting with 0.74 g of the compound obtained in Preparation 12 and 0.7 g of 1-bromomethyl-2-methoxy-4-nitrobenzene. 0.5 g of the expected product is obtained, mp=150° C.

B) 1-(4-Amino-2-methoxybenzyl)-3-(2-chlorophenyl)-5-ethoxy-1,3-dihydro-2H-benzimidazol-2-one.

A mixture of 0.5 g of the compound obtained in the above step in 50 ml of EtOH, in the presence of Raney nickel, is hydrogenated at RT and at a pressure of 2 bar. The catalyst is filtered off on Celite and the filtrate is evaporated under vacuum. 0.3 g of the expected product is obtained, which product is used without further purification in the following step.

C) 3-(2-Chlorophenyl)-5-ethoxy-1,3-dihydro-1-[2-methoxy-4-(phenoxycarboxamido)benzyl]-2H-benzimidazol-2-one.

This compound is prepared according to the procedure described in Example 7, starting with 0.3 g of the compound obtained in the above step and 1 ml of phenyl chloroformate. 0.25 g of the expected product is obtained, which product is used without further purification in the following step.

D) 3-(2-Chlorophenyl)-5-ethoxy-1-[4-(N',N'-diethylureido)-2-methoxybenzyl]-1,3-dihydro-2H-benzimidazol-2-one.

This compound is prepared according to the procedure described in Example 8, starting with 0.25 g of the compound obtained in the above step and 1 ml of diethylamine. 0.05 g of the expected product is obtained after crystallization from iso ether, mp=181° C.

EXAMPLE 14

5-Ethoxy-1-[4-(N',N'-diethylureido)-2-methoxybenzyl]-1,3-dihydro-3-(tetrahydropyran-4-yl)-2H-benzimidazol-2-one A) 5-Ethoxy-1,3-dihydro-3-(tetrahydropyran-4-yl)-1-(2-methoxy-4-nitrobenzyl)-2H-benzimidazol-2-one.

This compound is prepared according to the procedure described in Example 5, starting with 1.2 g of the compound obtained in Preparation 13 and 1.5 g of 1-bromomethyl-2-methoxy-4-nitrobenzene. 1.2 g of the expected product are obtained after crystallization from an iso ether/EtOH mixture (80/20; v/v), mp=175° C.

B) 1-(4-Amino-2-methoxybenzyl)-5-ethoxy-1,3-dihydro-3-(tetrahydropyran-4-yl)-2H-benzimidazol-2-one.

A mixture of 1.2 g of the compound obtained in the above step and 0.15 g of 5% palladium-on-charcoal in 150 ml of EtOAc is hydrogenated at RT and at atmospheric pressure. The catalyst is filtered off and the filtrate is evaporated under vacuum. 1 g of the expected product is obtained, which product is used without further purification in the following step.

C) 5-Ethoxy-1,3-dihydro-3-(tetrahydropyran-4-yl)-1-[2-methoxy-4-(phenoxycarboxamido)benzyl]-2H-benzimidazol-2-one.

This compound is prepared according to the procedure described in Example 7, starting with 1.1 g of the compound obtained in the above step and 2 ml of phenyl chloroformate. 1.05 g of the expected product are obtained after crystallization from iso ether, mp=168° C.

D) 5-Ethoxy-1-[4-(N',N'-diethylureido-)-2-methoxybenzyl]-1,3-dihydro-3-(tetrahydropyran-4-yl)-2H-benzimidazol-2-one.

This compound is prepared according to the procedure described in Example 8, starting with 1.05 g of the compound obtained in the above step and 1 ml of diethylamine. The product is chromatographed on silica, eluting with a DCM/MeOH mixture (99/1; v/v). 0.49 g of the expected product is obtained, mp=201° C.

EXAMPLE 15

1-[4-(N-tert-Butylcarbamoyl)-2-methoxybenzyl]-3-cyclohexyl-5-ethoxy-1,3-dihydro-2H-benzimidazol-2-one A) Methyl 4-[[3-cyclohexyl-5-ethoxy-2,3-dihydro-2-oxo-1H-benzimidazol-1-yl]methyl]-3-methoxybenzoate.

To a solution of 0.53 g of the compound obtained in Preparation 3 in 20 ml of THF and 10 ml of DMF is added, portionwise at RT, 0.09 g of 60% sodium hydride in oil, and the mixture is left stirring for 30 minutes. 0.6 g of methyl 4-bromomethyl-3-methoxybenzoate is then added and the mixture is left stirring for 1 hour at RT. The solvents are evaporated off under vacuum, the residue is extracted with EtOAc, washed with water and dried over $Na_2SO_4$, and the solvent is evaporated off under vacuum. The residue is chromatographed on silica, eluting with DCM. 0.49 g of the expected product is obtained, which product is used without further purification in the following step.

B) 4-[[3-Cyclohexyl-5-ethoxy-2,3-dihydro-2-oxo-1H-benzimidazol-1-yl]methyl]-3-methoxybenzoic acid.

To a solution of 0.49 g of the compound obtained in the above step in 20 ml of THF is added a solution of 0.3 g of NaOH in 30 ml of water, and the mixture is left stirring for 3 hours at RT. The reaction mixture is extracted with EtOAc, the aqueous phase is acidified to pH=1 by addition of 1N HCl, extracted with EtOAc, the organic phase is dried over $Na_2SO_4$, and the solvent is evaporated off under vacuum. 0.45 g of the expected product is obtained, which product is used without further purification in the following step.

C) 1-[4-(N-tert-butylcarbamoyl)-2-methoxybenzyl]-3-cyclohexyl-5-ethoxy-1,3-dihydro-2H-benzimidazol-2-one.

To a solution of 0.45 g of the compound obtained in the above step, 0.52 g of BOP and 1 ml of DIPEA in 30 ml of DCM is added 0.5 g of tert-butylamine, and the mixture is left stirring for 2 hours at RT. The reaction mixture is washed with 1N HCl solution, with water, with 1N NaOH solution and dried over $Na_2SO_4$, and the solvent is evaporated off under vacuum. The residue is chromatographed on silica, eluting with a DCM/EtOAc mixture (85/15; v/v). 0.13 g of the expected product is obtained, mp=186° C.

EXAMPLE 16

3-Cyclohexyl-5-ethoxy-1,3-dihydro-1-[2-methoxy-4-[N-(1,1-dimethylpropyl)carbamoyl]benzyl]-2H-benzimidazol-2-one To a solution of 0.9 g of the compound obtained in Example 15 Step B, 0.9 g of BOP and 1 ml of DIPEA in 20 ml of DCM is added 1 g of tert-amylamine, and the mixture is left stirring for 3 hours at RT. The reaction mixture is washed with 1N HCl solution, with 1N NaOH solution and dried over $Na_2SO_4$, and the solvent is evaporated off under vacuum. The residue is chromatographed on silica, eluting with DCM. 0.34 g of the expected product is obtained, mp=164° C.

EXAMPLE 17

1-[4-(N-tert-Butylcarbamoyl)-2-methoxybenzyl]-5-ethoxy-1,3-dihydro-3-(tetrahydropyran-4-yl)-2H-benzimidazol-2-one A) Methyl 4-[[5-ethoxy-2,3-dihydro-3-(tetrahydropyran-4-yl)-2-oxo-1H-benzimidazol-1-yl]methyl]-3-methoxybenzoate.

This compound is prepared according to the procedure described in Example 15 Step A, starting with 0.6 g of the compound obtained in Preparation 13 and 0.7 g of methyl 4-bromomethyl-3-methoxybenzoate. 0.8 g of the expected product is obtained.

B) 4-[[5-ethoxy-2,3-dihydro-3-(tetrahydropyran-4-yl)-2-oxo-1H-benzimidazol-1-yl]methyl]-3-methoxybenzoic acid.

To a solution of 0.8 g of the compound obtained in the above step in 20 ml of THF is added a solution of 0.4 g of NaOH in 50 ml of water, and the mixture is left stirring for 5 hours at RT. 150 ml of water are added, the mixture is extracted with EtOAc, the aqueous phase is acidified to pH=1 by addition of 1N HCl, extracted with EtOAc, the organic phase is dried over $Na_2SO_4$, and the solvent is evaporated off under vacuum. 0.7 g of the expected product is obtained after crystallization from an iso ether/EtOH mixture (80/20; v/v), mp=209° C.

C) 1-[4-(N-tert-Butylcarbamoyl)-2-methoxybenzyl]-5-ethoxy-1,3-dihydro-3-(tetrahydropyran-4-yl)-2H-benzimidazol-2-one.

To a solution of 0.7 g of the compound obtained in the above step, 0.9 g of BOP and 1 ml of DIPEA in 20 ml of DCM are added 1.2 ml of tert-butylamine, and the mixture is left stirring for 3 hours at RT. The solvent is evaporated off under vacuum, the residue is extracted with EtOAc, washed with 1N HCl solution, with 1N NaOH solution, dried over $Na_2SO_4$ and evaporated under vacuum. The residue is chromatographed on silica, eluting with a DCM/MeOH mixture (99/1; v/v). 0.26 g of the expected product is obtained after crystallization from EtOAc, mp=211° C.

Working according to the procedures described in the above examples, starting with the 2-benzimidazolones described in the above preparations, the compounds according to the invention which are collated in Table I below are prepared.

TABLE I

| EXAMPLES | $R_1$ | $R_3$ | $R_5$ | $R_6$ | mp° C. or NMR crystallisation solvent |
|---|---|---|---|---|---|
| *18 (1) | —OMe | tetrahydropyran-4-yl | 3-OMe | 4-OMe | NMR |
| *19 (2) | —Cl | —CH$_2$—tetrahydropyran-4-yl | 2-OMe | 4-OMe | 80 cyclohexane/ iso ether |
| *20 (3) | —OEt | tetrahydropyran-4-yl | 2-OMe | 4-NHCON(Me)(Et) | 193 iso ether |
| *21 (3) | —OEt | tetrahydropyran-4-yl | 2-OMe | 4-NHCON(Et)(iPr) | 160 iso ether |
| *22 (4) | —OMe | tetrahydropyran-4-yl | 2-OMe | 4-NHCON(Et)(Et) | 149 iso ether |
| *23 (5) | —OEt | 4-Me-cyclohexyl (a,e) | 2-OMe | 4-NO$_2$ | 148 iso ether |
| *24 (6) | —OEt | 4-Me-cyclohexyl (a,e) | 2-OMe | 4-NH$_2$ | 155 iso ether |

TABLE I-continued (I)

[Structure: benzimidazol-2-one with R1 at 5-position, R3 on one N, and the other N bearing -CH2-phenyl group substituted with R5 and R6]

| EXAMPLES | R$_1$ | R$_3$ | R$_5$ | R$_6$ | mp° C. or NMR crystallisation solvent |
|---|---|---|---|---|---|
| *25 (7) | —OEt | 4-Me-cyclohexyl (a,e) | 2-OMe | 4-NHCOO-phenyl | 187 iso ether |
| *26 (8) | —OEt | cyclohexyl-Me(a) | 2-OMe | 4-NH$_2$ | 112 |
| *27 (7) | —OEt | cyclohexyl-Me(a) | 2-OMe | 4-NHCOO-phenyl | 166 |
| *28 (5) | —OEt | —C(Me)$_2$—CH$_2$—O—Me | 2-OMe | 4-NO$_2$ | 132 iso ether/ pentane |
| *29 (9) | —OEt | —C(Me)$_2$—CH$_2$—O—Me | 2-OMe | 4-NH$_2$ | 115 |
| *30 (7) | —OEt | —C(Me)$_2$—CH$_2$—O—Me | 2-OMe | 4-NHCOO-phenyl | 173 |
| *31 (10) | —OEt | —C(Me)$_2$—CH$_2$—C(Me)$_3$ | 2-OMe | 4-NHCOO-phenyl | 173 ether iso |
| *32 (8) | —O-cyclopentyl | cyclohexyl | 2-OMe | 4-NH$_2$ | 95 |
| *33 (7) | —O-cyclopentyl | cyclohexyl | 2-OMe | 4-NHCOO-phenyl | 166 iso ether |
| *34 (8) | —O—CH$_2$CH$_2$—O—Me | cyclohexyl | 2-OMe | 4-NH$_2$ | 163 |
| *35 (3) | —OEt | 4-Me-cyclohexyl (a,e) | 2-OMe | 4-NHCON(Et)$_2$ | 204 iso ether |

TABLE I-continued

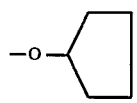

| EXAMPLES | R₁ | R₃ | R₅ | R₆ | mp° C. or NMR crystallisation solvent |
|---|---|---|---|---|---|
| *36 (3) | —OEt |  Me(a) | 2-OMe | 4-NHCON(Et)(Et) | 154 iso ether |
| *37 (4) | —OEt |  OMe (a,e) | 2-OMe | 4-NHCON(Et)(Et) | 151–153 iso ether |
| *38 (4) | —OEt |  OCH₂CH₂OMe (a,e) | 2-OMe | 4-NHCON(Et)(Et) | 153 iso ether |
| *39 (3) | —OEt | Me₂C(—CH₂—O—Me) | 2-OMe | 4-NHCON(Et)(Et) | 183 |
| *40 (3) | —OEt | Me₂C(—CH₂—CMe₃) | 2-OMe | 4-NHCON(Et)(Et) | 185 |
| *41 (3) | —O-cyclopentyl |  | 2-OMe | 4-NHCON(Et)(Et) | 166 iso ether |
| *42 (11) | —O—CH₂CH₂—O—Me | 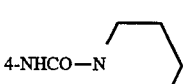 | 2-OMe | 4-NHCON(Et)(Et) | 138 iso ether |
| *43 (4) | —OEt | 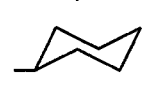 | 2-OMe | 5-NHCON(Et)(Et) | 187 EtOAc |
| *44 (4) | —OEt | cyclopentyl | 2-OMe | 4-NHCO—N(piperidine) | 195 EtOAc |
| *45 (3) | —OEt | 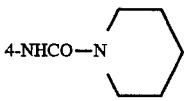 | 2-OMe | 4-NHCO—N(piperidine) | 210 EtOAc |

200 MHz NMR spectrum in DMSO of the compound of Example 18.

| | | |
|---|---|---|
| 1.8 to 2.3 ppm | mt | 10 H |
| 3.8 ppm | 3 × s | 9 H |
| 4.2 ppm | mt | 1 H |
| 4.95 ppm | s | 2 H |
| 6.6 to 7.1 ppm | mt | 6 H |

EXAMPLE 46

3-Cyclopentyl-5-ethoxy-1-[4-(N',N'-diethylureido)-2-methoxybenzyl]-1,3-dihydro-2H-benzimidazol-2-one A) 3-Cyclopentyl-5-ethoxy-1,3-dihydro-1-(2-methoxy-4-nitrobenzyl)-2H-benzimidazol-2-one.

This compound is prepared according to the procedure described in Example 5, starting with 1 g of the compound obtained in Preparation 32 and 1.5 g of 1-bromomethyl-2-methoxy-4-nitrobenzene. 1 g of the expected product is obtained after crystallization from iso ether, mp=114° C.

B) 1-(4-Amino-2-methoxybenzyl)-3-cyclopentyl-5-ethoxy-1,3-dihydro-2H-benzimidazol-2-one.

A mixture of 1 g of the compound obtained in the above step in 100 ml of 95% EtOH, in the presence of Raney nickel®, is hydrogenated for 30 minutes at RT and at a pressure of 2 bar. The catalyst is filtered off on Celite® and the filtrate is evaporated under vacuum. 0.7 g of the expected product is obtained, mp=164° C.

C) 3-Cyclopentyl-5-ethoxy-1,3-dihydro-1-[2-methoxy-4-(phenoxycarboxamido)benzyl]-2H-benzimidazol-2-one.

This compound is prepared according to the procedure described in Example 7, starting with 0.7 g of the compound obtained in the above step and 1 ml of phenyl chloroformate. 0.65 g of the expected product is obtained, mp=140° C.

D) 3-Cyclopentyl-5-ethoxy-1-[4-(N',N'-diethylureido)-2-methoxybenzyl]-1,3-dihydro-2H-benzimidazol-2-one.

This compound is prepared according to the procedure described in Example 8, starting with 0.33 g of the compound obtained in the above step and 2 ml of diethylamine. 0.25 g of the expected product is obtained after crystallization from an EtOAc/iso ether mixture (75/25; v/v), mp=158° C.

EXAMPLE 47

3-Cyclohexyl-5-ethoxy-1,3-dihydro-1-[2-methoxy-4-[N-(2-dimethylamino-1,1-dimethylethyl)carbamoyl]benzyl]-2H-benzimidazol-2-one A mixture of 1.5 g of the compound obtained in Example 15 Step B, 1 g of 2-dimethylamino-1,1-dimethylethylamine (synthesized according to J. Am. Chem. Soc., 1946, 68, 12–14), 1.6 g of BOP and 2 g of DIPEA in 20 ml of DCM is left stirring for 1 hour at RT. The reaction mixture is concentrated under vacuum, the residue is extracted with EtOAc, the organic phase is washed with 1N NaOH solution, with water and dried over Na$_2$SO$_4$, and the solvent is evaporated off under vacuum. The residue is chromatographed on silica, eluting with a DCM/MeOH mixture (98/2; v/v). 0.15 g of the expected product is obtained after crystallization from iso ether, mp=161° C.

EXAMPLE 48

3-Cyclohexyl-5-ethoxy-1,3-dihydro-1-[4-[N-(1,1-dimethylpropyl)sulfamoyl]benzyl]-2H-benzimidazol-2-one To a solution of 0.5 g of the compound obtained in Preparation 3 in 10 ml of DMF is added portionwise 0.1 g of 60% sodium hydride in oil, and the mixture is left stirring for 30 minutes. It is cooled on an ice bath, 0.6 g of N-(1,1-dimethylpropyl)-4-bromomethylbenzenesulfonamide is added and the mixture is left stirring for three hours, allowing the temperature to return to RT. The reaction mixture is poured into a water/ice mixture, extracted with EtOAc, the organic phase is washed with water and dried over Na$_2$SO$_4$, and the solvent is evaporated off under vacuum. The residue is chromatographed on silica, eluting with a DCM/EtOAc mixture (98.5/1.5; v/v) and then (97/3; v/v). 0.5 g of the expected product is obtained after crystallization from iso ether, mp=165° C.

EXAMPLE 49

3-Cyclohexyl-5-ethoxy-1,3-dihydro-1-[4-[6-(dimethylamino)hexyloxy]benzyl]-2H-benzimidazol-2-one hydrochloride A) 1-[4-(6-Bromohexyloxy)benzyl]-3-cyclohexyl-5-ethoxy-1,3-dihydro-2H-benzimidazol-2-one.

To a solution of 0.5 g of the compound obtained in Preparation 3 in 20 ml of THF is added, portionwise at RT, 0.06 g of 80% sodium hydride in oil, and the mixture is left stirring for 30 minutes. 1 g of 4-(6-bromohexyloxy)benzyl bromide is then added and the mixture is left stirring for 20 hours at RT. The reaction mixture is concentrated under vacuum, the residue is extracted with EtOAc, the organic phase is washed with water and dried over Na$_2$SO$_4$, and the solvent is evaporated off under vacuum. The residue is chromatographed on silica, eluting with hexane and then with iso ether. 1 g of the expected product is obtained, which product is used without further purification.

B) 3-Cyclohexyl-5-ethoxy-1,3-dihydro-1-[4-[6-(dimethylamino)hexyloxy]benzyl]-2H-benzimidazol-2-one hydrochloride.

A mixture of 0.5 g of the compound obtained in the above step, 10 ml of a 33% solution of dimethylamine in MeOH and 20 ml of THF is left stirring for 20 hours at RT. The reaction mixture is concentrated under vacuum, the residue is taken up in EtOAc, the organic phase is extracted with 1N HCl solution, the acidic aqueous phase is basified by addition of KOH pellets, extracted with EtOAc, the organic phase is washed with water and dried over Na$_2$SO$_4$, and the solvent is evaporated off under vacuum. The residue is dissolved in pentane, acidified to pH=1 by bubbling with HCl gas and is concentrated under vacuum. 0.15 g of the expected product is obtained after crystallization from an EtOAc/ether mixture, mp=90° C. (dec).

EXAMPLE 50

3-Cyclohexyl-5-ethoxy-1,3-dihydro-1-[2-methoxy-4-(pyrrol-1-yl)benzyl]-2H-benzimidazol-2-one A) 3-Cyclohexyl-5-ethoxy-1,3-dihydro-1-[2-methoxy-4-(Δ3-pyrrolin-1-yl)benzyl]-2H-benzimidazol-2-one.

A mixture of 1 g of the compound obtained in Example 6, 1 g of cis-1,4-dichloro-2-butene and 1 ml of triethylamine in 20 ml of DMF is heated at reflux for 1 hour 30 minutes under nitrogen atmosphere. After cooling, the reaction mixture is poured into a water/ice mixture, extracted with EtOAc, the organic phase is washed with water and dried over Na$_2$SO$_4$, and the solvent is evaporated off under vacuum. The residue is chromatographed on silica, eluting with DCM. 0.5 g of the expected product is obtained.

B) 3-Cyclohexyl-5-ethoxy-1,3-dihydro-1-[2-methoxy-4-(pyrrol-1-yl)benzyl]-2H-benzimidazol-2-one.

A solution of 0.7 g of benzoyl chloride in 2 ml of THF is cooled to 5°–10° C., 3 ml of 30% hydrogen peroxide solution in water is added dropwise and the mixture is left stirring for 30 minutes. The reaction mixture is taken up in chloroform and the organic phase is washed with water and dried over $Na_2SO_4$. A solution of 0.5 g of the compound obtained in the above step in 10 ml of chloroform is added to the solution obtained, and the mixture is left stirring overnight at RT and in the dark. The reaction mixture is washed with 1N NaOH solution and with water, the organic phase is dried over $Na_2SO_4$ and the solvent is evaporated off under vacuum. 0.3 g of the expected product is obtained after crystallization from iso ether, mp=115° C.

We claim:

1. A compound of formula:

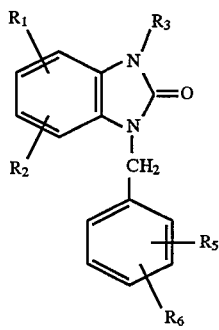

(I)

in which:

$R_1$ represents a halogen; a $(C_1-C_7)$alkyl; a $(C_1-C_7)$alkylthio; a phenylthio; a trifluoromethyl; a cyano; a nitro; a group —$NR_7R_8$; a hydroxyl; a $(C_1-C_7)$alkoxy; a $(C_3-C_7)$cycloalkyloxy; a $(C_3-C_7)$cycloalkylmethoxy; a phenoxy; a benzyloxy; an ω-halo$(C_1-C_7)$alkyloxy; a polyhalo$(C_1-C_7)$alkyloxy, an ω-hydroxy$(C_2-C_7)$alkyloxy; an ω-methoxy$(C_2-C_7)$alkyloxy;

$R_2$ represents a hydrogen, a halogen, a $(C_1-C_7)$alkyl;

$R_3$ represents $R_4$; a group —$(CH_2)_p$—$R_4$; an indanyl; a hexahydroindanyl; an adamantyl; a noradamantyl; a norbornyl; a $(C_1-C_8)$alkyl unsubstituted or substituted with a $(C_1-C_4)$alkoxy; a cyclohexyl substituted with a di$(C_1-C_7)$alkylamino, a carboxyl, a $(C_1-C_4)$alkoxycarbonyl, a hydroxyl, a 2-tetrahydropyranyloxy, a $(C_1-C_4)$alkoxy$(C_1-C_4)$alkoxy or a phenyl$(C_1-C_2)$alkoxy$(C_1-C_4)$alkoxy;

$R_4$ represents a group —$NR_9R_{10}$; a $(C_3-C_7)$cycloalkyl unsubstituted or substituted once or twice with a $(C_1-C_4)$alkyl or a $(C_1-C_4)$alkoxy; a furyl; a thienyl; a pyrrolyl; a triazolyl; a tetrazolyl; a pyridyl; a pyridyl N-oxide; a pyrimidinyl; a pyrazolyl; a pyrazinyl; a 4-tetrahydropyranyl; a 3-azetidinyl substituted in position 1 with $R_{11}$; a 4-piperidyl substituted in position 1 with $R_{11}$; a group Ar;

$R_5$ represents a hydrogen; a $(C_1-C_7)$alkyl; a $(C_1-C_7)$alkoxy; a halogen; a hydroxyl; a trifluoromethyl;

$R_6$ represents a cyano; a group —$CH_2NR_7R_8$; a nitro; a group —$NR_{12}R_{13}$; a group —NHOH; a guanidino which is unsubstituted or substituted in position 1 with a $(C_1-C_7)$alkyl and/or in position 3 with one or two $(C_1-C_7)$alkyls, a group Ar or a group —$CH_2$—Ar and/or in position 2 with a cyano; a group —$OR_{14}$; a group —$SR_{14}$; a $(C_1-C_7)$alkylcarbonyl; a group —$CONR_{15}R_{16}$; a thiocarbamoyl which is free or substituted with one or two $(C_1-C_7)$alkyls; a carboxyl; a $(C_1-C_7)$alkoxycarbonyl; a group —COO—Ar; a group —COO—$CH_2$—Ar; a group —CO—NH—$CR_{17}R_{18}$—$COR_{19}$; a group —$SO_2NR_{20}R_{21}$; a group —$NHSO_2$-$(C_1-C_7)$alkyl; a group —$NHSO_2$—Ar; a group —$NHSO_2$—$CH_2$—Ar; a dimethylaminosulfonamido;

$R_7$ and $R_8$ each independently represent a hydrogen or a $(C_1-C_7)$alkyl; $R_8$ may moreover represent a protecting group;

$R_9$ and $R_{10}$ each independently represent a hydrogen or a $(C_1-C_7)$alkyl;

or alternatively $R_9$ and $R_{10}$, together with the nitrogen atom to which they are attached, constitute a heterocycle chosen from morpholine, thiomorpholine, azetidine, pyrrolidine, piperidine, piperazine substituted in position 4 with $R_{11}$ or perhydroazepine;

$R_{11}$ represents a hydrogen; a $(C_1-C_7)$alkyl; a phenyl; a benzyl; a $(C_1-C_7)$alkylcarbonyl; a benzoyl; a $(C_1-C_7)$alkoxycarbonyl; a phenoxycarbonyl; a carbamoyl which is unsubstituted or substituted with one or two $(C_1-C_7)$alkyls;

$R_{12}$ and $R_{13}$ each independently represent a hydrogen; a $(C_1-C_7)$alkyl; a group —$CH_2$—Ar; $R_{13}$ may moreover represent a $(C_3-C_7)$cycloalkylmethyl; a group Ar; a group —$CH_2CH_2Ar$; a $(C_3-C_8)$alkenyl; a $(C_1-C_7)$alkylcarbonyl; a $(C_1-C_7)$alkylthiocarbonyl; a $(C_3-C_7)$cycloalkylcarbonyl; a $(C_3-C_7)$cycloalkylthiocarbonyl; a group —CO—Ar; a group —CO—$CH_2$—Ar; an ω-$R_7R_8N(C_2-C_7)$alkylcarbonyl; an ω-hydroxy$(C_1-C_7)$alkylcarbonyl; an ω-benzyloxy$(C_1-C_7)$alkylcarbonyl; a pyridylcarbonyl; a methylpyridylcarbonyl; a thienylcarbonyl; a furylcarbonyl; a 4-piperidylcarbonyl substituted in position 1 with $R_{11}$; a $(C_1-C_7)$alkoxycarbonyl; a phenoxycarbonyl; a phenoxythiocarbonyl; a benzyloxycarbonyl; a group —$CONR_{22}R_{23}$; a group —$CSNR_{22}R_{23}$; a group —CO—$CR_{17}R_{18}$—$NR_7R_8$; a group —$CR_{17}R_{18}COR_{19}$; a group —$(CH_2)_r$—$COR_{19}$; a group —CO—$(CH_2)_u$—$COR_{19}$;

or alternatively $R_{12}$ and $R_{13}$, together with the nitrogen atom to which they are attached, constitute hydantoin, N-methylhydantoin or a heterocyclic radical chosen from 1-pyrrolyl, Δ3-pyrrolin-1-yl, 1-pyrrolidinyl, 2-isoindolinyl in which the benzene ring is unsubstituted or substituted with a halogen, a $(C_1-C_7)$alkyl, a trifluoromethyl or a $(C_1-C_7)$alkoxy;

$R_{14}$ represents hydrogen; a $(C_1-C_7)$alkyl; a phenyl; a benzyl; a $(C_3-C_7)$cycloalkyl; a $(C_3-C_7)$alkenyl; an ω-halo$(C_2-C_7)$alkyl; a polyhalo$(C_1-C_7)$alkyl; an ω-hydroxy$(C_2-C_7)$alkyl; a $(C_1-C_7)$alkylcarbonyl; a benzoyl; an ω-carboxy$(C_1-C_7)$alkyl; an ω-$(C_1$-$C4)$alkoxycarbonyl$(C_1-C_7)$alkyl; an ω-benzyloxycarbonyl$(C_1-C_7)$alkyl; an ω-$R_7R_8N(C_2-C_7)$alkyl; an ω-carbamoyl$(C_1-C_7)$alkyl in which the carbamoyl is free or substituted with one or two $(C_1-C_7)$alkyls;

$R_{15}$ and $R_{16}$ each independently represent a hydrogen or a $(C_1-C_7)$alkyl; $R_{16}$ may moreover represent a $(C_3-C_7)$cycloalkyl which is unsubstituted or substituted with a $(C_1-C_4)$alkyl; a group Ar; a pyridyl; a methylpyridyl; a 4-piperidyl substituted in position 1 with $R_{11}$; a methylpiperid-4-yl; a 1-pyrrolidinyl; a 1-piperidyl; a 4-morpholinyl; a $(C_1-C_7)$alkyl substituted with one or more halogens or with $R_{24}$;

or alternatively $R_{15}$ and $R_{16}$, together with the nitrogen atom to which they are attached, represent a heterocyclic radical $R_{25}$;

$R_{17}$ and $R_{18}$ each independently represent hydrogen; a $(C_1-C_7)$alkyl; a benzyl;

or alternatively $R_{17}$ and $R_{18}$, together with the carbon atom to which they are attached, constitute a $(C_3-C_7)$cycloalkyl;

$R_{19}$ represents a hydroxyl; a $(C_1-C_7)$alkoxy; an amino which is free or substituted with one or two $(C_1-C_7)$ alkyls;

$R_{20}$ and $R_{21}$ each independently represent hydrogen; a $(C_1-C_7)$alkyl; $R_{21}$ may moreover represent a $(C_3-C_7)$ cycloalkyl;

or alternatively $R_{20}$ and $R_{21}$, together with the nitrogen atom to which they are attached, constitute a heterocyclic radical $R_{25}$;

$R_{22}$ and $R_{23}$ each independently represent hydrogen; a $(C_1-C_7)$alkyl; $R_{23}$ may moreover represent a $(C_3-C_7)$ cycloalkyl; an adamantyl; a group Ar; a hydroxyl; a $(C_1-C_4)$alkoxy; a $(C_1-C_7)$alkyl substituted with a group Ar, a pyridyl, a hydroxyl, a $(C_1-C_7)$alkoxy, a group —$NR_7R_8$, a carboxyl or a $(C_1-C_7)$ alkoxycarbonyl;

or alternatively $R_{22}$ and $R_{23}$, together with the nitrogen atom to which they are attached, constitute a heterocyclic radical $R_{25}$;

$R_{24}$ represents a hydroxyl; a $(C_1-C_7)$alkoxy; a cyano; a carboxyl; a $(C_1-C_7)$alkoxycarbonyl; a group —$NR_7R_8$; a carbamoyl which is free or substituted with one or two $(C_1-C_7)$alkyls; a benzyloxycarbonyl; a group Ar; a $(C_3-C_7)$cycloalkyl; an adamantyl; a 1-pyrrolidinylcarbonyl; a 1-piperidylcarbonyl; a perhydro-1-azepinylcarbonyl; a heterocyclic radical chosen from a pyridyl, a methylpyridyl, a furanyl, a tetrahydrofuranyl, a thienyl, a methylthienyl, a 1-pyrrolinyl, a 1-piperidyl or a perhydro-1-azepinyl;

$R_{25}$ represents a 4-morpholinyl; a 4-thiomorpholinyl; a 1-azetidinyl which is unsubstituted or substituted in position 2 with a carboxyl, a $(C_1-C_4)$alkoxycarbonyl or in position 3 with a group —$NR_7R_8$, a $(C_1-C_7)$alkyl, a phenyl, a benzyl or a $(C_1-C_7)$alkylcarbonyl; a perhydro-1-azepinyl; a 1-piperazinyl which is unsubstituted or substituted in position 4 with a $(C_1-C_7)$alkyl, a phenyl, a benzyl, a $(C_1-C_7)$alkylcarbonyl, a $(C_1-C_7)$ alkoxycarbonyl or a benzyloxycarbonyl; a 1-piperidyl which is unsubstituted or substituted in position 4 with a $(C_1-C_7)$alkyl, a phenyl, a benzyl, a $(C_1-C_7)$ alkylcarbonyl or a group —$NR_7R_8$; a cis-2,6-dimethyl-1-piperidyl; a 1-pyrrolidinyl which is unsubstituted or substituted with a $(C_1-C_7)$alkyl, a phenyl, a benzyl, a $(C_1-C_7)$alkylcarbonyl, a hydroxymethyl, a carboxyl, a $(C_1-C_7)$alkoxycarbonyl or a carbamoyl which is unsubstituted or substituted with one or two $(C_1-C_7)$ alkyls;

Ar represents a phenyl which is unsubstituted or substituted one or more times with a substituent chosen from: a halogen atom, a $(C_1-C_7)$alkyl, a trifluoromethyl, a hydroxyl, a $(C_1-C_7)$alkoxy, a carboxyl, a $(C_1-C_7)$ alkoxycarbonyl, a $(C_1-C_7)$alkylcarbonyloxy, a nitro, a cyano, an amino, a $(C_1-C_7)$alkylamino, a di$(C_1-C_7)$ alkylamino, the said substituents being identical or different;

t represents an integer which may range from 2 to 5;

u represents an integer which may range from 0 to 7;

p represents an integer which may range from 1 to 8 and the salts thereof, on condition that when $R_6$ represents a methoxy, $R_5$ is other than hydrogen.

2. The compound as claimed in claim 1, of formula:

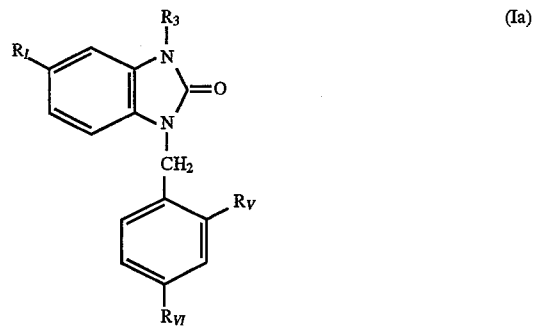

in which:

$R_1$ represents a $(C_1-C_4)$alkoxy or a chlorine or fluorine atom, $R_V$ represents hydrogen or a methoxy, $R_{VI}$ represents a $(C_1-C_7)$alkylcarboxamido, a group —NHCO—Ar, a group —$CONR_{15}R_{16}$ or a group —$NR_{12}CONR_{22}R_{23}$; and the substituents $R_3$, Ar, $R_{12}$, $R_{15}$, $R_{16}$, $R_{22}$ and $R_{23}$ are as defined in claim 1 for the compounds of formula (I);

as well as the salts thereof.

3. The compound as claimed in claim 2, of formula (Ia) in which $R_3$ represents a cyclohexyl or a group Ar.

4. A pharmaceutical composition containing (i) an effective amount of a compound as claimed in claim 1, or a pharmaceutically acceptable salt thereof and (ii) suitable excipients.

5. A pharmaceutical composition containing (i) an effective amount of a compound as claimed in claim 1, or a pharmaceutically acceptable salt thereof; (ii) an effective amount of another active principle and (iii) suitable excipients.

6. A pharmaceutical composition containing (i) effective amounts of two compounds as claimed in claim 1 or pharmaceutically acceptable salts thereof, one being an antagonist specific for the $V_1$ receptor and the other being an antagonist specific for the $V_2$ receptor and (ii) suitable excipients.

7. A pharmaceutical composition containing (i) effective amounts of two compounds as claimed in claim 1 or pharmaceutically acceptable salts thereof , one being an antagonist specific for the $V_1$ receptor and the other being an antagonist specific for oxytocin and (ii) suitable excipients.

8. A pharmaceutical composition containing (i) an effective amount of a compound as claimed in claim 2 or a pharmaceutically acceptable salt thereof; and (ii) suitable excipients.

9. A pharmaceutical composition containing (i) an effective amount of a compound as claimed in claim 3 or a pharmaceutically acceptable salt thereof; and (ii) suitable excipients.

10. A pharmaceutical composition containing (i) an effective amount of a compound as claimed in claim 2 or a pharmaceutically acceptable salt thereof; (ii) an effective amount of another active principal; and (iii) suitable excipients.

11. A pharmaceutical composition containing (i) an effective amount of a compound as claimed in claim 3 or a pharmaceutically acceptable salt thereof; (ii) an effective amount of another active principal; and (iii) suitable excipients.

12. A pharmaceutical composition containing (i) effective amounts of two compounds as claimed in claim 2 or pharmaceutically acceptable salts thereof, one being an antagonist specific for the $V_1$ receptor and the other being an antagonist specific for the $V_2$ receptor; and (ii) suitable excipients.

13. A pharmaceutical composition containing (i) effective amounts of two compounds as claimed in claim 3 or pharmaceutically acceptable salts thereof, one being an antagonist specific for the $V_1$ receptor and the other being an antagonist specific for the $V_2$ receptor; and (ii) suitable excipients.

14. A pharmaceutical composition containing (i) effective amounts of two compounds as claimed in claim 2 or pharmaceutically acceptable salts thereof, one being an antagonist specific for the $V_1$ receptor and the other being an antagonist specific for oxytocin; and (ii) suitable excipients.

15. A pharmaceutical composition containing (i) effective amounts of two compounds as claimed in claim 3 or pharmaceutically acceptable salts thereof, one being an antagonist specific for the $V_1$ receptor and the other being an antagonist specific for oxytocin; and (ii) suitable excipients.

16. A compound according to claim 1, which is 3-cyclohexyl-5-ethoxy-1,3-dihydro-1-[2-methoxy-4-[N-(1,1-dimethylpropyl)carbamoyl]benzyl]-2H-benzimidazol-2-one, or the salts thereof.

17. A compound according to claim 1, which is 3-cyclohexyl-5-ethoxy-1-[4-(N',N'-diethylureido)-2-methoxybenzyl]-1,3-dihydro-2H-benzimidazol-2-one, or the salts thereof.

18. A pharmaceutical composition containing (i) an effective amount of a compound as claimed in claim 16, or a pharmaceutically acceptable salt thereof and (ii) suitable excipients.

19. A pharmaceutical composition containing (i) an effective amount of a compound as claimed in claim 17, or a pharmaceutically acceptable salt thereof and (ii) suitable excipients.

20. A pharmaceutical composition containing (i) an effective amount of a compound as claimed in claim 16, or a pharmaceutically acceptable salt thereof, (ii) an effective amount of another active principle and (iii) suitable excipients.

21. A pharmaceutical composition containing (i) an effective amount of a compound as claimed in claim 17, or a pharmaceutically acceptable salt thereof, (ii) an effective amount of another active principle and (iii) suitable excipients.

22. A pharmaceutical composition containing (i) effective amounts of two compounds as claimed in claim 20, or pharmaceutically acceptable salts thereof, one being an antagonist specific for the $V_1$ receptor and the other being an antagonist specific for the $V_2$ receptor and (ii) suitable excipients.

23. A pharmaceutical composition containing (i) effective amounts of two compounds as claimed in claim 21, or pharmaceutically acceptable salts thereof, one being an antagonist specific for the $V_1$ receptor and the other being an antagonist specific for the $V_2$ receptor and (ii) suitable excipients.

24. A pharmaceutical composition containing (i) effective amounts of two compounds as claimed in claim 20, or pharmaceutically acceptable salts thereof, one being an antagonist specific for the $V_1$ receptor and the other being an antagonist specific for oxytocin and (ii) suitable excipients.

25. A pharmaceutical composition containing (i) effective amounts of two compounds as claimed in claim 21, or pharmaceutically acceptable salts thereof, one being an antagonist specific for the $V_1$ receptor and the other being an antagonist specific for oxytocin and (ii) suitable excipients.

* * * * *